US012297427B2

(12) United States Patent
Thomas et al.

(10) Patent No.: US 12,297,427 B2
(45) Date of Patent: May 13, 2025

(54) CLONING AND EXPRESSION SYSTEM FOR T-CELL RECEPTORS

(71) Applicant: St. Jude Children's Research Hospital, Inc., Memphis, TN (US)

(72) Inventors: Paul Thomas, Memphis, TN (US); Xizhi Guo, Memphis, TN (US); Pradyot Dash, Memphis, TN (US)

(73) Assignee: ST. JUDE CHILDREN'S RESEARCH HOSPITAL, INC., Memphis, TN (US)

( * ) Notice: Subject to any disclaimer, the term of this patent is extended or adjusted under 35 U.S.C. 154(b) by 1998 days.

(21) Appl. No.: 15/780,938

(22) PCT Filed: Dec. 2, 2016

(86) PCT No.: PCT/US2016/064735
§ 371 (c)(1),
(2) Date: Jun. 1, 2018

(87) PCT Pub. No.: WO2017/096239
PCT Pub. Date: Jun. 8, 2017

(65) Prior Publication Data
US 2019/0040381 A1    Feb. 7, 2019

Related U.S. Application Data

(60) Provisional application No. 62/263,318, filed on Dec. 4, 2015.

(51) Int. Cl.
| C40B 50/06 | (2006.01) |
| C07K 14/725 | (2006.01) |
| C12N 15/10 | (2006.01) |
| C12N 15/66 | (2006.01) |

(52) U.S. Cl.
CPC ...... *C12N 15/1031* (2013.01); *C07K 14/7051* (2013.01); *C12N 15/10* (2013.01); *C12N 15/1003* (2013.01); *C12N 15/66* (2013.01); *C12N 2310/11* (2013.01); *C40B 50/06* (2013.01)

(58) Field of Classification Search
None
See application file for complete search history.

(56) References Cited

U.S. PATENT DOCUMENTS

| 2007/0141048 A1 | 6/2007 | Oleksiewicz et al. |
| 2011/0142842 A1 | 6/2011 | Olweus et al. |
| 2015/0203886 A1 | 7/2015 | Kishi et al. |
| 2015/0337369 A1 | 11/2015 | Davis et al. |

OTHER PUBLICATIONS

Communication issued by the International Searching Authority in International Patent Application No. PCT/US2016/064735 dated Jun. 5, 2018 (International Preliminary Report on Patentability) 8 pages total.

(Continued)

*Primary Examiner* — Christian C Boesen
(74) *Attorney, Agent, or Firm* — Troutman Pepper Locke LLP

(57) ABSTRACT

The invention provides a method for rapid cloning of T-cell receptors (TCRs) (e.g., paired αβ and γδ TCR chains) and B-cell receptors (BCRs) (e.g. paired IgH or IgK or Igλ) from single cells by CDR3 substitution using single cell PCR products and Gibson Assembly techniques and a pre-generated TCR (or BCR) library in an expression vector.

11 Claims, 7 Drawing Sheets
Specification includes a Sequence Listing.

(56) References Cited

OTHER PUBLICATIONS

Linnemann, C, et al. High-throughput identification of antigen-specific TCRs by TCR gene capture. Nat Med, 2013, 19:1534-1541.

Kobayashi, E, et al. A new cloning and expression system yields and validates TCRs from blood lymphocytes of patients with cancer within 10 days. Nat Med, 2013, 19:1542-1546.

Howie, B, et al. High-throughput pairing of T cell receptor α and β sequences. Sci Transl Med, 2015, 7:301ra131.

Dash, P, et al. Paired analysis of TCRα and TCRβ chains at the single-cell level in mice. J Clin Invest, 2011, 121: 288-295.

Wang, GC, et al. T cell receptor αβ diversity inversely correlates with pathogen-specific antibody levels in human cytomegalovirus infection. Sci Transl Med, 2012, 4:128ra42.

Communication issued by the International Searching Authority in International Patent Application No. PCT/US2016/064735 dated Feb. 8, 2017 (International Search Report).

Communication issued by the International Searching Authority in International Patent Application No. PCT/US2016/064735 dated Feb. 8, 2017 (Written Opinion).

Dash, P. et al., "Paired Analysis of TCRα and TCRβ Chains at the Single-Cell Level in Mice" Journal of Clinical Investigation (2011) vol. 121, No. 1, pp. 288-295.

Kobayashi, E. et al., "A New Cloning and Expression System Yields and Validates TCRs from Blood Lymphocytes of Patients with Cancer Within 10 Days" Nature Medicine (2013) vol. 19, No. 11, pp. 1542-1546.

Vogl, T. et al., "Restriction Site-Free Cloning (RSFC) Plasmid Family for Seamless, Sequence Independent Cloning in Pichia Pastoris" Microbial Cell Factories (2015) vol. 103, pp. 1-15.

Wang, G.C. et al., "T-Cell Receptor αβ Diversity Inversely Correlates with Pathogen-Specific Antibody Levels in human Cytomegalovirus Infection" Science Translational Medicine (2012) vol. 4, Issue 128, pp. 1-11.

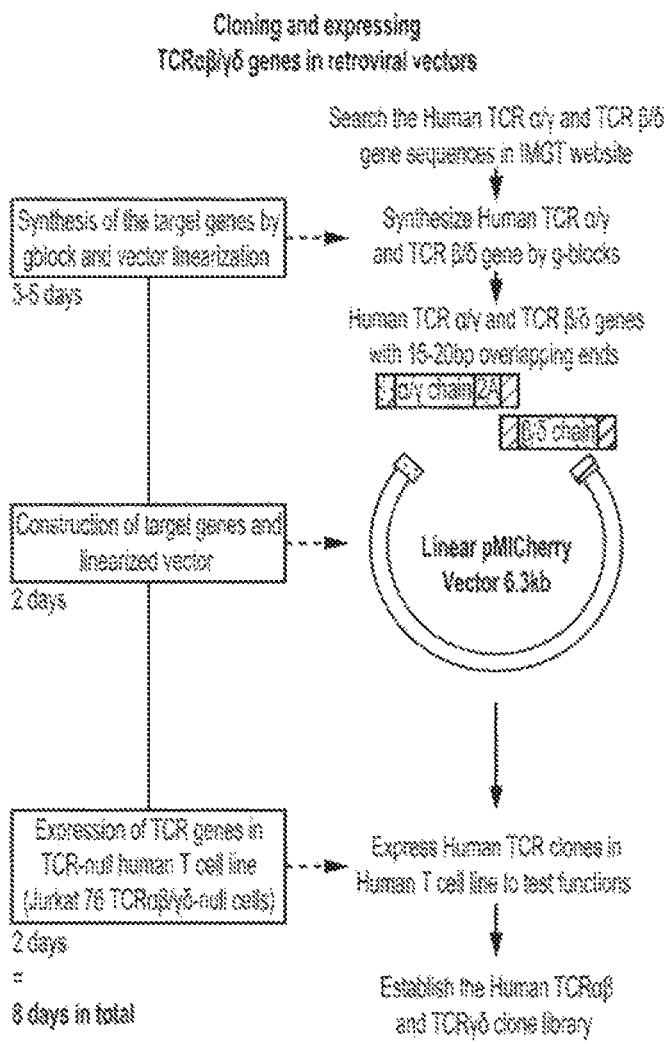
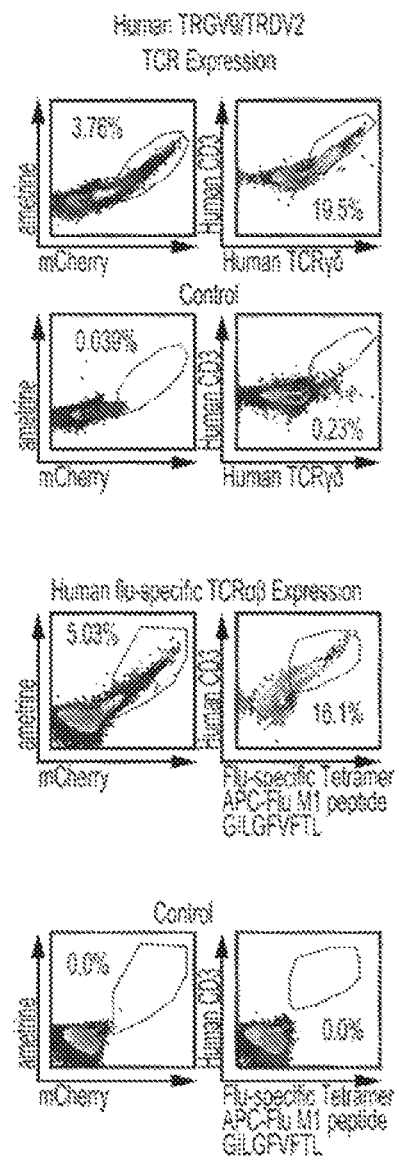
FIG. 2A
FIG. 2B

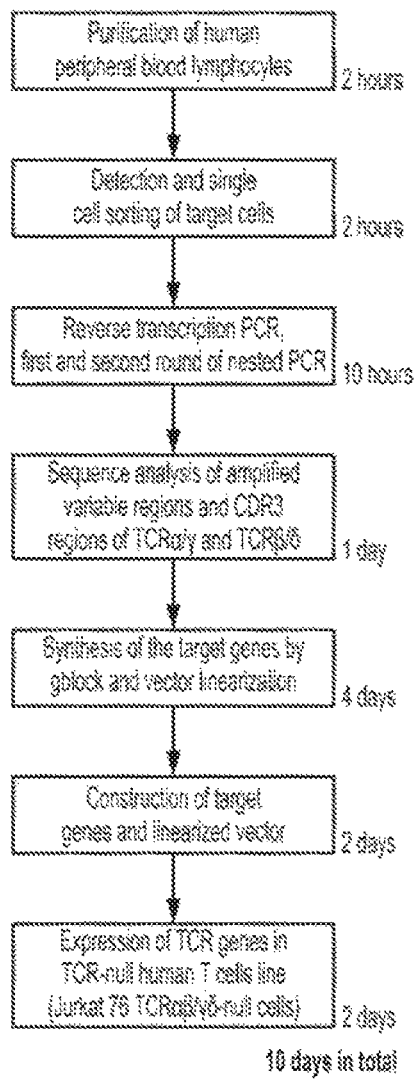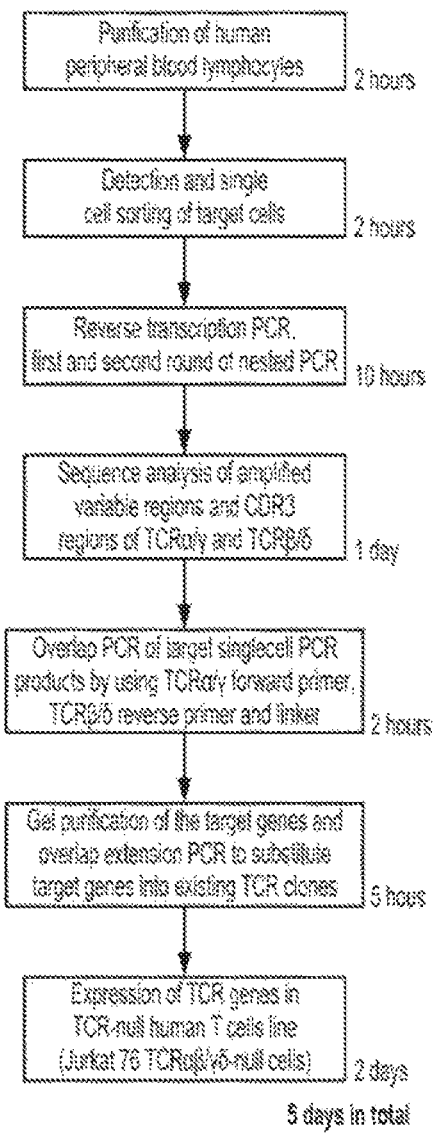
FIG. 5A
FIG. 5B

SEQUENCE LISTING

```
<160> NUMBER OF SEQ ID NOS: 315

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tcttccaact tggaaggg                                                  18
```

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggtcatctgc tgaaatcac                                                19

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcttccaact tgcaaggg                                                 18

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggtcatctgc tgtaatcact tg                                            22

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gggtcatcct gtttccag                                                 18

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tacctaagga cctgtgtaga gg                                            22

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tggcctccca aagtactg                                                 18

```
<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcctctttct atgtcccagg                                              20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccaacttgga agggagaac                                               19

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaaatgccgt ctacaccc                                                18

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccaggtcacc tagagcaac                                               19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgtccatttc atatgacgg                                               19

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttatcaaaag tggagcagtt c                                            21
```

```
<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cagctatcca tttccacgg                                                    19

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gaacaacctg aaatatctat ttcc                                              24

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
catatcttgg aaggcatcc                                                    19

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gggtcatctg ctgaaatcac                                                   20

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccaggagggg aaggc                                                        15

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggtgttcccc tcctgg                                                       16

<210> SEQ ID NO 20
```

<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cccagaatcg tgttgct                                                     17

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcccagaagg ttactcaag                                                   19

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agcaaagaga tgattttcct ta                                               22

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
attgagttgg tgcctgaac                                                   19

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tatatcaact ggtacaggaa gacc                                             24

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tgtgacaaag taacccagag ttc                                              23

<210> SEQ ID NO 26
<211> LENGTH: 22

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggtactgctc tgcacttacg ac                                              22

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
caaacccaac caggaatg                                                   18

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aggaaaagga ggctgtgac                                                  19

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcaagttaag caaaattcac c                                               21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctgctgaagg tcctacattc                                                 20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttgatagtcc agaaaggagg                                                 20

<210> SEQ ID NO 32
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 32
cgtttgacta ctttccatgg                                                   20

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gacaaggtgg tacaaagcc                                                    19

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
atctctggtt gtccacgag                                                    19

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cagtcactca gtctcaacca g                                                 21

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tctggtacaa gcagcctc                                                     18

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cttcatattt accaagcttg acag                                              24

<210> SEQ ID NO 38
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 38
gatgacaata gcaggatcaa ac                                              22

<210> SEQ ID NO 39
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ccctcactcc ttctctaggc gccggaattc gccaggatgg aacatagcac g              51

<210> SEQ ID NO 40
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ccacgtctcc cgccaacttg agaaggtcaa aattcaaagt ctgtttcacc ggtcccttgt     60
tccgagcc                                                              68

<210> SEQ ID NO 41
<211> LENGTH: 67
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gaattttgac cttctcaagt tggcgggaga cgtggagtcc aacccagggc ccatggaaca     60
ggggaag                                                               67

<210> SEQ ID NO 42
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cctcgacgtc accgcatgtt agcagacttc ctctgccctc agatcttcta ttcctcctca     60
ac                                                                    62

<210> SEQ ID NO 43
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cagaggaagt ctgctaacat gcggtgacgt cgaggagaat cctggcccaa tgcagtcggg     60
``` cactc                                                                   65

<210> SEQ ID NO 44
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gttttcttcc acgtctcctg cttgctttaa cagagagaag ttcgtggcgg atcctccgat    60
gcgtctctg                                                            69

<210> SEQ ID NO 45
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ctctctgtta aagcaagcag gagacgtgga agaaaacccc ggtcccatga agtggaaagt    60
g                                                                    61

<210> SEQ ID NO 46
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gagggagagg ggcggaattg atcctcgagc aattgttagc gaggggccag               50

<210> SEQ ID NO 47
<211> LENGTH: 22
<212> TYPE: PRT
<213> ORGANISM: Foot-and-mouth disease virus

<400> SEQUENCE: 47

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 48
<211> LENGTH: 18
<212> TYPE: PRT
<213> ORGANISM: Thosea asigna virus

<400> SEQUENCE: 48

Glu Gly Arg Gly Ser Leu Leu Thr Cys Gly Asp Val Glu Glu Asn Pro
1               5                   10                  15

Gly Pro

<210> SEQ ID NO 49
<211> LENGTH: 19
<212> TYPE: PRT
<213> ORGANISM: Porcine teschovirus 1

<400> SEQUENCE: 49

Ala Thr Asn Phe Ser Leu Leu Lys Gln Ala Gly Asp Val Glu Glu Asn
1               5                   10                  15

Pro Gly Pro

<210> SEQ ID NO 50
<211> LENGTH: 702
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50 cataccttttg tcttcttgag aaattttttcc cagatattat taagatacat tggcaagaaa     60
agaagagcaa cacgattctg ggatcccagg aggggaacac catgaagact aacgacacat    120
acatgaaatt tagctggtta acggtgccag aagagtcact ggacaaagaa cacagatgta    180
tcgtcagaca tgagaataat aaaaacggaa ttgatcaaga aattatcttt cctccaataa    240
agacagatgt catcacaatg gatcccaaag acaattggtc aaaagatgca aatgatacac    300
tactgctgca gctcacaaac acctctgcat attacatgta cctcctcctg ctcctcaaga    360
gtgtggtcta ttttgccatc atcacctgct gtctgcttgg aagaacggct ttctgctgca    420
atggagagaa atcagccacg aacttctctc tgttaaagca agcaggagac gtggaagaaa    480
accccggtcc catgctgttc tccagcctgc tgtgtgtatt tgtggccttc agctactctg    540
gatcaagtgt ggcccagaag gttactcaag cccagtcatc agtatccatg ccagtgagga    600
aagcagtcac cctgaactgc ctgtatgaaa caagttggtg gtcatattat atttttttggt    660 acaagcaact tcccagcaaa gagatgattt tccttattcg cc                       702

<210> SEQ ID NO 51
<211> LENGTH: 676
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51 cataccttttg tcttcttgag aaattttttcc cagatattat taagatacat tggcaagaaa     60
agaagagcaa cacgattctg ggatcccagg aggggaacac catgaagact aacgacacat    120
acatgaaatt tagctggtta acggtgccag aagagtcact ggacaaagaa cacagatgta    180
tcgtcagaca tgagaataat aaaaacggaa ttgatcaaga aattatcttt cctccaataa    240
agacagatgt catcacaatg gatcccaaag acaattggtc aaaagatgca aatgatacac    300
tactgctgca gctcacaaac acctctgcat attacatgta cctcctcctg ctcctcaaga    360
gtgtggtcta ttttgccatc atcacctgct gtctgcttgg aagaacggct ttctgctgca    420
atggagagaa atcagccacg aacttctctc tgttaaagca agcaggagac gtggaagaaa    480
accccggtcc catgcagagg atctcctccc tcatccatct ctctctcttc tgggcaggag    540
tcatgtcagc cattgagttg gtgcctgaac accaaacagt gcctgtgtca atagggtcc     600 ctgccaccct caggtgctcc atgaaaggag aagcgatcgg taactactat atcaactggt    660
acaggaagac ccaagg                                                    676

<210> SEQ ID NO 52
<211> LENGTH: 624

<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 52

| | |
|---|---|
| cataccttg tcttcttgag aaattttcc cagatattat taagatacat tggcaagaaa | 60 |
| agaagagcaa cacgattctg ggatcccagg aggggaacac catgaagact aacgacacat | 120 |
| acatgaaatt tagctggtta acggtgccag aagagtcact ggacaaagaa cacagatgta | 180 |
| tcgtcagaca tgagaataat aaaaacggaa ttgatcaaga aattatcttt cctccaataa | 240 |
| agacagatgt catcacaatg gatcccaaag acaattggtc aaaagatgca aatgatacac | 300 |
| tactgctgca gctcacaaac acctctgcat attacatgta cctcctcctg ctcctcaaga | 360 |
| gtgtggtcta ttttgccatc atcacctgct gtctgcttgg aagaacggct ttctgctgca | 420 |
| atggagagaa atcagccacg aacttctctc tgttaaagca agcaggagac gtggaagaaa | 480 |
| accccggtcc catgattctt actgtgggct ttagcttttt gttttctac aggggcacgc | 540 |
| tgtgtgacaa agtaacccag agttccccgg accagacggt ggcgagtggc agtgaggtgg | 600 |
| tactgctctg cacttacgac actg | 624 |

<210> SEQ ID NO 53
<211> LENGTH: 615
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 53

| | |
|---|---|
| cataccttg tcttcttgag aaattttcc cagatattat taagatacat tggcaagaaa | 60 |
| agaagagcaa cacgattctg ggatcccagg aggggaacac catgaagact aacgacacat | 120 |
| acatgaaatt tagctggtta acggtgccag aagagtcact ggacaaagaa cacagatgta | 180 |
| tcgtcagaca tgagaataat aaaaacggaa ttgatcaaga aattatcttt cctccaataa | 240 |
| agacagatgt catcacaatg gatcccaaag acaattggtc aaaagatgca aatgatacac | 300 |
| tactgctgca gctcacaaac acctctgcat attacatgta cctcctcctg ctcctcaaga | 360 |
| gtgtggtcta ttttgccatc atcacctgct gtctgcttgg aagaacggct ttctgctgca | 420 |
| atggagagaa atcagccacg aacttctctc tgttaaagca agcaggagac gtggaagaaa | 480 |
| accccggtcc catgtcactt tctagcctgc tgaaggtggt cacagcttca ctgtggctag | 540 |
| gacctggcat tgcccagaag ataactcaaa cccaaccagg aatgttcgtg caggaaaagg | 600 |
| aggctgtgac tctgg | 615 |

<210> SEQ ID NO 54
<211> LENGTH: 715
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 54

| | |
|---|---|
| cataccttg tcttcttgag aaattttcc cagatattat taagatacat tggcaagaaa | 60 |
| agaagagcaa cacgattctg ggatcccagg aggggaacac catgaagact aacgacacat | 120 |
| acatgaaatt tagctggtta acggtgccag aagagtcact ggacaaagaa cacagatgta | 180 |

```
tcgtcagaca tgagaataat aaaaacggaa ttgatcaaga aattatcttt cctccaataa    240
agacagatgt catcacaatg gatcccaaag acaattggtc aaaagatgca aatgatacac    300
tactgctgca gctcacaaac acctctgcat attacatgta cctcctcctg ctcctcaaga    360
gtgtggtcta ttttgccatc atcacctgct gtctgcttgg aagaacggct ttctgctgca    420
atggagagaa atcagccacg aacttctctc tgttaaagca agcaggagac gtggaagaaa    480
accccggtcc catggccatg ctcctggggg catcagtgct gattctgtgg cttcagccag    540
actgggtaaa cagtcaacag aagaatgatg accagcaagt taagcaaaat tcaccatccc    600
tgagcgtcca ggaaggaaga atttctattc tgaactgtga ctatactaac agcatgtttg    660
attatttcct atggtacaaa aaatacccto ctgaaggtcc tacattcctg atatc         715
```

<210> SEQ ID NO 55
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
cataccttg tcttcttgag aaattttcc cagatattat taagatacat tggcaagaaa      60
agaagagcaa cacgattctg ggatcccagg aggggaacac catgaagact aacgacacat    120
acatgaaatt tagctggtta acggtgccag aagagtcact ggacaaagaa cacagatgta    180
tcgtcagaca tgagaataat aaaaacggaa ttgatcaaga aattatcttt cctccaataa    240
agacagatgt catcacaatg gatcccaaag acaattggtc aaaagatgca aatgatacac    300
tactgctgca gctcacaaac acctctgcat attacatgta cctcctcctg ctcctcaaga    360
gtgtggtcta ttttgccatc atcacctgct gtctgcttgg aagaacggct ttctgctgca    420
atggagagaa atcagccacg aacttctctc tgttaaagca agcaggagac gtggaagaaa    480
accccggtcc catggacaag atcttaggag catcattttt agttctgtgg cttcaactat    540
gctgggtgag tggccaacag aaggagaaaa gtgaccagca gcaggtgaaa caaagtcctc    600
aatctttgat agtccagaaa ggagggattt caattataaa ctgtgcttat gagaacactg    660
cgtttgacta ctttccatgg tacc                                         684
```

<210> SEQ ID NO 56
<211> LENGTH: 603
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

```
cataccttg tcttcttgag aaattttcc cagatattat taagatacat tggcaagaaa      60
agaagagcaa cacgattctg ggatcccagg aggggaacac catgaagact aacgacacat    120
acatgaaatt tagctggtta acggtgccag aagagtcact ggacaaagaa cacagatgta    180
tcgtcagaca tgagaataat aaaaacggaa ttgatcaaga aattatcttt cctccaataa    240
agacagatgt catcacaatg gatcccaaag acaattggtc aaaagatgca aatgatacac    300
tactgctgca gctcacaaac acctctgcat attacatgta cctcctcctg ctcctcaaga    360
gtgtggtcta ttttgccatc atcacctgct gtctgcttgg aagaacggct ttctgctgca    420
```

```
atggagagaa atcagccacg aacttctctc tgttaaagca agcaggagac gtggaagaaa      480
accccggtcc catgatgaag tgtccacagg ctttactagc tatcttttgg cttctactga      540
gctgggtgag cagtgaagac aaggtggtac aaagccctct atctctggtt gtccacgagg      600
gag                                                                    603
```

<210> SEQ ID NO 57
<211> LENGTH: 676
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
catacctttg tcttcttgag aaattttttcc cagatattat taagatacat tggcaagaaa      60
agaagagcaa cacgattctg ggatcccagg aggggaacac catgaagact aacgacacat     120
acatgaaatt tagctggtta acggtgccag aagagtcact ggacaaagaa cacagatgta     180
tcgtcagaca tgagaataat aaaaacggaa ttgatcaaga aattatcttt cctccaataa     240
agacagatgt catcacaatg gatcccaaag acaattggtc aaaagatgca aatgatacac     300
tactgctgca gctcacaaac acctctgcat attacatgta cctcctcctg ctcctcaaga     360
gtgtggtcta ttttgccatc atcacctgct gtctgcttgg aagaacggct ttctgctgca     420
atggagagaa atcagccacg aacttctctc tgttaaagca agcaggagac gtggaagaaa     480
accccggtcc catggcatgc cctggcttcc tgtgggcact tgtgatctcc acctgtcttg     540
aatttagcat ggctcagaca gtcactcagt ctcaaccaga gatgtctgtg caggaggcag     600
agaccgtgac cctgagctgc acatatgaca ccagtgagag tgattattat ttattctggt     660
acaagcagcc tcccag                                                     676
```

<210> SEQ ID NO 58
<211> LENGTH: 13
<212> TYPE: PRT
<213> ORGANISM: Homo sapiens

<400> SEQUENCE: 58

Ala Leu Phe Ile Gln Glu Leu Gly Lys Lys Ile Lys Val
1               5                   10

<210> SEQ ID NO 59
<211> LENGTH: 13
<212> TYPE: PRT
<213> ORGANISM: Homo sapiens

<400> SEQUENCE: 59

Ala Cys Asp Val Leu Gly Asp Thr Glu Gly Arg Leu Ile
1               5                   10

<210> SEQ ID NO 60
<211> LENGTH: 11
<212> TYPE: PRT
<213> ORGANISM: Homo sapiens

<400> SEQUENCE: 60

Ala Leu Trp Asp Gly Pro Tyr Tyr Lys Lys Leu
1               5                   10

<210> SEQ ID NO 61
<211> LENGTH: 19

-continued

```
<212> TYPE: PRT
<213> ORGANISM: Homo sapiens

<400> SEQUENCE: 61

Ala Cys Asp Thr Val Phe Thr Gly Gly Tyr Ser Ser Trp Asp Thr Arg
1               5                   10                  15

Gln Met Phe

<210> SEQ ID NO 62
<211> LENGTH: 17
<212> TYPE: PRT
<213> ORGANISM: Homo sapiens

<400> SEQUENCE: 62

Ala Leu Trp Asp Ile Pro Pro Gly Gln Glu Leu Gly Lys Lys Ile Lys
1               5                   10                  15

Val

<210> SEQ ID NO 63
<211> LENGTH: 17
<212> TYPE: PRT
<213> ORGANISM: Homo sapiens

<400> SEQUENCE: 63

Ala Cys Asp Thr Leu Gly Glu Thr Ser Ser Trp Asp Thr Arg Gln Met
1               5                   10                  15

Phe

<210> SEQ ID NO 64
<211> LENGTH: 14
<212> TYPE: PRT
<213> ORGANISM: Homo sapiens

<400> SEQUENCE: 64

Ala Leu Trp Glu Ala Gln Glu Leu Gly Lys Lys Ile Lys Val
1               5                   10

<210> SEQ ID NO 65
<211> LENGTH: 16
<212> TYPE: PRT
<213> ORGANISM: Homo sapiens

<400> SEQUENCE: 65

Ala Cys Asp Ser Gly Gly Tyr Ser Ser Trp Asp Thr Arg Gln Met Phe
1               5                   10                  15

<210> SEQ ID NO 66
<211> LENGTH: 15
<212> TYPE: PRT
<213> ORGANISM: Homo sapiens

<400> SEQUENCE: 66

Ala Leu Trp Glu Ala Arg Gln Glu Leu Gly Lys Lys Ile Lys Val
1               5                   10                  15

<210> SEQ ID NO 67
<211> LENGTH: 16
<212> TYPE: PRT
<213> ORGANISM: Homo sapiens

<400> SEQUENCE: 67

Ala Cys Asp Thr Leu Phe Pro Gly Gly Ser Ala Thr Asp Lys Leu Ile
1               5                   10                  15
```

<210> SEQ ID NO 68
<211> LENGTH: 17
<212> TYPE: PRT
<213> ORGANISM: Homo sapiens

<400> SEQUENCE: 68

Ala Leu Trp Glu Gly Thr Arg Gly Gln Glu Leu Gly Lys Lys Ile Lys
1               5                   10                  15

Val

<210> SEQ ID NO 69
<211> LENGTH: 13
<212> TYPE: PRT
<213> ORGANISM: Homo sapiens

<400> SEQUENCE: 69

Ala Cys Asp Thr Val Gly Ala His Thr Asp Lys Leu Ile
1               5                   10

<210> SEQ ID NO 70
<211> LENGTH: 16
<212> TYPE: PRT
<213> ORGANISM: Homo sapiens

<400> SEQUENCE: 70

Ala Leu Trp Glu Val Gly Asp Gln Glu Leu Gly Lys Lys Ile Lys Val
1               5                   10                  15

<210> SEQ ID NO 71
<211> LENGTH: 19
<212> TYPE: PRT
<213> ORGANISM: Homo sapiens

<400> SEQUENCE: 71

Ala Cys Asp Pro Leu Asn Thr Gly Gly Ser Phe Ser Leu Tyr Thr Asp
1               5                   10                  15

Lys Leu Ile

<210> SEQ ID NO 72
<211> LENGTH: 15
<212> TYPE: PRT
<213> ORGANISM: Homo sapiens

<400> SEQUENCE: 72

Ala Leu Trp Glu Val His Ser Glu Leu Gly Lys Lys Ile Lys Val
1               5                   10                  15

<210> SEQ ID NO 73
<211> LENGTH: 17
<212> TYPE: PRT
<213> ORGANISM: Homo sapiens

<400> SEQUENCE: 73

Ala Cys Asp Thr Gly Gly Phe Arg Ser Ser Trp Asp Thr Arg Gln Met
1               5                   10                  15

Phe

<210> SEQ ID NO 74
<211> LENGTH: 14
<212> TYPE: PRT
<213> ORGANISM: Homo sapiens

```
<400> SEQUENCE: 74

Ala Leu Trp Glu Val Leu Glu Leu Gly Lys Lys Ile Lys Val
1               5                   10

<210> SEQ ID NO 75
<211> LENGTH: 16
<212> TYPE: PRT
<213> ORGANISM: Homo sapiens

<400> SEQUENCE: 75

Ala Cys Asp Thr Val Gly Met Gly Ile Arg Leu Gly Asp Lys Leu Ile
1               5                   10                  15

<210> SEQ ID NO 76
<211> LENGTH: 16
<212> TYPE: PRT
<213> ORGANISM: Homo sapiens

<400> SEQUENCE: 76

Ala Leu Trp Glu Val Leu Val Gly Glu Leu Gly Lys Lys Ile Lys Val
1               5                   10                  15

<210> SEQ ID NO 77
<211> LENGTH: 13
<212> TYPE: PRT
<213> ORGANISM: Homo sapiens

<400> SEQUENCE: 77

Ala Cys Asp Ile Leu Gly Ile Asn Thr Asp Lys Leu Ile
1               5                   10

<210> SEQ ID NO 78
<211> LENGTH: 14
<212> TYPE: PRT
<213> ORGANISM: Homo sapiens

<400> SEQUENCE: 78

Ala Leu Trp Glu Val Pro Glu Leu Gly Lys Lys Ile Lys Val
1               5                   10

<210> SEQ ID NO 79
<211> LENGTH: 14
<212> TYPE: PRT
<213> ORGANISM: Homo sapiens

<400> SEQUENCE: 79

Ala Cys Glu Arg Leu Gly Asp Tyr Val Pro Asp Lys Leu Ile
1               5                   10

<210> SEQ ID NO 80
<211> LENGTH: 14
<212> TYPE: PRT
<213> ORGANISM: Homo sapiens

<400> SEQUENCE: 80

Ala Leu Trp Glu Val Gln Glu Leu Gly Lys Lys Ile Lys Val
1               5                   10

<210> SEQ ID NO 81
<211> LENGTH: 13
<212> TYPE: PRT
<213> ORGANISM: Homo sapiens

<400> SEQUENCE: 81
```

```
Ala Cys Asp Arg Leu Leu Gly Asp Thr Asp Lys Leu Ile
1               5                   10
```

<210> SEQ ID NO 82
<211> LENGTH: 19
<212> TYPE: PRT
<213> ORGANISM: Homo sapiens

<400> SEQUENCE: 82

```
Ala Cys Asp Thr Val Ala Pro Arg Ile Gly Gly Leu Lys Tyr Thr Asp
1               5                   10                  15

Lys Leu Ile
```

<210> SEQ ID NO 83
<211> LENGTH: 14
<212> TYPE: PRT
<213> ORGANISM: Homo sapiens

<400> SEQUENCE: 83

```
Ala Cys Asp Thr Val Gly Gly Pro Tyr Thr Asp Lys Leu Ile
1               5                   10
```

<210> SEQ ID NO 84
<211> LENGTH: 10
<212> TYPE: PRT
<213> ORGANISM: Homo sapiens

<400> SEQUENCE: 84

```
Ala Cys Asp Thr Val Gly Gly Thr Ala Gln
1               5                   10
```

<210> SEQ ID NO 85
<211> LENGTH: 19
<212> TYPE: PRT
<213> ORGANISM: Homo sapiens

<400> SEQUENCE: 85

```
Ala Cys Asp Thr Val Ser Gly Gly Ser Thr Pro Thr Trp Tyr Thr Asp
1               5                   10                  15

Lys Leu Ile
```

<210> SEQ ID NO 86
<211> LENGTH: 17
<212> TYPE: PRT
<213> ORGANISM: Homo sapiens

<400> SEQUENCE: 86

```
Ala Cys Asp Thr Val Ser Ile Phe Thr Gly Asp Thr Thr Asp Lys Leu
1               5                   10                  15

Ile
```

<210> SEQ ID NO 87
<211> LENGTH: 14
<212> TYPE: PRT
<213> ORGANISM: Homo sapiens

<400> SEQUENCE: 87

```
Ala Leu Trp Glu Val Arg Glu Leu Gly Lys Lys Ile Lys Val
1               5                   10
```

<210> SEQ ID NO 88
<211> LENGTH: 19
<212> TYPE: PRT

```
<213> ORGANISM: Homo sapiens

<400> SEQUENCE: 88

Ala Cys Asp Thr Ile Leu Ile Phe Ser Pro Thr Gly Gly Asp Thr Asp
1               5                   10                  15

Lys Leu Ile

<210> SEQ ID NO 89
<211> LENGTH: 13
<212> TYPE: PRT
<213> ORGANISM: Homo sapiens

<400> SEQUENCE: 89

Ala Cys Val Pro Leu Gly Asp Trp Thr Asp Lys Leu Ile
1               5                   10

<210> SEQ ID NO 90
<211> LENGTH: 16
<212> TYPE: PRT
<213> ORGANISM: Homo sapiens

<400> SEQUENCE: 90

Ala Leu Trp Glu Val Arg Lys Gln Glu Leu Gly Lys Lys Ile Lys Val
1               5                   10                  15

<210> SEQ ID NO 91
<211> LENGTH: 13
<212> TYPE: PRT
<213> ORGANISM: Homo sapiens

<400> SEQUENCE: 91

Ala Cys Asp Thr Leu Gly Asp Asp Phe Asp Lys Leu Ile
1               5                   10

<210> SEQ ID NO 92
<211> LENGTH: 18
<212> TYPE: PRT
<213> ORGANISM: Homo sapiens

<400> SEQUENCE: 92

Ala Leu Trp Glu Val Thr His Asn Arg Gln Glu Leu Gly Lys Lys Ile
1               5                   10                  15

Lys Val

<210> SEQ ID NO 93
<211> LENGTH: 17
<212> TYPE: PRT
<213> ORGANISM: Homo sapiens

<400> SEQUENCE: 93

Ala Cys Asp Thr Leu Leu Gly Thr Glu Ala Trp Asp Thr Arg Gln Met
1               5                   10                  15

Phe

<210> SEQ ID NO 94
<211> LENGTH: 14
<212> TYPE: PRT
<213> ORGANISM: Homo sapiens

<400> SEQUENCE: 94

Ala Leu Trp Gly Gly Ala Ala Gly Ala Tyr Tyr Lys Lys Leu
1               5                   10
```

```
<210> SEQ ID NO 95
<211> LENGTH: 13
<212> TYPE: PRT
<213> ORGANISM: Homo sapiens

<400> SEQUENCE: 95

Ala Cys Asp Gly Lys Thr Thr Asp Thr Asp Lys Leu Ile
1               5                   10

<210> SEQ ID NO 96
<211> LENGTH: 13
<212> TYPE: PRT
<213> ORGANISM: Homo sapiens

<400> SEQUENCE: 96

Ala Leu Trp Gly Gly Glu Leu Gly Lys Lys Ile Lys Val
1               5                   10

<210> SEQ ID NO 97
<211> LENGTH: 15
<212> TYPE: PRT
<213> ORGANISM: Homo sapiens

<400> SEQUENCE: 97

Ala Cys Asp Leu Leu Gly Asp Thr Arg Tyr Thr Asp Lys Leu Ile
1               5                   10                  15

<210> SEQ ID NO 98
<211> LENGTH: 13
<212> TYPE: PRT
<213> ORGANISM: Homo sapiens

<400> SEQUENCE: 98

Ala Leu Trp Val Gln Glu Leu Gly Lys Lys Ile Lys Val
1               5                   10

<210> SEQ ID NO 99
<211> LENGTH: 13
<212> TYPE: PRT
<213> ORGANISM: Homo sapiens

<400> SEQUENCE: 99

Ala Cys Val Gly Ile Thr Gly Asp Thr Asp Lys Leu Ile
1               5                   10

<210> SEQ ID NO 100
<211> LENGTH: 15
<212> TYPE: PRT
<213> ORGANISM: Homo sapiens

<400> SEQUENCE: 100

Ala Leu Trp Glu Ala His Gln Glu Leu Gly Lys Lys Ile Lys Val
1               5                   10                  15

<210> SEQ ID NO 101
<211> LENGTH: 13
<212> TYPE: PRT
<213> ORGANISM: Homo sapiens

<400> SEQUENCE: 101

Ala Cys Asp Ser Leu Gly Asp Ser Val Asp Lys Leu Ile
1               5                   10

<210> SEQ ID NO 102
```

```
<211> LENGTH: 9
<212> TYPE: PRT
<213> ORGANISM: Homo sapiens

<400> SEQUENCE: 102

Ala Leu Trp Glu Ala Asn Lys Lys Leu
1               5

<210> SEQ ID NO 103
<211> LENGTH: 16
<212> TYPE: PRT
<213> ORGANISM: Homo sapiens

<400> SEQUENCE: 103

Ala Cys Asp Leu Leu Arg Gly Ala Gly Gly Gln Ile Asp Lys Leu Ile
1               5                   10                  15

<210> SEQ ID NO 104
<211> LENGTH: 14
<212> TYPE: PRT
<213> ORGANISM: Homo sapiens

<400> SEQUENCE: 104

Ala Leu Trp Glu Ala Gln Glu Leu Gly Lys Lys Ile Lys Val
1               5                   10

<210> SEQ ID NO 105
<211> LENGTH: 15
<212> TYPE: PRT
<213> ORGANISM: Homo sapiens

<400> SEQUENCE: 105

Ala Cys Asp Thr Val Gly Gly Ala Phe Asp Thr Asp Lys Leu Ile
1               5                   10                  15

<210> SEQ ID NO 106
<211> LENGTH: 14
<212> TYPE: PRT
<213> ORGANISM: Homo sapiens

<400> SEQUENCE: 106

Ala Leu Trp Glu Ala Thr Gly Leu Gly Lys Lys Ile Lys Val
1               5                   10

<210> SEQ ID NO 107
<211> LENGTH: 16
<212> TYPE: PRT
<213> ORGANISM: Homo sapiens

<400> SEQUENCE: 107

Ala Cys Asp Met Gly Asp Thr Arg Ser Trp Asp Thr Arg Gln Met Phe
1               5                   10                  15

<210> SEQ ID NO 108
<211> LENGTH: 14
<212> TYPE: PRT
<213> ORGANISM: Homo sapiens

<400> SEQUENCE: 108

Ala Leu Trp Glu Asp Leu Glu Leu Gly Lys Lys Ile Lys Val
1               5                   10

<210> SEQ ID NO 109
<211> LENGTH: 15
<212> TYPE: PRT
```

<213> ORGANISM: Homo sapiens

<400> SEQUENCE: 109

Ala Cys Asp Thr Val Ser Trp Gly Lys Asn Thr Asp Lys Leu Ile
1               5                   10                  15

<210> SEQ ID NO 110
<211> LENGTH: 14
<212> TYPE: PRT
<213> ORGANISM: Homo sapiens

<400> SEQUENCE: 110

Ala Leu Trp Glu Lys Glu Leu Gly Lys Lys Ile Lys Val
1               5                   10

<210> SEQ ID NO 111
<211> LENGTH: 17
<212> TYPE: PRT
<213> ORGANISM: Homo sapiens

<400> SEQUENCE: 111

Ala Cys Asp Thr Gly Asp Trp Gly Ser Ser Trp Asp Thr Arg Gln Met
1               5                   10                  15

Phe

<210> SEQ ID NO 112
<211> LENGTH: 13
<212> TYPE: PRT
<213> ORGANISM: Homo sapiens

<400> SEQUENCE: 112

Ala Leu Trp Glu Lys Glu Leu Gly Lys Lys Ile Lys Val
1               5                   10

<210> SEQ ID NO 113
<211> LENGTH: 18
<212> TYPE: PRT
<213> ORGANISM: Homo sapiens

<400> SEQUENCE: 113

Ala Cys Asp Ile Leu Asp Ser Thr Gly Gly Thr Asp Leu Thr Ala Gln
1               5                   10                  15

Leu Phe

<210> SEQ ID NO 114
<211> LENGTH: 15
<212> TYPE: PRT
<213> ORGANISM: Homo sapiens

<400> SEQUENCE: 114

Ala Leu Trp Glu Met Thr Gln Glu Leu Gly Lys Lys Ile Lys Val
1               5                   10                  15

<210> SEQ ID NO 115
<211> LENGTH: 20
<212> TYPE: PRT
<213> ORGANISM: Homo sapiens

<400> SEQUENCE: 115

Ala Cys Asp Thr Val Arg Asn Thr Gly Gly Tyr Ala Phe Ala Gly Ile
1               5                   10                  15

Asp Lys Leu Ile
            20

<210> SEQ ID NO 116
<211> LENGTH: 14
<212> TYPE: PRT
<213> ORGANISM: Homo sapiens

<400> SEQUENCE: 116

Ala Leu Trp Glu Pro Gln Glu Leu Gly Lys Lys Ile Lys Val
1               5                   10

<210> SEQ ID NO 117
<211> LENGTH: 17
<212> TYPE: PRT
<213> ORGANISM: Homo sapiens

<400> SEQUENCE: 117

Ala Cys Asp Lys Val Leu Gly Asp Ser Ser Trp Asp Thr Arg Gln Met
1               5                   10                  15

Phe

<210> SEQ ID NO 118
<211> LENGTH: 14
<212> TYPE: PRT
<213> ORGANISM: Homo sapiens

<400> SEQUENCE: 118

Ala Leu Trp Glu Ser Lys Glu Leu Gly Lys Lys Ile Lys Val
1               5                   10

<210> SEQ ID NO 119
<211> LENGTH: 18
<212> TYPE: PRT
<213> ORGANISM: Homo sapiens

<400> SEQUENCE: 119

Ala Cys Glu Gly Leu Gly Ala Thr Gln Ser Ser Trp Asp Thr Arg Gln
1               5                   10                  15

Met Phe

<210> SEQ ID NO 120
<211> LENGTH: 14
<212> TYPE: PRT
<213> ORGANISM: Homo sapiens

<400> SEQUENCE: 120

Ala Leu Trp Glu Val Gly Glu Leu Gly Lys Lys Ile Lys Val
1               5                   10

<210> SEQ ID NO 121
<211> LENGTH: 12
<212> TYPE: PRT
<213> ORGANISM: Homo sapiens

<400> SEQUENCE: 121

Ala Cys Asp Lys Leu Leu Gly Asp Asn Glu Leu Ile
1               5                   10

<210> SEQ ID NO 122
<211> LENGTH: 14
<212> TYPE: PRT
<213> ORGANISM: Homo sapiens

<400> SEQUENCE: 122

Ala Leu Trp Glu Val His Lys Leu Gly Lys Lys Ile Lys Val
1               5                   10

<210> SEQ ID NO 123
<211> LENGTH: 14
<212> TYPE: PRT
<213> ORGANISM: Homo sapiens

<400> SEQUENCE: 123

Ala Cys Asp Ser Leu Leu Gly Lys Gly Thr Asp Lys Leu Ile
1               5                   10

<210> SEQ ID NO 124
<211> LENGTH: 14
<212> TYPE: PRT
<213> ORGANISM: Homo sapiens

<400> SEQUENCE: 124

Ala Leu Trp Glu Val Lys Glu Leu Gly Lys Lys Ile Lys Val
1               5                   10

<210> SEQ ID NO 125
<211> LENGTH: 13
<212> TYPE: PRT
<213> ORGANISM: Homo sapiens

<400> SEQUENCE: 125

Ala Cys Asp Thr Leu Arg Gly Ser Ala Asp Lys Leu Ile
1               5                   10

<210> SEQ ID NO 126
<211> LENGTH: 16
<212> TYPE: PRT
<213> ORGANISM: Homo sapiens

<400> SEQUENCE: 126

Ala Leu Trp Glu Val Leu Gln Gln Glu Leu Gly Lys Lys Ile Lys Val
1               5                   10                  15

<210> SEQ ID NO 127
<211> LENGTH: 14
<212> TYPE: PRT
<213> ORGANISM: Homo sapiens

<400> SEQUENCE: 127

Ala Cys Asp Thr Val Pro Ala Arg His Thr Asp Lys Leu Ile
1               5                   10

<210> SEQ ID NO 128
<211> LENGTH: 14
<212> TYPE: PRT
<213> ORGANISM: Homo sapiens

<400> SEQUENCE: 128

Ala Leu Trp Glu Val Pro Val Leu Gly Lys Lys Ile Lys Val
1               5                   10

<210> SEQ ID NO 129
<211> LENGTH: 15
<212> TYPE: PRT
<213> ORGANISM: Homo sapiens

<400> SEQUENCE: 129

Ala Cys Asp Thr Ala Asp Arg Ser Ser Tyr Thr Asp Lys Leu Ile
1               5                   10                  15

<210> SEQ ID NO 130
<211> LENGTH: 19
<212> TYPE: PRT
<213> ORGANISM: Homo sapiens

<400> SEQUENCE: 130

Ala Cys Asp Thr Leu Leu Gly Asp Pro Ser Ser Ser Trp Asp Thr Arg
1               5                   10                  15

Gln Met Phe

<210> SEQ ID NO 131
<211> LENGTH: 16
<212> TYPE: PRT
<213> ORGANISM: Homo sapiens

<400> SEQUENCE: 131

Ala Cys Asp Thr Leu Ser Gly Gly Tyr Ala Arg Thr Asp Lys Leu Ile
1               5                   10                  15

<210> SEQ ID NO 132
<211> LENGTH: 16
<212> TYPE: PRT
<213> ORGANISM: Homo sapiens

<400> SEQUENCE: 132

Ala Cys Asp Thr Val Gly Ile Leu Gly Asp Thr Gly Leu Gly Leu Ile
1               5                   10                  15

<210> SEQ ID NO 133
<211> LENGTH: 16
<212> TYPE: PRT
<213> ORGANISM: Homo sapiens

<400> SEQUENCE: 133

Ala Cys Asp Thr Ile Val Ser Gly Tyr Asp Gly Tyr Asp Lys Leu Ile
1               5                   10                  15

<210> SEQ ID NO 134
<211> LENGTH: 14
<212> TYPE: PRT
<213> ORGANISM: Homo sapiens

<400> SEQUENCE: 134

Ala Cys Ser Ile Leu Gly Asp Lys Thr Ser Asp Lys Leu Ile
1               5                   10

<210> SEQ ID NO 135
<211> LENGTH: 15
<212> TYPE: PRT
<213> ORGANISM: Homo sapiens

<400> SEQUENCE: 135

Ala Leu Trp Glu Val Arg Gln Glu Leu Gly Lys Lys Ile Lys Val
1               5                   10                  15

<210> SEQ ID NO 136
<211> LENGTH: 16
<212> TYPE: PRT
<213> ORGANISM: Homo sapiens

<400> SEQUENCE: 136

Ala Cys Asp Thr Val Ser Gln Arg Gly Gly Tyr Ser Asp Lys Leu Ile
1               5                   10                  15

<210> SEQ ID NO 137
<211> LENGTH: 16
<212> TYPE: PRT
<213> ORGANISM: Homo sapiens

<400> SEQUENCE: 137

Ala Leu Trp Glu Val Arg Val Gln Glu Leu Gly Lys Lys Ile Lys Val
1               5                   10                  15

<210> SEQ ID NO 138
<211> LENGTH: 18
<212> TYPE: PRT
<213> ORGANISM: Homo sapiens

<400> SEQUENCE: 138

Ala Cys Asp Pro Leu Glu Arg Val Gly Gly Pro Ala Asn Thr Asp Lys
1               5                   10                  15

Leu Ile

<210> SEQ ID NO 139
<211> LENGTH: 14
<212> TYPE: PRT
<213> ORGANISM: Homo sapiens

<400> SEQUENCE: 139

Ala Leu Trp Glu Val Thr Glu Leu Gly Lys Lys Ile Lys Val
1               5                   10

<210> SEQ ID NO 140
<211> LENGTH: 14
<212> TYPE: PRT
<213> ORGANISM: Homo sapiens

<400> SEQUENCE: 140

Ala Cys Asp Val Leu Gly Asp Thr Gly Asp Lys Leu Ile
1               5                   10

<210> SEQ ID NO 141
<211> LENGTH: 13
<212> TYPE: PRT
<213> ORGANISM: Homo sapiens

<400> SEQUENCE: 141

Ala Leu Trp Gly Arg Glu Leu Gly Lys Lys Ile Lys Val
1               5                   10

<210> SEQ ID NO 142
<211> LENGTH: 13
<212> TYPE: PRT
<213> ORGANISM: Homo sapiens

<400> SEQUENCE: 142

Ala Cys Asp Thr Val Gly Ser Asn Thr Asp Lys Leu Ile
1               5                   10

<210> SEQ ID NO 143
<211> LENGTH: 14
<212> TYPE: PRT
<213> ORGANISM: Homo sapiens

<400> SEQUENCE: 143

Ala Cys Asp Val Leu Gly Asp Thr Glu Ala Asp Lys Leu Ile
1               5                   10

<210> SEQ ID NO 144
<211> LENGTH: 17
<212> TYPE: PRT
<213> ORGANISM: Homo sapiens

<400> SEQUENCE: 144

Ala Leu Tyr Gly Ser Pro Ser Gly Glu Glu Leu Gly Lys Lys Asn Gln
1               5                   10                  15

Gly

<210> SEQ ID NO 145
<211> LENGTH: 17
<212> TYPE: PRT
<213> ORGANISM: Homo sapiens

<400> SEQUENCE: 145

Ala Cys Asp Pro Leu Glu Gly Ala Gly Gly His Asn Thr Asp Lys Leu
1               5                   10                  15

Ile

<210> SEQ ID NO 146
<211> LENGTH: 9
<212> TYPE: PRT
<213> ORGANISM: Influenza virus

<400> SEQUENCE: 146

Gly Ile Leu Gly Phe Val Phe Thr Leu
1               5

<210> SEQ ID NO 147
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
gcagctggag caaactg                                                      17

<210> SEQ ID NO 148
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
ctgaattatc ggtcaccag                                                    19

<210> SEQ ID NO 149
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
caaatatcct gtaaagtttt catc                                              24

<210> SEQ ID NO 150

```
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
gtttagagtt tctattatat gtccttgcaa c                                      31

<210> SEQ ID NO 151
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
gatatctcag gatcagctct cc                                                22

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
tacccgaaga ccaaacaaga c                                                 21

<210> SEQ ID NO 153
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
tcacctctgg ggtcatatg                                                    19

<210> SEQ ID NO 154
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
agaggaaagg aaatacggc                                                    19

<210> SEQ ID NO 155
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
caacttggaa gaaagaataa tgtc                                              24

<210> SEQ ID NO 156
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
caccaagcta gaggggtc                                                   18

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
cttttctttc caatacaccc                                                 20

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
tcdggaaaga acttttcaag g                                               21

<210> SEQ ID NO 159
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
acccaaatgt tgcatcag                                                   18

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
gtctctgaca atccaagaag g                                               21

<210> SEQ ID NO 161
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
tctgtgcagg tggcag                                                     16

<210> SEQ ID NO 162
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 162
ccctggactg cacctatg                                                 18

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
tgtatatttg gaaccagttg c                                             21

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
gatcctgcct ccttctactg                                               20

<210> SEQ ID NO 165
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
catcacgctg acccag                                                   16

<210> SEQ ID NO 166
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
gctccactga ccagacag                                                 18

<210> SEQ ID NO 167
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
cascttytta gtggagagat gg                                            22

<210> SEQ ID NO 168
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 168
aytctgtagt cttccagaaa tcac                                            24

<210> SEQ ID NO 169
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
tccttggttc tgcagg                                                     16

<210> SEQ ID NO 170
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
tgcaggaggg ggaga                                                      15

<210> SEQ ID NO 171
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
gcagcaggtg agacaaag                                                   18

<210> SEQ ID NO 172
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
ctctgacagt ctgggaagg                                                  19

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
cagatgcaag gtcaagtgac                                                 20

<210> SEQ ID NO 174
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 174
ggagaaggtc cacagctc                                                 18

<210> SEQ ID NO 175
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
aaggtccaca gctccttc                                                 18

<210> SEQ ID NO 176
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
caactgccaa caacaagg                                                 18

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
gttctggtat gtgcagtatc c                                             21

<210> SEQ ID NO 178
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
tccttccact tgcagaaag                                                19

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
tctgstctga gatgcaattt t                                             21

<210> SEQ ID NO 180
<211> LENGTH: 22
<212> TYPE: DNA
<213> ORGANISM: Artificial Sequence
<220> FEATURE:
<223> OTHER INFORMATION: Description of Artificial Sequence: Synthetic
```

```
        primer
<220> FEATURE:
<221> NAME/KEY: modified_base
<222> LOCATION: (3)..(3)
<223> OTHER INFORMATION: Inosine
<220> FEATURE:
<221> NAME/KEY: modified_base
<222> LOCATION: (5)..(5)
<223> OTHER INFORMATION: Inosine

<400> SEQUENCE: 180
ggntnmagga acaaaggaga at                                                   22

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
gtacaagcaa acagcaagtg                                                      20

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
attattctct gaactttcag aagc                                                 24

<210> SEQ ID NO 183
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
gtgcacttgc cttgtagc                                                        18

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
aatagtatgg ctttcctggc                                                      20

<210> SEQ ID NO 185
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
tgaaagaatt ttgcatatgg ttc                                                  23
```

```
<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
gagatgacta tagcagggtc g                                              21

<210> SEQ ID NO 187
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
taccacgtgg tcaagctg                                                  18

<210> SEQ ID NO 188
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
ggggttgtcc agtctcc                                                   17

<210> SEQ ID NO 189
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
gctgcagtca cccaaag                                                   17

<210> SEQ ID NO 190
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
cctaggcaca aggtgacag                                                 19

<210> SEQ ID NO 191
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
gcagtcctac aggaaggg                                                  18
```

```
<210> SEQ ID NO 192
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
gagttaccca gacacccag                                              19

<210> SEQ ID NO 193
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
gaagccaaac caagcac                                                17

<210> SEQ ID NO 194
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
gattggtcag gaagggc                                                17

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
catctactgg taccgacagg                                             20

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
cagtatctag gccacaatgc                                             20

<210> SEQ ID NO 197
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
ggatggagtg tcaagctg                                               18

<210> SEQ ID NO 198
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
ctgcagttac acagaagcc                                                      19

<210> SEQ ID NO 199
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
cagactccac gatacctgg                                                      19

<210> SEQ ID NO 200
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
gctggaatgt ggacagg                                                        17

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
cccaaagtct tacagatccc                                                     20

<210> SEQ ID NO 202
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
ctaacctcta ctggtactgg cag                                                 23

<210> SEQ ID NO 203
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
gacggctgtt ttccagac                                                       18

<210> SEQ ID NO 204
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
ggtataaaca gagcgctgag                                              20

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
ccagaaggta gcagagaccc                                              20

<210> SEQ ID NO 206
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
gtatccctgg atgagctg                                                18

<210> SEQ ID NO 207
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
ccagcagatt ctcagtcc                                                18

<210> SEQ ID NO 208
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
gtactggtat cggcaggac                                               19

<210> SEQ ID NO 209
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
ggtatcagca gcccagag                                                18

<210> SEQ ID NO 210
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 210
gtgtgagcca gtttcagg                                                  18

<210> SEQ ID NO 211
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
gaagcaactc tgtggtgtg                                                 19

<210> SEQ ID NO 212
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
gaacagggaa gctgacac                                                  18

<210> SEQ ID NO 213
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
ggtaccgaca ggattcag                                                  18

<210> SEQ ID NO 214
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
ggacaatcag actgcctc                                                  18

<210> SEQ ID NO 215
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
gcttggtatc gtcaatcg                                                  18

<210> SEQ ID NO 216
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 216
gccaggaagc agagatg                                                    17

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
gaggtgtatc cctgaaaagg                                                 20

<210> SEQ ID NO 218
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
gcacactgcc ttttactgg                                                  19

<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
gtactggtat cgacaagacc c                                               21

<210> SEQ ID NO 220
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
gatatggggc agatggtg                                                   18

<210> SEQ ID NO 221
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
ctgttggcca ggtagagtc                                                  19

<210> SEQ ID NO 222
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 222
gccagagctc atgtttctc                                                  19

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
gggtagcctt ttgtttgttt g                                               21

<210> SEQ ID NO 224
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
ctacactgag tgttcgagag g                                               21

<210> SEQ ID NO 225
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
ggttccacgc cactc                                                      15

<210> SEQ ID NO 226
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
tatgaaggag cctccctg                                                   18

<210> SEQ ID NO 227
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
caagatttca ccgcacg                                                    17

<210> SEQ ID NO 228
<211> LENGTH: 19
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 228
gctgactgtt caagaggga                                               19

<210> SEQ ID NO 229
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
ctccacattc ctgagcc                                                 17

<210> SEQ ID NO 230
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
actctgagcc tgccct                                                  16

<210> SEQ ID NO 231
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
acggctggcc agaag                                                   15

<210> SEQ ID NO 232
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
agagccaccc ttgacac                                                 17

<210> SEQ ID NO 233
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
gcttygaggc tgagttcag                                               19

<210> SEQ ID NO 234
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
gcacattgat ttgggagtc                                                19

<210> SEQ ID NO 235
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
agagaaggtc gagcaacac                                                19

<210> SEQ ID NO 236
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
aagacccaag tggagcag                                                 18

<210> SEQ ID NO 237
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
tgacccagac agaaggc                                                  17

<210> SEQ ID NO 238
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
gcaagttaaa caaagctctc c                                             21

<210> SEQ ID NO 239
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
cagtccgtgg accagc                                                   16

<210> SEQ ID NO 240
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 240
aacggctgga gcagag                                                    16

<210> SEQ ID NO 241
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
ggcgagcagg tggag                                                     15

<210> SEQ ID NO 242
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
ggctacttcc cttggtataa gcaaga                                         26

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
agattccgtg actcaaacag                                                20

<210> SEQ ID NO 244
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
agaaggtrca gcagagccca gaatc                                          25

<210> SEQ ID NO 245
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
gagcrtccas gagggtg                                                   17

<210> SEQ ID NO 246
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
```
ccagtggttc aaggagtg                                                    18

<210> SEQ ID NO 247
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
ggcatcacag ggaacg                                                      16

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
atctcaccat aaactgcacg                                                  20

<210> SEQ ID NO 249
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
gcacccacat ttctktctta c                                                21

<210> SEQ ID NO 250
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
gaaagaactg cactcttcaa tg                                               22

<210> SEQ ID NO 251
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
aagatggaag gtttacagca c                                                21

<210> SEQ ID NO 252
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252

```
tcagacagtg cctcaaacta c                                              21
```

<210> SEQ ID NO 253
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253

```
cagtgaaaca tctctctctg c                                              21
```

<210> SEQ ID NO 254
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254

```
aggctgtgac tctggactg                                                 19
```

<210> SEQ ID NO 255
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255

```
gtccagtact ccagacaacg                                                20
```

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256

```
ccaccatgaa ctgcagttac                                                20
```

<210> SEQ ID NO 257
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257

```
tgacagttcc ttccacctg                                                 19
```

<210> SEQ ID NO 258
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258

```
tgtgaccttg gactgtgtg                                                 19
```

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
cactctgtgt ccaatgctta c                                         21

<210> SEQ ID NO 260
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
tctggtatag gcaagatcct g                                         21

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
aacttggttc tcaactgcag                                           20

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
ctgactctgt gaacaatttg c                                         21

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
aatcttcaca tcaattccct g                                         21

<210> SEQ ID NO 264
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
tgcattattg atagccatac g                                         21

```
<210> SEQ ID NO 265
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
tgccttacac tggtacagat g                                              21

<210> SEQ ID NO 266
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
tataagcaaa ggcctggtg                                                 19

<210> SEQ ID NO 267
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
cgacagattc actcccag                                                  18

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
ttcacttgcc ttgtaaccac                                                20

<210> SEQ ID NO 269
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
ctcactgtgt actgcaactc c                                              21

<210> SEQ ID NO 270
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
atgcacctat tcagtctctg g                                              21
```

```
<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
agagtgaaac ctccttccac                                                    20

<210> SEQ ID NO 272
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
agaagcatgg tgaagcac                                                      18

<210> SEQ ID NO 273
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
acctggctat ggtacaagc                                                     19

<210> SEQ ID NO 274
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
cagcaggcag atgattctc                                                     19

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
tcaaccactt cagacagact g                                                  21

<210> SEQ ID NO 276
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
attatatcac gtggtaccaa cag                                                23

<210> SEQ ID NO 277
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
ggaggcggaa atattaaaga c                                              21

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
ttgtttatgc tgagctcagg                                                20

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
tacacagaca gctcctccac                                                20

<210> SEQ ID NO 280
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
tggtaccgac aagatccag                                                 19

<210> SEQ ID NO 281
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
tatgagaagc agaaaggaag ac                                             22

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
gtcaacacct tcagcttctc                                                20

<210> SEQ ID NO 283
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
atcagaggtt ttgaggctg                                                   19

<210> SEQ ID NO 284
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
aaccaaggac tccagcttc                                                   19

<210> SEQ ID NO 285
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
tttgaggctg aatttaagag g                                                21

<210> SEQ ID NO 286
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
gaaaccactt ctttccactt g                                                21

<210> SEQ ID NO 287
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
tgttgctctt gaagtccata g                                                21

<210> SEQ ID NO 288
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
tggtatcgac aagacctgg                                                   19

<210> SEQ ID NO 289
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 289
ggaacaccag tgactctgag                                            20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
gactccactc tcaagatcca                                            20

<210> SEQ ID NO 291
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
cyactctgar gatccagcc                                             19

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292
cattctgaac tgaacatgag c                                          21

<210> SEQ ID NO 293
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
cttggagctg grsgactc                                              18

<210> SEQ ID NO 294
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
attctactct gaaggtgcag c                                          21

<210> SEQ ID NO 295
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 295
ataacttcca atccaggagg                                                    20

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
ctgtagcctt gagatccagg                                                    20

<210> SEQ ID NO 297
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
tgttcactgg taccgacag                                                     19

<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
cgattttctg ctgaatttcc                                                    20

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
ttcctctcac tgtgacatcg                                                    20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
ttcactctga agatccggtc                                                    20

<210> SEQ ID NO 301
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 301
actctgacag tgaccagtgc                                                 20

<210> SEQ ID NO 302
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
gcaatcctgt cctcagaac                                                  19

<210> SEQ ID NO 303
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
gatggataca gtgtctctcg a                                               21

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
cagagaaggg agatctttcc                                                 20

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
ttcyccctga tyctggagtc                                                 20

<210> SEQ ID NO 306
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
tctgactgtg agcaacatga g                                               21

<210> SEQ ID NO 307
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 307
agaatctctc agcctccaga c                                              21

<210> SEQ ID NO 308
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
cctgcagcca gaagactc                                                  18

<210> SEQ ID NO 309
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
tctgagctga atgtgaacg                                                 19

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
gtgtrcccag gatatgaacc                                                20

<210> SEQ ID NO 311
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
tggttatagt gtctccagag c                                              21

<210> SEQ ID NO 312
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
tcyactctga mgwtccagcg                                                20

<210> SEQ ID NO 313
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 313
gtaccaacag agcctggac                                                    19

<210> SEQ ID NO 314
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
ttctgatggc tcaaacacag                                                   20

<210> SEQ ID NO 315
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
atycgttcaa atatggaaag aaa                                               23
```

CLONING AND EXPRESSION SYSTEM FOR T-CELL RECEPTORS

CROSS REFERENCE TO RELATED APPLICATIONS

This application is a U.S. National Phase of International Patent Application No. PCT/US2016/064735, filed on Dec. 2, 2016, which published as WO 2017/096239 A1 on Jun. 8, 2017, and claims priority to U.S. Provisional Patent Application Ser. No. 62/263,318, filed on Dec. 4, 2015, all of which are herein incorporated by reference in their entirety.

STATEMENT AS TO FEDERALLY SPONSORED RESEARCH

The invention was made with government support under grant AI107625 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 30, 2016, is named 243734_000082_SL.TXT and is 76,261 bytes in size.

FIELD OF THE INVENTION

The invention is directed to methods for rapid cloning and expression of T-cell receptors (TCRs) and B-cell receptors (BCRs) and their use for drug screening, structural and functional studies and other applications. More particularly, the invention provides a method for rapid cloning of TCRs (e.g., paired αβ and γδ TCR chains) or BCRs (e.g., paired IgH or Igκ or Igλ) from single cells by CDR3 substitution using single cell PCR products and Gibson Assembly techniques and a pre-generated TCR (or BCR) library in an expression vector.

BACKGROUND OF THE INVENTION

T cells play a vital role in the control of viral infections and tumors. T cells are activated by antigen presenting cells via interactions between peptide-major histocompatibility complex (pMHC) and TCRs. This interaction can induce proliferation and the development of effector functions, including cytokine production and cytotoxic activity. T cells can also infiltrate infected or transformed tissues, e.g. as tumor-infiltrating lymphocytes (TILs), to perform these effector functions[1,2]. However, in some chronic viral infections and tumors, responding effector T cells progressively get exhausted and become dysfunctional[3,4,5]. In addition, control of tumors and/or infection may require large numbers of highly reactive lymphocytes that cannot be achieved due to normal tolerance mechanisms. One effective method to overcome this barrier is the use of therapeutic adoptive transfer of lymphocytes[2,6,7].

Adoptive transfer of lymphocytes such as in vitro expanded or TCR-engineered antigen specific T cells has been successfully used to control viruses and tumors in patients[8,9,10,11,12]. In vitro expansion of viral or tumor-specific T cells require significant time to prepare and the targets are not usually fully characterized. Lymphocytes expressing engineered TCRs and chimeric antigen receptors (CAR) target specific antigens, with CARs recognizing surface antigens through immunoglobulin-type interactions[10,13] and TCRs recognizing tumor-associated pMHC complexes. CAR therapy directed against surface antigens requires a tumor-associated antigen that can be universally targeted (even on healthy, non-tumor tissue) without significant toxicity. Tumor-specific antigens that are targeted by TCRs represent an attractive alternative that can provide greater specificity and reduce non-tumor associated toxicities[14,15,16]. Additionally, engineered T cells expressing high-affinity antigen receptors can be conditioned to overcome immune tolerance, which has been a major limitation for immunotherapy[14,15,17]. Apart from the clinical applications, a robust system for the cloning and expression of TCRs is a valuable tool for the investigation of TCR structure and functions[18,19,20].

Techniques to rapidly profile and clone antigen-specific TCRs have improved and shortened the process of TCR-engineered immunotherapy[21,22]. These approaches are useful contributions to the field and are able to handle large cell inputs very effectively. However, for certain applications, the reported methods still have some limitations. First, approaches that rely on deep sequencing and cloning of bulk sorted cells can still be limited by target cell numbers. In contrast, single cell approaches can utilize input sizes starting with a single cell but are less efficient at dealing with high cell number inputs (greater than 10,000 cells). As a result, single cell methods are best directed at defined samples such as antigen-specific responses or tissue-associated infiltrating cells. Second, for bulk sorting, pairing of TCR chains requires algorithmic imputation, which can have difficulty dealing with cells expressing two distinct TCR chains of one type (e.g. two TCRα chains), which are quite common. A recently reported algorithm has addressed this concern by pairing bulk processed TCRs using barcoded pools of cells [23]. However, this method requires relatively large inputs to successfully pair and would likely not be appropriate for very small sample sizes as might be obtained from tissue biopsies or tetramer sorting of small populations.

Third, while currently reported methods are able to generate full length receptors either by synthesis or by 5' RACE-associated approaches at the single cell level, these methods require expansion of the isolated cells prior to TCR isolation, which likely causes bias in the TCR repertoire in the subsequent analyses and/or can reduce efficiency. Lastly, the majority of antiviral and antitumor adoptive therapy has focused on αβ T cell clones due to their exquisite antigen specificity. However, γδ cells have also been shown to mediate antiviral and antitumor effects and are novel candidates for therapeutic development[24,25].

SUMMARY OF THE INVENTION

To date, there is little research about profiling and utilizing the TCRγδ repertoire for therapeutic purposes. Applying γδ T cells for immunotherapeutic applications may be a promising future approach in conjunction with traditional TCRαβ techniques. Therefore, it is important to establish a system to define the repertoire and functional activity for γδ T cells. Additionally, improving efficiencies for cloning αβ TCRs from single cells may have complementary uses in the lab and in the clinic.

There is a great need in the art to develop a rapid, efficient and accurate cloning and expression method and/or system for specific TCRs, and uses thereof for screening TCR-mediated therapeutics, as well as for other research and/or clinical applications. The present invention fulfils such needs, and provides such methods and platforms.

In one aspect, the invention provides a method for cloning a T cell receptor (TCR) from a single T cell, wherein said method comprises:
(a) performing RT-PCR with a primer mixture on a single T cell to obtain paired αβ or γδ TCR CDR3 DNA sequences comprising a partial variable (V) region, CDR3 region, and a partial constant (C) region,
(b) optionally sequencing the RT-PCR product obtained in step (a), and
(c) cloning the αβ or γδ TCR CDR3 DNA sequences obtained in step (a) into a corresponding TCRαβ or TCRγδ library.

In one embodiment, said T cell is a human or a mouse αβ or γδ T cell.

In one embodiment, the method comprises sorting of single T cells prior to step (a). In one specific embodiment, T cells are not stimulated prior to sorting.

In one embodiment, the primer mixture comprises sense primers comprising T-cell receptor gamma variable (TRGV) sequences and/or T cell receptor delta variable (TRDV) sequences and antisense primers comprising T-cell receptor gamma constant (TRGC) sequences and/or T-cell receptor delta constant (TRDC) sequences. In one specific embodiment, the primer mixture comprises 9 TRGV and 8 TRDV sense primers and single TRGC and TRDC antisense primers. In another specific embodiment, the primer mixture comprises 5 external and 5 internal TRGV and 13 external and 13 internal TRDV sense primers and single TRGC and TRDC antisense primers. In one embodiment, the TRGV and/or TRDV sense primers and the TRGC and/or TRDC antisense primers are selected from the primers listed in Table 1. In one embodiment, the TRGV and/or TRDV sense primers and the TRGC and/or TRDC antisense primers are selected from the primers listed in Table 6.

In one embodiment, the single cell RT-PCR of γδ or αβ TCR and sequencing are performed within not more than 2 days.

In one embodiment, the method further comprises cloning the resulting αβ or γδ TCR CDR3 DNA sequences into the TCRαβ and/or TCRγδ library constructed using the method described below.

In a related aspect, the invention provides a method for constructing a TCRαβ and/or TCRγδ library in an expression vector, comprising:
(a) synthesizing multiple pairs of TRGV and TRDV DNA fragments or TRAV and TRBV DNA fragments with a 15-25 bp overlap to the vector sequence based on the amplified sequence of the TRGV/TRDV or TRAV/TRBV pairings, respectively, and
(b) performing a two- or three-way ligation with a linearized expression vector.

In one embodiment of the above library construction method, the expression vector is a retroviral or lentiviral expression vector. In one embodiment, the ligation in step (b) is performed using Gibson Assembly Cloning techniques. In one specific embodiment, Gibson Assembly Cloning techniques are optimized to clone synthesized TRGV/TRAV and TRDV/TRBV DNA fragments using g-blocks or other synthesized DNA fragments (e.g., long primers that are then annealed). In one embodiment, the TCRαβ and/or TCRγδ library is constructed after a single-cell amplification and synthesized paired TRGV/TRDV or TRAV/TRBV receptors based on the sequence data. In one embodiment, the TCRαβ and/or TCRγδ library is constructed in 5 to 10 days. In one embodiment, the TCRαβ and/or TCRγδ library is used for drug screening or identification of TCRαβ- and/or TCRγδ-specific ligands.

In one embodiment of the above library construction, the method comprises substituting CDR3 regions of the existing clones in the TCRαβ and/or TCRγδ library with (i) products of RT-PCR performed using a primer mixture on a single T cell to obtain paired αβ or γδ TCR CDR3 DNA sequences comprising a partial variable (V) region, CDR3 region, and a partial constant (C) region and (ii) a linker DNA for overlap extension of PCR cloning. In one specific embodiment, said T cell is a human or a mouse αβ or γδ T cell. In one specific embodiment, the method comprises sorting of single T cells prior to RT-PCR. In one specific embodiment, T cells are not stimulated prior to sorting. In one specific embodiment, the primer mixture comprises sense primers comprising T-cell receptor gamma variable (TRGV) and/or T cell receptor delta variable (TRDV) and antisense primers comprising T-cell receptor gamma constant (TRGC) and/or T-cell receptor delta constant (TRDC) sequences. In one specific embodiment, the primer mixture comprises 9 TRGV and 8 TRDV sense primers and single TRGC and TRDC antisense primers. In one specific embodiment, the primer mixture comprises 5 external and 5 internal TRGV and 13 external and 13 internal TRDV sense primers and single TRGC and TRDC antisense primers. In one specific embodiment, the TRGV and/or TRDV sense primers and the TRGC and/or TRDC antisense primers are selected from the primers listed in Table 1. In one specific embodiment, the TRGV and/or TRDV sense primers and the TRGC and/or TRDC antisense primers are selected from the primers listed in Table 6. In one specific embodiment, said linkers are overlapping with the non-variant sequences of the TCRα/γ and TCRβ/δ single cell RT-PCR products. In one specific embodiment, said linker sequences are selected from those listed in Table 3. In one specific embodiment, the resulting TCRαβ and/or TCRγδ chains with CDR3 substitutions are used for T cell-mediated immunotherapy.

In a related aspect, the invention provides a TCRαβ and/or TCRγδ library constructed using any of the above methods. In another related aspect, the invention provides a host cell (e.g., a Nur-77-GFP Jurkat 76 cell or a Nur-77-Luciferase Jurkat 76 cell) comprising said TCRαβ and/or TCRγδ library construct.

In another aspect, the invention provides a method for cloning a B cell receptor (BCR) from a single B cell, wherein said method comprises:
(a) performing RT-PCR with a primer mixture on a single B cell to obtain paired IgH or Igκ or Igλ CDR3 DNA sequences comprising a partial variable (V) region, CDR3 region, and a partial constant (C) region,
(b) optionally sequencing the RT-PCR product obtained in step (a), and
(c) cloning the IgH or Igκ or Igλ CDR3 DNA sequences obtained in step (a) into a corresponding BCR library.

In one embodiment, said B cell is a human or a mouse B cell. In one embodiment, the method comprises sorting of single B cells prior to step (a).

These and other aspects of the present invention will be apparent to those of ordinary skill in the art in the following description, claims and drawings.

BRIEF DESCRIPTION OF THE DRAWINGS

FIG. 2A shows a schematic of rapid cloning and expression of human TCRαβ or TCRγδ in a retroviral vector. A schematic diagram of TCR cloning using gBlock® synthesized DNA fragments and a linearized retroviral vector (pMICherry) is shown. Family specific TRGV and TRDV full length TCR chains were synthesized with a 15-20 bp overlap sequence (light diagonal line shading) in the 2A region. Together with a linearized pMICherry expression vector, a three-way ligation is performed by using Gibson Assembly® Cloning. The timeline of this process is presented on the left.

FIG. 2B shows expression of TCR constructs in the Jurkat 76 TCRα⁻β⁻ cell line. The vectors with human TRGV9/TRDV2 TCR genes and human influenza-specific TCRαβ genes were co-transfected with the human CD3 construct into the Jurkat 76 TCRα⁻β⁻ cell line. The flow cytometry results of transfected cells are shown.

FIGS. 5A and 5B depict the time lines of the two cloning platforms.

FIGS. 6A and 6B show a comparison of single transfection of human TCR constructs and co-transfection of human TCR constructs and human CD3. FIG. 6C shows quantification of mCherry/ametrine and TCR/CD3 expression is shown. Statistical differences were determined by One-way ANOVA; $p<0.05$ was considered statistically significant. Data are mean±SEM of two independent experiments. *$p<0.001$, **$p<0.0001$.

DETAILED DESCRIPTION OF THE INVENTION

Figure 1A:
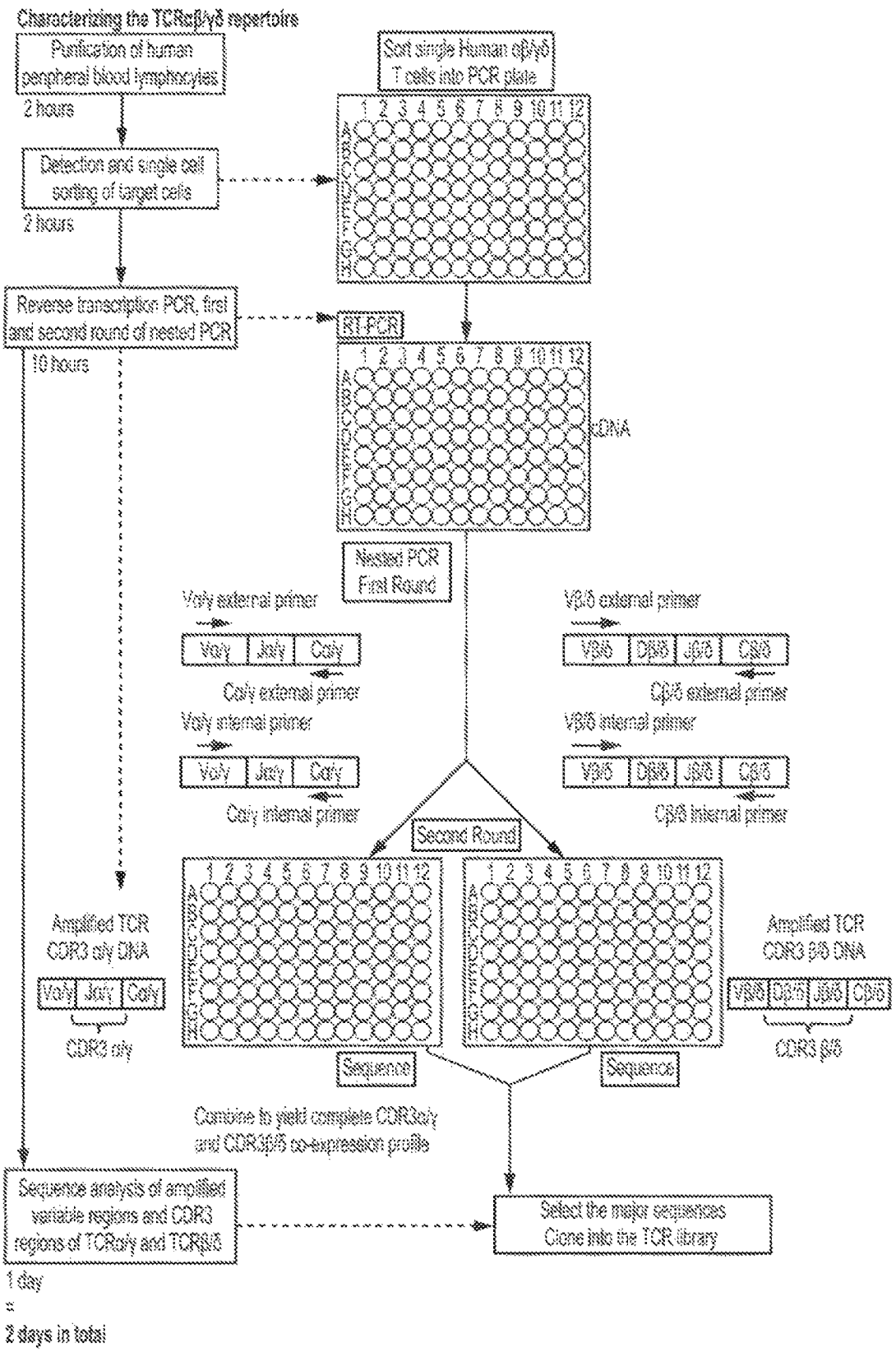
FIG. 1A shows a schematic of unbiased single-cell amplification of paired TCR CDR3 regions. Overview of the multiplex PCR protocol to amplify and sequence paired TCR CDR3 α/γ and CDR3 β/δ. After sorting single human αβ or γδ T cells into a 96-well plate, reverse transcription is performed to obtain single-cell cDNA. Taking human γδ T cells as an example, a first round of PCR is performed by using an external primer mixture of 9 TRGV and 8 TRDV sense and single TRGC and TRDC antisense primers following RT-PCR. The first-round PCR products are subjected to two separate second-round PCRs using a corresponding internal primers mix (9 sense TRGV, single antisense TRGC, and 8 sense TRDV, single antisense TRDC, respectively). The timeline of this process is shown on the left.

The present invention provides a rapid, efficient and accurate cloning and expression method and system for specific TCRs (e.g., paired αβ and γδ TCR chains from single cells) which can be used for drug screening (e.g., for T cell-mediated anti-tumor or anti-infective immunotherapy), for structuring and functional analysis of TCRs, and other applications. The invention addresses the non-specific, labor-intensive and time-consuming issues of prior PCR-based cloning methods and provides a high-throughput, accurate and efficient method of TCR engineering for therapeutic and research applications.

In conjunction with single cell multiplex PCR techniques for TCRαβ or TCRγδ profiling[26,27], and Gibson Assembly® cloning of synthesized DNA, the invention provides rapid sequencing and cloning of specific TCRs in an expression vector (e.g., retroviral expression vector). By generating TCR libraries, the invention provides a cloning and expression method and system that is significantly accelerated by only requiring the substitution of the CDR3 region, resulting in TCR clones in appropriate expression vectors in as little as five days after cell isolation. The invention provides highly robust, inexpensive, efficient, and high-throughput means for TCR engineering for therapeutic and research applications.

In certain embodiments, the invention provides a method of single-cell amplification of paired TCR CDR3 α/γ and CDR3 β/δ regions comprising the steps of (a) sorting of single human αβ or γδ T cells; (b) performing RT-PCR to obtain a single-cell cDNA; and (c) amplifying the single-cell cDNA obtained in step (b) in a second round PCR with a primer mixture of TRGV and TRDV sense primers and TRGC and TRDC antisense primers. In one embodiment, the single-cell cDNAs are amplified with a primer mixture comprising nine (9) T-cell receptor gamma variable (TRGV) and/or eight (8) T-cell receptor delta variable (TRDV) sense primers and a single T-cell receptor gamma constant (TRGC) and/or T-cell receptor delta constant (TRDC) antisense primer. Non-limiting examples of external and internal sense primers targeting TRGV and TRDV and antisense TRGC and TRDC primers are listed in Table 1, below. Specific non-limiting examples of a method for sorting single cells, as well as conditions for RT-PCR and nested PCRs, are provided below (see Example 1, Materials & Methods).

In certain embodiments, the invention also provides a method of production of TCRαβ and TCRγδ library in an expression vector, comprising the steps of (a) synthesizing multiple pairs of TRGV and TRDV DNA fragments with a 15-20 bp overlap in the sequence in the 2A region based on the TRGV/TRDV usage in human apheresis ring samples, and (b) performing a three-way ligation with a linearized expression vector (e.g., a retroviral vector, which is convenient for the future applications, like transduction of cell lines and TCR-transgenic mice) using Gibson Assembly® Cloning or another type of ligation, including, e.g., conventional T4-mediated ligation. In certain embodiments, the TCRαβ and/or TCRγδ library is human library comprising the human TCRαβ and TCRγδ. In certain embodiments, the production of TCRαβ and TCRγδ library is performed after the single-cell amplification and paired TRGV/TRDV usage based on the sequence data. Exemplary primers targeting the 2A regions of human CD3δ, γ, ε and genes are provided in Tables 2A & 2B.

The Gibson Assembly kit is an enzyme and buffer mix designed to optimize the overlap ligation of g-block gene fragments. In certain embodiments, Gibson Assembly protocol is optimized to synthesize the TRGV and TRDV DNA fragments or genes using g-block technique, IDT DNA). However, the ligation reaction can be performed using other suitable ligases known and available in the art. Using the methods of the present invention, a TCR library can be constructed in as fast as 10 days. As long as the library is established, it can be applied to substitute CDR3 regions from a new patient sample, which can dramatically reduce the cloning time from 10 days to 5 days. This could be beneficial for both adoptive transfer therapy and personalized therapy.

The invention provides a rapid cloning method based on the TCR library constructed, e.g., the TCRαβ and TCRγδ library, comprising the step of generating full-length paired αβ or γδ TCR chains by CDR3 substitution using multiplex PCR products and a linker DNA (overlap extension PCR). In certain embodiments, the linkers contribute to simultaneously substitute CDR3 regions of both TCRα/γ and TCRβ/δ. The linkers are overlapping with the single cell PCR products, therefore, no additional PCR steps are needed. In certain embodiments, the TCRα/γ and TCRβ/δ single cell PCR products and the linkers are mixed together and an overlap PCRs are performed, and then the PCR products generated from the overlap PCRs are used to substitute the CDR3 regions in the cloning library. Exemplary human TCRγδ linker sequences are provided in Table 3, below.

The methods of the present inventions improve the speed and specificity for cloning paired TCRs. With single cell analyses, the cloned paired TCRs of the present invention are more "specific" than examining T cell receptors in bulk because both chains of the receptor are from the same cell. The invention allows rapid cloning of TCRs that are responding to an infection or a tumor, which could be useful in developing targeted cell therapies, e.g., by reintroducing those receptors into the patient's cells to assist in mounting a more effective response. The TCR sequences themselves can also be useful for understanding what targets the response is against. Although there is no simple way of decoding the target from the TCR sequence, databases and/or computer algorithms can be developed to evaluate the relationship on the antigens and the elicited T-cell responses via various TCRs. Furthermore, the invention provides an efficient and accurate TCR expression system for TCRs in a reporter cell line, which can be used for screening specific antigens directly. TCR sequencing can also be used for the detection of minimal residual disease in leukemia and lymphoma. Many tumors have rearranged their TCRs. In these cases, the specific TCR sequence in the tumor becomes a lineage "barcode" for the tumor itself. The methods of the invention can provide TCR sequencing information to determine the presence and/or quantity of tumor cells.

Definitions

In describing the present invention, the following terms will be employed, and are intended to be defined as indicated below.

"CDR3 region" or "the third complementarity determining region" is defined herein as the region from codon positions 105 to the end of the V-REGION in germline gDNA or cDNA, codon positions 105 to 117 in V-DOMAIN of rearranged gDNA or in cDNA (all the position numbers are according to the IMGT unique numbering; see Lefranc, M.-P., The Immunologist, 7, 132-136 (1999) and www.imgt.org/IMGTScientificChart/Nomenclature/IMGT-FRCDRdefinition.html).

As used herein the term "partial variable region" or "partial V region" is determined by the position of the internal forward primers targeting the amplified V-region of interest (e.g., α, β, γ, δ; see, e.g., Tables 8-11) until the codon position 105 (all the position numbers are according to the IMGT unique numbering; see Lefranc, M.-P., The Immunologist, 7, 132-136 (1999) and www.imgt.org/IMGTScientificChart/Nomenclature/IMGT-FRCDRdefinition.html).

As used herein the term "partial constant region" or "partial C region" refers to a region that includes the first codon of the C region until a position defined by the reverse internal primer used to amplify the C region of interest (e.g., α, β, γ, δ; see Tables 8-11).

The term "corresponding TCR library" means the same variable (V) family usage.

It must be noted that, as used in this specification and the appended claims, the singular forms "a," "an" and "the" include plural referents unless the content clearly dictates otherwise.

The terms "subject," "individual," and "patient," are used interchangeably herein and refer to any mammalian subject for whom diagnosis, prognosis, treatment, or therapy is desired, particularly humans. Other subjects may include cattle, dogs, cats, guinea pigs, rabbits, rats, mice, horses, and so on. In some cases, the methods of the invention find use in experimental animals, in veterinary application, and in the development of animal models for disease, including, but not limited to, rodents including mice, rats, and hamsters; primates, and transgenic animals.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A practical Approach, Volumes I and II (D. N. Glover ed. 1985); Oligonucleotide Synthesis (M J. Gait ed. 1984); Nucleic Acid Hybridization (B. D. Hames & S. J. Higgins eds. (1985»; Transcription and Translation (B. D. Hames & S. J. Higgins, eds. (1984»; Animal Cell Culture (R. I. Freshney, ed. (1986»; Immobilized Cells and Enzymes (IRL Press, (1986»; B. Perbal, A practical Guide To Molecular Cloning (1984); F. M. Ausubel et al. (eds.), Current Protocols in Molecular Biology, John Wiley & Sons, Inc. (1994); among others.

Method and Platform of the Invention

The present invention provides several useful techniques for the analysis of TCR biology, including a single cell based protocol for γδ TCR amplification, a rapid protocol for TCR cloning and expression, and a novel platform for functional characterization of TCR clones (see FIGS. 5A and 5B). The invention provides an accurate and efficient method to approach rapid TCR cloning at the single cell level, which can improve the development of multiple applications, including TCR-mediated immunotherapy.

The most prominent recent immunotherapy approaches involve T cell checkpoint blockade inhibitors[51]. However, these therapies depend on the presence of significant numbers of anti-tumor T cell responses. The ex vivo expansion of tumor infiltrating lymphocytes has also been successful, but is time consuming[52]. The method of the present invention significantly accelerates the amount of time needed to generate large numbers of anti-tumor T cells, by allowing the efficient transduction of identified anti-tumor receptors. The key to the application of the invention of directed T cell immunotherapy is the rapid and accurate isolation and cloning of paired TCRs. Thus far, various methods have been developed for the cloning of TCR genes by traditional PCR, but the acquisition and expression of TCRs is often labor-intensive, time-consuming, expensive, and non-specific. The present invention provides efficient acquisition of TCR gene products for cloning based on single cell isolation, with an amplification success rate of isolated paired single cell TCRγ and TCRδ CDR3 products of 71.25±18.75% based on total sorted single cells in each sample.

The invention also provides a platform for screening TCR activation after cloning. By inserting the Nur77 reporter into a Jurkat 76 TCRα-β-cell line, a useful system for monitoring specific TCR activation was generated, as demonstrated by stimulation of PB1-NJ76 by its cognate influenza-derived peptide and stimulation of TRGV9/TRDV2 T cells with, e.g., zoledronic acid.

In certain embodiments, the invention employs the insertion of Nur77-GFP BAC DNA into the Jurkat cell line as a reporter cell line. Prior approaches to detect T cell activation include CD69 expression on the cell surface[22], and detection of IFNγ, IL-2, and TNFα protein levels in cell culture supernatants by ELISA[21,22]. These conventional methods have some shortcomings. For instance, CD69 is common activation marker of T cells, so it cannot show the specific activation of T cells through TCR signaling-bystander activation can occur. Detection of IFNγ, IL-2 and TNFα by ELISA is time-consuming (2 days) and expensive, and Detection of IFNγ, IL-2 and TNFα by real-time is labor-intensive (requires RNA isolation), time-consuming (at least a day).

The Nur77-GFP system has been demonstrated to reflect specific TCR triggering after stimulation[40,41,42], instead of activation by other receptors on the cell surface, like TLRs, NKG2A/2D, or other inhibitory receptors. Furthermore, GFP is directly assayable by flow cytometry without any secondary processing. The Nur77-GFP system allows rapid and accurate detection of specific T cell stimulation in a high-throughput manner. In certain embodiments, the invention provides that zoledronic acid induces the GFP expression of TRGV9/TRDV2 Nur77-GFP cells, demonstrating that the invention platform is functional, and zoledronic acid can be used in combination with TRGV9/TRDV2-expressing cells as a positive control for the test platform and that peptides can be used in combination with their cognate TRBV/TRAV-expressing cells (as demonstrated in FIG. 3B) as a control for the test platform.

Therefore, the present invention provides a novel platform and/or system that can be used to test different molecules directly by stimulating the Nur77-GFP Jurkat cell line, and characterizing and quantifying the stimulation based on GFP expression by flow cytometry. The platform of the present invention is faster, easier and more inexpensive (no need to stain) to perform, and can be used to screen TCR-activating or modifying drugs in a high-throughput screening manner as compared to prior art platforms.

In other embodiments, a Nur77-Luciferase reporter, which has a lower signal to noise ratio, is included in the Nur77-GFP Jurkat cell line to decrease the background for certain types of drug screening. Insertion of Nur77-Luciferase BAC DNA into the Jurkat cell line instead of Nur77-GFP can be undertaken, followed by luciferase detection in various assays that include high-throughput screening platforms. The luciferase detection may be conducted with between $5\times10^4$ to $2.5\times10^5$ cells per well, or about $1\times10^5$ cells per well, for highly sensitive detection.

Another application of the Nur77-GFP system is to screen for compounds that inhibit T cell activation. The Nur77-GFP system of the invention can be used for drug screening, clinical applications, and basic immunology research.

Considering the variability of CDR3 sequences and TCR variable regions (approximately $10^{18}$ combinations in human TCRγδ cells and $10^{16}$ combinations for TCRαβ cells[53]) and the complexity of cloning all the different clones de novo, the invention provides a method using overlap extension PCR of a linker molecule with amplified single cell CDR3 products and a constructed γδ (or αβ) TCR library to rapidly (less than 5 days) generate diverse TCR clones. Setting up a TCR clone library with all possible combination of TCRγ/TCRδ or TCRγ/TCRα pairings and a DNA linker library allows the achievement of superior speed by overcoming the need to synthesize the hypervariable CDR3 portion of the DNA. In the method of the present invention, as soon as the sequence information of the TCR CDR3 region from the single-cell PCR and their family usage are known, the relevant clone can be picked up from the library with the required TRBV and TRAV families to use as a backbone for the final construct. The single-cell PCR products of TCRβ/γ and TCRα/δ can then be linked together by using two terminal primers and a DNA linker by overlapping PCR. Next, this target gene can be substituted directly into the existing clones and the irrelevant CDR3s can be replaced with the specific ones while preserving the family usage. In certain embodiments, new CDR3s of TRGV9-TRDV2 are put into the existing cloning of TRGV9-TRDV2 vector with different CDR3s by overlapping extension PCR. With the method of the present invention, cloning TCR genes can be achieved within 5 days.

As compared to prior art methods[21,22], important advantages of the methods of the present invention are as follows:
1. The method of the present invention provides a way to build a library of clones as a one-time necessity that can serve as a backbone to the second, rapid TCR cloning method.
2. The method of the present invention does not require stimulation of PBMCs (e.g., with PHA/IL-2), which saves at least 1 day (and potential variability and survival issues) and helps avoid bias in the TCR repertoire in the subsequent analyses (as stimulation of PBMCs may cause unnecessary selection of TCR repertoire due to expansion of a subset of T cells, as well as a high rate and/or non-physiological level of dual TCRa and dual TCRβ expression in a single cell due to clonal expansion under the stimulation).
3. The method of the present invention is substantially faster than the reported approaches and relies on more robust processes. Once the library is made, the invention platform only needs 5 days to clone TCRs. Prior approaches are more labor intensive because they clone the full-length TCR de novo. In contrast, the method of the present invention uses the single-cell PCR products to clone any pairs of TCRs, and the libraries constructed using these clones can be continuously used.
4. The method of the present invention can yield an average 71% of TCR pairs from human samples (compare with an average 34% yield reported in[22] or 147 T cells in samples from 61 patients identified in[21]).
5. While in prior methods[22] TCRα/γ and TCRβ/δ were inserted into different vectors to transfect cells, which may cause the biased expression of TCRs, in the method of the present invention TCRα/γ and TCRβ/δ are inserted under the same promoter separated by a 2A sequence to ensure their equal level of expression.
6. In certain embodiments, the method of the present invention uses Jurkat 76 cell line (the TCR-negative human T cell line) to express human TCR clones. Such human cell line likely more accurately mimics human T cells and is more amenable to adoptive transfer therapy than mouse cell lines used in prior art.
7. The single-cell technique used in the method of the present invention allows to examine small number of cells (as low as 1) which is important e.g., in solid tumors where the numbers of TILs are limiting.

Uses of the Methods of the Invention

The rapid TCR cloning method of the present invention is very useful for immunotherapy. Tumor-specific T cells have been characterized by broad non-specific surface phenotypes that can be used to isolate, clone, and express potential tumor-targeted clones[54]. The recent advancement of tumor sequencing has allowed for identification of tumor neoantigens and overexpressed self-antigens[55,56,57,58]. Combining these technologies will allow characterizion and tailoring of anti-tumor therapy.

T cell transfers have also been used for the treatment of opportunistic infections in immunosuppressed patients, particularly after hematopoietic stem cell transplant. The reactivation of herpes viruses like human cytomegalovirus and Epstein-Barr virus is a clinical dilemma that cannot always be addressed with antivirals[24,59,60]. Analogous to TIL therapies, ex vivo expansion of antiviral T cell specificities can be clinically useful, but suffers from similar workflow limitations. By generating a library of specific TCR constructs reactive against a range of viruses and HLA types, TCR-directed therapies could be used prophylactically or immediately at the earliest signs of reactivation.

In addition to these therapeutic applications, the method of the present invention significantly improves the workflow for cloning and expressing TCRs for study in vitro. This can include the characterization of biochemical features of the TCR-peptide-MHC interaction, or, in the case where ligands have not been identified transduced cell lines can be used for the screening of novel antigens. This is particularly useful in the context of γδ T cells, where very few ligands have been identified and confirmed[18,61]. The GFP reporter line engineered can be used directly in high-throughput screening platforms; alternative reporters (such as, e.g., luciferase) can be easily substituted as well.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1

Materials and Methods

Subjects and peripheral blood mononuclear cell (PBMC) samples. Samples were obtained using research protocols approved by St. Jude Children's Research Hospital's institutional review boards (IRB) (Memphis, Tenn.). Peripheral whole blood was collected from heparinized apheresis rings from healthy immunocompetent individuals not taking immunomodulatory pharmaceutical agents. PBMCs were isolated via density gradient centrifugation (GE Healthcare Ficoll-Paque PLUS), and red blood cells (RBCs) were removed using RBC lysis buffer (8.3 g $NH_4Cl$, 1 g $KHCO_3$, and 1 ml 0.1% Phenol Red in 1 L distilled water). Isolated PBMCs were frozen in −80° C. for future use. All PBMCs used in the paper were stored frozen. Compared to fresh PBMC data from healthy apheresis rings, frozen PBMCs did not have a significantly lower success rate for single-cell amplification.

Figure 8:
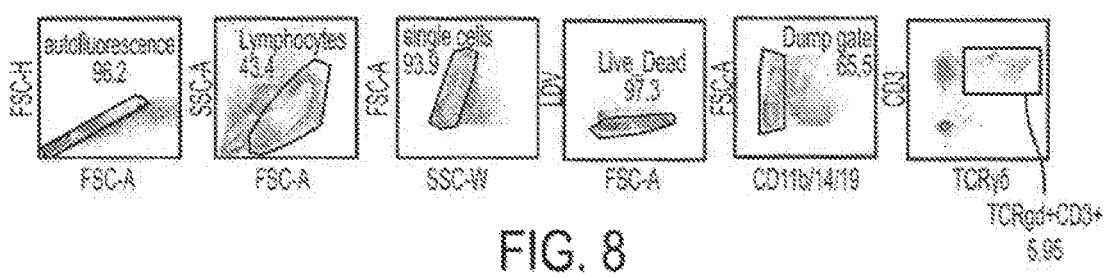
FIG. 8 shows a gating strategy of Human TCRγ/δ⁺ CD3⁺ cells single cell sorting. Single cells of human TCRγδ⁺ CD3⁺ cells from PBMC samples were sorted into 96-well plate by applying the gating strategy of FIG. 7, above. The gating is flowing "autofluorescence gate–lymphocytes gate–single cell gate–live/dead gate–dump gate (CD11b/14/19)–TCRγδ⁺/CD3⁺ gate".

Single cell sorting and staining. PBMCs were treated with human FcR blocking reagent (Miltenyi Biotec) on ice for 20 minutes. Human TCRγδ cells were isolated by staining with PE-conjugated anti-human TCRγ/δ (Biolegend, clone: B1), FITC-conjugated anti-human CD3 (Biolegend, clone: OKT3), a dump gate consisting of APC-conjugated anti-human CD11b/CD14/CD19 (Biolegend, CD11b clone: ICRF44; Biolegend, CD14 clone: HCD14; Biolegend, CD19 clone: HIB19) and Live/Dead Violet exclusion dye (Invitrogen, L34955) on ice for 30 minutes. After staining, TCRγ/δ+ CD3+ cells were sorted directly into a 96-well PCR plate (Biorad) with a sorter (Model sy3200, Sony Biotech Synergy sorter) by the following gating strategy: autofluorescence gate–lymphocytes gate–single cell gate–live/dead gate–dump gate (CD11b/14/19)–TCRγδ/CD3 gate (FIG. 8). The last 2 columns of the plate were left empty for use as PCR negative controls. After sorting, plates were stored at −80° C. until downstream processing. Human α/β T cells were also isolated using the same method[27], which consisted of APC-conjugated anti-human CD14/CD19/CD11b (Biolegend, CD14 clone: HCD14; Biolegend, CD19 clone: HIB19; Biolegend, CD11b clone: ICRF44), PE-conjugated anti-human TCRα/β (Biolegend, clone: IP26), FITC-conjugated anti-human CD3 (Biolegend, clone: OKT3) and Live/Dead Violet L34955 (Invitrogen). To increase PCR efficiency, the plates were pre-loaded with mixture of RT-PCR by SuperScript® VILO cDNA synthesis kit and single cells were sorted directly into these plates.

Reverse transcription, multiplex, nested single cell PCR, and sequencing. cDNA from TCRγδ and TCRαβ mRNA was reverse transcribed directly from the sorted and stored single cells in the PCR plate without any RNA extraction step using the iScript cDNA Synthesis Kit (Bio-Rad) in a 2.5 μl reaction mix as per the method described previously[26]. The cDNA synthesis was carried out by incubating at 25° C. for 5 min, 42° C. for 30 min, and 80° C. for 5 min (For the first round and second round of PCR). Alternatively, the SuperScript® VILO cDNA synthesis kit was used which produces a higher success rate for single cell PCR by incubating the reaction mixture at 25° C. for 10 min, 42° C. for 60 min, and 80° C. for 5 min. The TCRαβ transcripts from each cell were amplified by a multiplex nested PCR strategy as described previously[26,27]. For amplification of TCRγδ transcripts, the overall strategy was similar to the published TCRαβ amplification (95° C. for 2 min, followed by 35 cycles of 95° C. for 20 s, 53° C. for 20 s, and 72° C. for 45 s, followed by final extension of 72° C. for 7 min.), except for the primers described in Table 1.

TABLE 1

Primers targeting human T cells receptor gamma (TRGV) and delta (TRDV) genes

| TRGV gene(s) targeted by primer | External primer sequence | Internal primer sequence |
| --- | --- | --- |
| HuTRGV3.5 | 5'TCTTCCAACTTGGAAGGG3' (SEQ ID NO: 1) | 5'GGTCATCTGCTGAAATCAC3' (SEQ ID NO: 2) |
| HuTRGV7 | 5'TCTTCCAACTTGCAAGGG3' (SEQ ID NO: 3) | 5'GGTCATCTGCTGTAATCACTTG3' (SEQ ID NO: 4) |
| HuTRGVA | 5'GGGTCATCCTGTTTCCAG3' (SEQ ID NO: 5) | 5'TACCTAAGGACCTGTGTAGAGG3' (SEQ ID NO: 6) |
| HuTRGVB | 5'TGGCCTCCCAAAGTACTG3' (SEQ ID NO: 7) | 5'TCCTCTTTCTATGTCCCAGG3' (SEQ ID NO: 8) |
| HuTRGV8 | 5'CCAACTTGGAAGGGAGAAC3' (SEQ ID NO: 9) | 5'AAAATGCCGTCTACACCC3' (SEQ ID NO: 10) |
| HuTRGV9 | 5'CCAGGTCACCTAGAGCAAC3' (SEQ ID NO: 11) | 5'TGTCCATTTCATATGACGG3' (SEQ ID NO: 12) |
| HuTRGV10 | 5'TTATCAAAAGTGGAGCAGTTC3' (SEQ ID NO: 13) | 5'CAGCTATCCATTTCCACGG3' (SEQ ID NO: 14) |
| HuTRGV11 | 5'GAACAACCTGAAATATCTATTTCC3' (SEQ ID NO: 15) | 5'CATATCTTGGAAGGCATCC3' (SEQ ID NO: 16) |
| HuTRGV1.2.4.6 | 5'GGGTCATCTGCTGAAATCAC3' (SEQ ID NO: 17) | 5'CCAGGAGGGGAAGGC3' (SEQ ID NO: 18) |
| HuTRGC | 5'GGTGTTCCCCTCCTGG3' (SEQ ID NO: 19) | 5'CCCAGAATCGTGTTGCT3' (SEQ ID NO: 20) |
| HuTRDV1 | 5'GCCCAGAAGGTTACTCAAG3' (SEQ ID NO: 21) | 5'AGCAAAGAGATGATTTTCCTTA3' (SEQ ID NO: 22) |

TABLE 1-continued

Primers targeting human T cells receptor gamma (TRGV) and delta (TRDV) genes

| TRGV gene(s) targeted by primer | External primer sequence | Internal primer sequence |
|---|---|---|
| HuTRDV2 | 5'ATTGAGTTGGTGCCTGAAC3' (SEQ ID NO: 23) | 5'TATATCAACTGGTACAGGAAGACC3' (SEQ ID NO: 24) |
| HuTRDV3 | 5'TGTGACAAAGTAACCCAGAGTTC3' (SEQ ID NO: 25) | 5'GGTACTGCTCTGCACTTACGAC3' (SEQ ID NO: 26) |
| HuTRDV4/ TRAV14 | 5'CAAACCCAACCAGGAATG3' (SEQ ID NO: 27) | 5'AGGAAAAGGAGGCTGTGAC3' (SEQ ID NO: 28) |
| HuTRDV5/ TRAV29 | 5'GCAAGTTAAGCAAAATTCACC3' (SEQ ID NO: 29) | 5'CTGCTGAAGGTCCTACATTC3' (SEQ ID NO: 30) |
| HuTRDV6/ TRAV23 | 5'TTGATAGTCCAGAAAGGAGG3' (SEQ ID NO: 31) | 5'CGTTTGACTACTTTCCATGG3' (SEQ ID NO: 32) |
| HuTRDV7/ TRAV36 | 5'GACAAGGTGGTACAAAGCC3' (SEQ ID NO: 33) | 5'ATCTCTGGTTGTCCACGAG3' (SEQ ID NO: 34) |
| HuTRDV8/ TRAV38-2 | 5'CAGTCACTCAGTCTCAACCAG3' (SEQ ID NO: 35) | 5'TCTGGTACAAGCAGCCTC3' (SEQ ID NO: 36) |
| HuTRDC | 5'CTTCATATTTACCAAGCTTGACAG3' (SEQ ID NO: 37) | 5'GATGACAATAGCAGGATCAAAC3' (SEQ ID NO: 38) |

Nine (9) TRGV external sense primers, nine (9) TRGV internal sense primers, eight (8) TRDV external sense primers and eight (8) TRDV internal sense primers targeted for individual TRGV and TRDV families were designed based on the sequences derived from the IMGT database[62]. For the antisense primer, single TRGC external, TRGC internal, TRDC external, and TRDC internal primers complementary to the published TRGC and TRDC sequences in IMGT were designed. Human TRAV14/DV4, TRAV23/DV6, TRAV29/DV5, TRAV36/DV7, and TRAV38-2/DV8 are shared primers in TRAV and TRDV primer sets.

The primers were synthesized by IDT and stored at −20° C. at a stock concentration of 100 μM in TE with low EDTA (pH8.0). The primers for each category (sense external, sense internal of TRGV and TRDV) were combined so that the final concentration of each primer in the mixture was 10 μM. The antisense primers were diluted to 10 μM. The PCR conditions for the TCRγδ nested PCR were 95° C. for 2 min, followed by 35 cycles of 95° C. for 20 s, 53° C. for 20 s, and 72° C. for 45 s, followed by final extension of 72° C. for 7 min. The PCR products were run on a 2% agarose gel to check for the success rate of the PCR as well as contamination following which the products were purified by a modified Exonuclease I—rShrimp alkaline phosphatase (ExoSAP-IT®) method[63] to eliminate unincorporated primers and dNTPs for high quality DNA sequencing. 1 μl of the single cell PCR product was added into the mixture of 4.6 μl of Tris-Cl (50 mM, pH8.0), 0.2 μl of Exonuclease I and 0.2 μl of rShimp alkaline phosphatase and was incubated at 37° C. for 15 min and 80° C. for 15 min. The purified PCR products were sequenced using the relevant TRAC, TRBC, TRGC or TRDC primer. A schematic of the PCR strategy is shown in FIG. 1A.

gBlock® gene fragments, Gibson Assembly® and Transformation. The gBlock® gene fragments encoding the library of TRGVs and TRDVs were obtained from Integrated DNA Technologies (IDT). The expression vector pMICherry (10 μg), which was modified from the parental pMIGII[64] by changing GFP to an mCherry reporter, was double digested by EcoR I (20 units) and Xho I (20 units) restriction enzymes (New England Biolabs) at 37° C. for 3 h as per manufacturer's instruction. Agarose gel purified-linearized pMICherry vector (100 ng) and 2×TCR gBlock inserts were ligated in a three-way ligation, including the TCRγ gene, TCR gene, and linearized vector by using the Gibson Assembly® Cloning kit (New England Biolabs) per manufacturer's instructions. Two microliters of the ligation mixture was transformed into DH5α Competent E. coli (New England Biolabs) per manufacturer's instructions.

Generation of human CD3 constructs. Human CD3 δ, γ, ε and δ genes were amplified from human PBMC cDNA using the primers in Table 2a. All the genes were linked together by overlap PCR with species-specific 2A regions inserted[35]. The types and amino acid sequences of the 2As used are shown in Table 2b. The CD3 gene complex was then cloned into an MSCV-based retroviral vector that contains an IRES[31,32,65] and ametrine as a reporter gene.

TABLE 2a

2A Primers targeting human CD3δ, γ, ε and ζ genes

| TRGV gene(s) targeted by primer | Primer sequence |
|---|---|
| CD3δ sense | 5'CCCTCACTCCTTCTCTAGGCGCCGGAATTCGCCAGGATGGAACATAGCACG3' (SEQ ID NO: 39) |
| CD3δ antisense | 5'CCACGTCTCCCGCCAACTTGAGAAGGTCAAAATTCAAAGTCTGTTTCACCGGTCCCTTGTTCCGAGCC3' (SEQ ID NO: 40) |
| CD3γ sense | 5'GAATTTTGACCTTCTCAAGTTGGCGGGAGACGTGGAGTCCAACCCAGGGCCCATGGAACAGGGGAAG3' (SEQ ID NO: 41) |

TABLE 2a-continued

2A Primers targeting human CD3δ, γ, ε and ζ genes

| TRGV gene(s) targeted by primer | Primer sequence |
|---|---|
| CD3γ antisense | 5'CCTCGACGTCACCGCATGTTAGCAGACT TCCTCTGCCCTCAGATCTTCTATTCCTCCT CAAC3' (SEQ ID NO: 42) |
| CD3ε sense | 5'CAGAGGAAGTCTGCTAACATGCGGTGAC GTCGAGGAGAATCCTGGCCCAATGCAGTCG GGCACTC3' (SEQ ID NO: 43) |
| CD3ε antisense | 5'GTTTTCTTCCACGTCTCCTGCTTGCTTT AACAGAGAGAAGTTCGTGGCGGATCCTCCG ATGCGTCTCTG3' (SEQ ID NO: 44) |
| CD3ζ sense | 5'CTCTCTGTTAAAGCAAGCAGGAGACGTG GAAGAAAACCCCGGTCCCATGAAGTGGAAA GTG3' (SEQ ID NO: 45) |
| CD3ζ antisense | 5'GAGGGAGAGGGGCGGAATTGATCCTCGA GCAATTGTTAGCGAGGGGCCAG3' (SEQ ID NO: 46) |

TABLE 2b

Types and sequences of 2A regions

| 2A Type | 2A amino acid sequence | Separation |
|---|---|---|
| F2A (foot and-mouth disease virus) | VKQTLNFDLLKLAGD VESNPGP (SEQ ID NO: 47) | CD3δ and CD3γ |
| T2A (Thosea asigna virus) | EGRGSLLTCGDVEEN PGP (SEQ ID NO: 48) | CD3γ and CD3ε |
| P2A (porcine teschovirus-1) | ATNFSLLKQAGDVEE NPGP (SEQ ID NO: 49) | CD3ε and CD3ζ |

DNA Isolation, Cell Culture and Transfection. Recombinant pMICherry plasmids with full length TCRαβ or TCRγδ inserts were isolated in small scale by using a NucleoSpin® Plasmid kit (Clontech) and in large scale for transfection using a Plasmid Midi kit (Qiagen) per the manufacturer's instructions. The Neon® Transfection System was used to transfect 10 μg TCRαβ or γδ DNA in the pMICherry vector into the human Jurkat 76 TCRα⁻β⁻ cell line (2×10⁷ cells/mL, 100 μl)[66], followed by three pulses with a voltage of 1,350V and a width of 10 ms. The transfected cells were cultured for 48 h before being assayed for TCRαβ or TCRγδ expression on the surface by FACS analysis. The human Jurkat 76 cells TCRα⁻β⁻ cell line was cultured in complete-RPMI 1640 medium, which is RPMI 1640 with 10% of fetal bovine serum, 1% Penicillin Streptomycin, and 1% L-glutamine at 37° C. and 5% CO$_2$.

Immunofluorescent and flow cytometric analysis For surface staining, cells (1-5×10⁵) were harvested from culture and washed with FACS buffer (PBS with 1% of BSA and 0.1% sodium azide) prior to staining. The cells were treated with human FcR blocking reagent (Miltenyi Biotec) on ice for 20 min, and cells were then treated with various fluorescent conjugated antibodies against cell surface markers in FACS buffer. Human γδ T cells were stained with APC-conjugated anti-human TCRγ/δ (Biolegend, clone: B1) or APC-conjugated anti-human TCRα/β (Biolegend, clone: IP26) and Pacific Blue-conjugated anti-human CD3 (Biolegend, clone: OKT3). For influenza-specific tetramer staining, cells (1-5×10⁵) were stained with APC-conjugated Influenza-M1 tetramer (Beckman Coulter, HLA-A*0201, GILGFVFTL (SEQ ID NO: 146)) in FACS buffer at room temperature for 1 h prior to surface staining with the same staining antibodies described.

Figure 4:
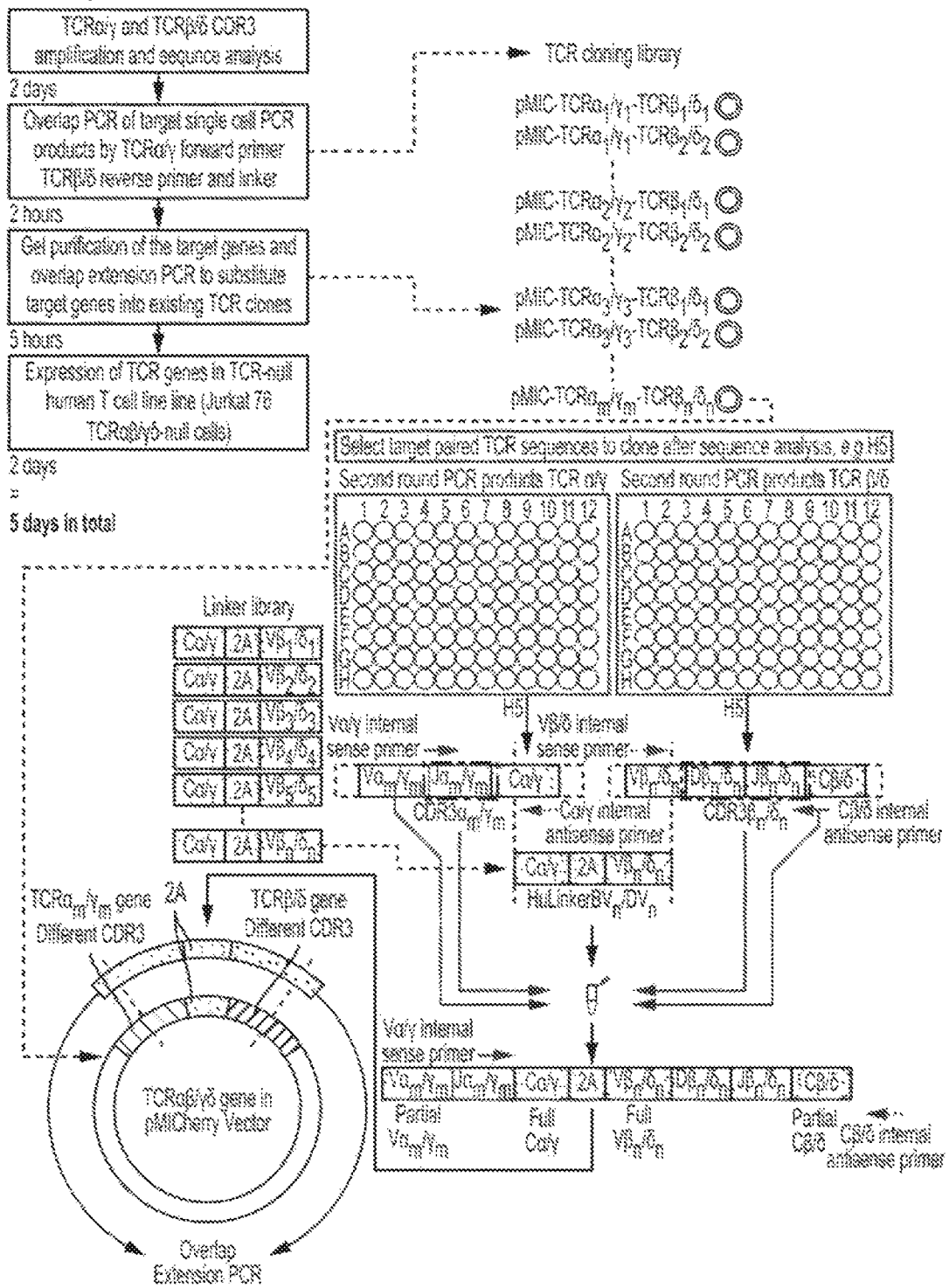
FIG. 4 shows a schematic strategy of CDR3 substitution by overlap extension PCR. Based on the library of TCRαβ and TCRγδ established by the described cloning platform, the strategy for CDR3 substitution using multiplex single cell PCR products and linker DNA is shown. After the sequence analysis of single-cell PCR (shown in FIG. 1A), the target pairs of TCRs are chosen from the respective second round paired PCR plates, which include TCRα/γ$_m$ and TCRβ/δ$_n$ (m represents a particular TRAV or TRGV subfamily; n represents a particular TRBV or TRDV subfamily). Beforehand, we generated a library of linker DNA by gBlock synthesis (IDT) (Table 3). The linker DNA consists of TRAC/TRGC-2A-TRBVn/TRDVn (n represents the TRB/DV subfamily) sequence. Using the single cell PCR products of α/γ and β/δ chains of the desired clonotypes and the relevant linker gBlock DNA, we carried out an overlap PCR with TRAm/GVm internal sense primer and TRB/DC internal antisense primer. The PCR products were visualized on an agarose gel, and subsequently purified to use as "mega-primer" for cloning into the existing construct from our TCR cloning library (pMIC-TCRα/γ$_m$-TCR β/δ$_n$) with the same TRGV and TRDV family usage but different CDR3s by overlap extension PCR. The timeline of the whole process is on the left.
Figure 6A:
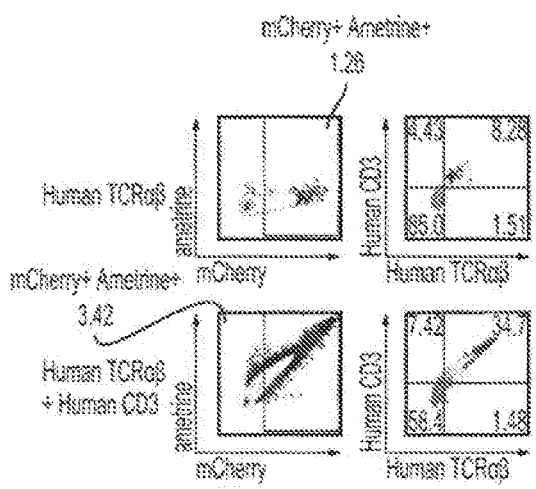
FIGS. 6A-6C show co-transfection of human CD3 can improve the expression of human TCR constructs.
Figure 6B:
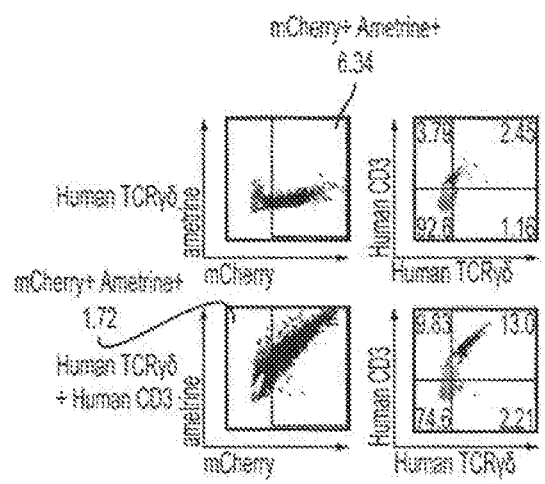
Figure 6C:
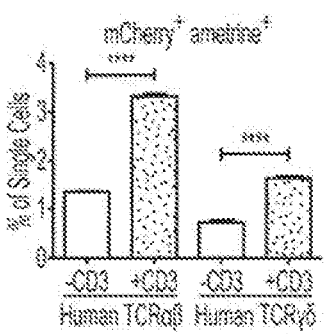
Figure 6C:
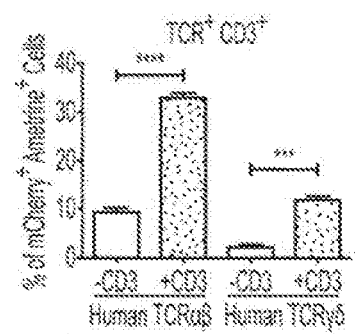

Modification of the CDR3 region by two-step overlap extension PCR cloning The substitution of the CDR3 was carried out by an overlap extension PCR cloning protocol[28]. A schematic diagram of the procedure is shown in FIG. 4. Briefly, a library of linker DNA was generated by gBlock synthesis at IDT (Table 3). The linker DNA consists of TRGC-2A-TRDVx (X represents the TRDV family) sequence. Using the single cell PCR products of γ and δ chains of the desired clonotype and the relevant linker gBock DNA we carried out an overlap PCR. The PCR reaction was set up and carried out as follows: 12.5 μl 2×Phusion® high-fidelity DNA polymerase (New England Biolabs), 0.25 μl of 100×DMSO, 1 μl of 10 μM TRGV internal sense primer, 1 μl of TRDV internal antisense primer (Table 1), 1 ng of linker DNA, and deionized H$_2$O up to 25 μl. The PCR program was 98° C. for 30 s; 34 cycles of each at 98° C. for 10 s, 58° C. for 30 s, 72° C. for 1 min; then finally 72° C. for 10 min. The PCR products were visualized on a 1% agarose gel, and purified from the gel to use for cloning into the existing construct with the same TRGV and TRDV family usage. The reaction conditions used were as follows: 20 ng of a TCR construct in pMICherry vector with identical TRGV and TRDV but an irrelevant CDR3γ and δ, with 50 ng of the first step PCR products, 12.5 μl of 2×Phusion® high-fidelity DNA polymerase, 0.25 μl of 100×DMSO, and deionized H$_2$O up to 25 μl. The PCR conditions used were 98° C. for 30 s; 17 cycles of each at 98° C. for 10 s, 65° C. for 30 s, 72° C. for 4 min; then finally 72° C. for 10 min. The PCR products were incubated with 1 μl DpnI enzyme (New England Biolabs) at 37° C. for 1 h, and 2-3 μl of the digested products transformed into NovaBlue Singles® competent cells (EMD Millipore).

TABLE 3

Human TCRγδ Linker DNA library
(lower case: TRGC sequence;
bold: 2A sequence; *italic*: TRDVx sequence)

| Linker DNA Name | Sequence |
|---|---|
| HuLinkerDV1 | 5'catacctttgtcttcttgagaaattttcccagata ttattaagatacattggcaagaaaagaagagcaacacg attctgggatcccaggagggggaacaccatgaagactaa cgacacatacatgaaatttagctggttaacggtgccag aagagtcactggacaaagaacacagatgtatcgtcaga catgagaataataaaaacggaattgatcaagaaattat ctttcctccaataaagacagatgtcatcacaatggatc ccaaagacaattggtcaaaagatgcaaatgatacacta ctgctgcagctcacaaacacctctgcatattacatgta cctcctcctgctcctcaagagtgtggtctattttgcca tcatcacctgctgtctgcttggaagaacggctttctgc tgcaatggagagaaatcaGCCACGAACTTCTCTCTGTT AAAGCAAGCAGGAGACGTGGAAGAAAACCCCGGTCCCA *TGCTGTTCTCCAGCCTGCTGTGTGTATTTGTGGCCTTC AGCTACTCTGGATCAAGTGTGGCCCAGAAGGTTACTCA AGCCCAGTCATCAGTATCCATGCCAGTGAGGAAAGCAG TCACCCTGAACTGCCTGTATGAAACAAGTTGGTGGTCA TATTATATTTTTTGGTACAAGCAACTTCCCAGCAAAGA GATGATTTTCCTTATTCGCC*3' (SEQ ID NO: 50) |

TABLE 3-continued

Human TCRγδ Linker DNA library
(lower case: TRGC sequence;
bold: 2A sequence; *italic*: TRDVx sequence)

| Linker DNA Name | Sequence |
|---|---|
| HuLinkerDV2 | 5'catacattgtatatgagaaattttttcccagatatta ttaagatacattggcaagaaaagaagagcaacacgatt ctgggatcccaggaggggaacaccatgaagactaacga cacatacatgaaatttagctggttaacggtgccagaag agtcactggacaaagaacacagatgtatcgtcagacat gagaataataaaaacggaattgatcaagaaattatctt tcctccaataaagacagatgtcatcacaatggatccca aagacaattggtcaaaagatgcaaatgatacactactg ctgcagctcacaaacacctctgcatattacatgtacct cctcctgctcctcaagagtgtggtctattttgccatca tcacctgctgtctgcttggaagaacggctttctgctgc aatggagagaaatcaGCCACGAACTTCTCTCTGTTAAA GCAAGCAGGAGACGTGGAAGAAAACCCCGGTCCCA*TGC AGAGGATCTCCTCCCTCATCCATCTCTCTCTTCTGG GCAGGAGTCATGTCAGCCATTGAGTTGGTGCCTGAACA CCAAACAGTGCCTGTGTCAATAGGGGTCCCTGCCACCC TCAGGTGCTCCATGAAAGGAGAAGCGATCGGTAACTAC TATATCAACTGGTACAGGAAGACCCAAGG*3' (SEQ ID NO: 51) |
| HuLinkerDV3 | 5'catacctttgtcttcttgagaaattttttcccagata ttattaagatacattggcaagaaaagaagagcaacacg attctgggatcccaggaggggaacaccatgaagactaa cgacacatacatgaaatttagctggttaacggtgccag aagagtcactggacaaagaacacagatgtatcgtcaga catgagaataataaaaacggaattgatcaagaaattat cttcctccaataaagacagatgtcatcacaatggatc ccaaagacaattggtcaaaagatgcaaatgatacacta ctgctgcagctcacaaacacctctgcatattacatgta cctcctcctgctcctcaagagtggtctattttgcca tcatcacctgctgtctgcttggaagaacggctttctgc tgcaatggagagaaatcaGCCACGAACTTCTCTCTGTT AAAGCAAGCAGGAGACGTGGAAGAAAACCCCGGTCCCA  *TGATTCTTACTGTGGCTTTAGCTTTTTGTTTTTCTAC AGGGGCACGCTGTGTGACAAAGTAACCCAGAGTTCCCC GGACCAGACGGTGGCGAGTGGCAGTGAGGTGGTACTGC TCTGCACTTACGACACTG*3' (SEQ ID NO: 52) |
| HuLinkerDV4 | 5'catacctttgtcttcttgagaaattttttcccagata ttattaagatacattggcaagaaaagaagagcaacacg attctgggatcccaggaggggaacaccatgaagactaa cgacacatacatgaaatttagctggttaacggtgccag aagagtcactggacaaagaacacagatgtatcgtcaga catgagaataataaaaacggaattgatcaagaaattat cttcctccaataaagacagatgtcatcacaatggatc ccaaagacaattggtcaaaagatgcaaatgatacacta ctgctgcagctcacaaacacctctgcatattacatgta cctcctcctgctcctcaagagtgtggtctattttgcca tcatcacctgctgtctgcttggaagaacggctttctgc tgcaatggagagaaatcaGCCACGAACTTCTCTCTGTT AAAGCAAGCAGGAGACGTGGAAGAAAACCCCGGTCCCA *TGTCACTTTCTAGCCTGCTGAAGGTGGTCACAGCTTCA CTGTGGCTAGGACCTGGCATTGCCCAGAAGATAACTCA AACCCAACCAGGAATGTTCGTGCAGGAAAAGGAGGCTG TGACTCTGG*3' (SEQ ID NO: 53) |
| HuLinkerDV5 | 5'catacctttgtcttcttgagaaattttttcccagata ttattaagatacattggcaagaaaagaagagcaacacg attctgggatcccaggaggggaacaccatgaagactaa cgacacatacatgaaatttagctggttaacggtgccag aagagtcactggacaaagaacacagatgtatcgtcaga catgagaataataaaaacggaattgatcaagaaattat cttcctccaataaagacagatgtcatcacaatggatc ccaaagacaattggtcaaaagatgcaaatgatacacta ctgctgcagctcacaaacacctctgcatattacatgta cctcctcctgctcctcaagagtgtggtctattttgcca tcatcacctgctgtctgcttggaagaacggctttctgc tgcaatggagagaaatcaGCCACGAACTTCTCTCTGTT AAAGCAAGCAGGAGACGTGGAAGAAAACCCCGGTCCCA *TGGCCATGCTCCTGGGGGCATCAGTGCTGATTCTGTGG CTTCAGCCAGACTGGGTAAACAGTCAACAGAAGAATGA TGACCAGCAAGTTAAGCAAATTCACCATCCCTGAGCG* |

TABLE 3-continued

Human TCRγδ Linker DNA library
(lower case: TRGC sequence;
bold: 2A sequence; *italic*: TRDVx sequence)

| Linker DNA Name | Sequence |
|---|---|
| | *TCCAGGAAGGAAGAATTTCTATTCTGAACTGTGACTAT ACTAACAGCATGTTTGATTATTTCCTATGGTACAAAAA ATACCCTGCTGAAGGTCCTACATTCCTGATATC*3' (SEQ ID NO: 54) |
| HuLinkerDV6 | 5'catacctttgtcttcttgagaaattttttcccagata ttattaagatacattggcaagaaaagaagagcaacacg attctgggatcccaggaggggaacaccatgaagactaa cgacacatacatgaaatttagctggttaacggtgccag aagagtcactggacaaagaacacagatgtatcgtcaga catgagaataataaaaacggaattgatcaagaaattat cttcctccaataaagacagatgtcatcacaatggatc ccaaagacaattggtcaaaagatgcaaatgatacacta ctgctgcagctcacaaacacctctgcatattacatgta cctcctcctgctcctcaagagtgtggtctattttgcca tcatcacctgctgtctgcttggaagaacggctttctgc tgcaatggagagaaatcaGCCACGAACTTCTCTCTGTT AAAGCAAGCAGGAGACGTGGAAGAAAACCCCGGTCCCA *TGGACAAGATCTTAGGAGCATCATTTTTAGTTCTGTGG CTTCAACTATGCTGGGTGAGTGGCCAACAGAAGGAGAA AAGTGACCAGCAGCAGGTGAAACAAAGTCCTCAATCTT TGATAGTCCAGAAAGGAGGGATTTCAATTATAAACTGT GCTTATGAGAACACTGCGTTTGACTACTTTCCATGGTA CC*3' (SEQ ID NO: 55) |
| HuLinkerDV7 | 5'catacctttgtcttcttgagaaattttttcccagata ttattaagatacattggcaagaaaagaagagcaacacg attctgggatcccaggaggggaacaccatgaagactaa cgacacatacatgaaatttagctggttaacggtgccag aagagtcactggacaaagaacacagatgtatcgtcaga catgagaataataaaaacggaattgatcaagaaattat cttcctccaataaagacagatgtcatcacaatggatc ccaaagacaattggtcaaaagatgcaaatgatacacta ctgctgcagctcacaaacacctctgcatattacatgta cctcctcctgctcctcaagagtgtggtctattttgcca tcatcacctgctgtctgcttggaagaacggctttctgc tgcaatggagagaaatcaGCCACGAACTTCTCTCTGTT AAAGCAAGCAGGAGACGTGGAAGAAAACCCCGGTCCCA *TGATGAAGTGTCCACAGCTTTACTAGCTATCTTTTTGG CTTCTACTGAGCTGGGTGAGCAGTGAAGACAAGGTGGT ACAAAGCCCTCTATCTCTGGTTGTCCACGAGGGAG*3' (SEQ ID NO: 56) |
| HuLinkerDV8 | 5'catacattgtatatgagaaattttttcccagatatta ttaagatacattggcaagaaaagaagagcaacacgatt ctgggatcccaggaggggaacaccatgaagactaacga cacatacatgaaatttagctggttaacggtgccagaag agtcactggacaaagaacacagatgtatcgtcagacat gagaataataaaaacggaattgatcaagaaattatctt tcctccaataaagacagatgtcatcacaatggatccca aagacaattggtcaaaagatgcaaatgatacactactg ctgcagctcacaaacacctctgcatattacatgtacct cctcctgctcctcaagagtgtggtctattttgccatca tcacctgctgtctgcttggaagaacggctttctgctgc aatggagagaaatcaGCCACGAACTTCTCTCTGTTAAA GCAAGCAGGAGACGTGGAAGAAAACCCCGGTCCCA*TGG CATGCCCTGGCTTCCTGTGGGCACTTGTGATCTCCACC TGTCTTGAATTTAGCATGGCTCAGACAGTCACTCAGTC TCAACCAGAGATGTCTGTGCAGGAGGCAGAGACCGTGA CCCTGAGCTGCACATATGACACCAGTGAGAGTGATTAT TATTTATTCTGGTACAAGCAGCCTCCCAG*3' (SEQ ID NO: 57) |

Nur77-GFP Jurkat 76 TCRα−β− cell line. To characterize the functionality of TCRαβ or γδ clones, we established the Nur77-GFP Jurkat 76 TCRα−β− cell line (NJ76 cells). After linearization of a Nur77-GFP BAC clone (constructed based on pTARBAC)[40] by mixing 10 μg BAC DNA, 2 μl 10× reaction buffer, 10 units of PI-SceI restriction enzyme (New England Biolabs), and nuclease-free water to make the volume up to 20 μl with incubation at 37° C. for 3 h and inactivation at 65° C. for 20 min, 80 µl of nuclease-free water, 15 µl of sterile sodium acetate (3M, pH7.0), and 300 µl of ethanol were added to the reaction mixture, which was then centrifuged at 12,000 g for 30 min at 4° C. The resulting DNA pellet was washed with 75% ethanol, dried in the air, and resuspended by Tris-EDTA buffer (pH 8.0). The Neon® Transfection System following the manufacturer's instruction was used to transfect the linearized BAC DNA into the human Jurkat 76 TCRα⁻β⁻ cell line (2×10⁷ cells/mL, 100 ul), and pulsed three times with a voltage of 1,350V and a width of 10 ms. Cells were then cultured in complete-RPMI 1640 medium containing 500 ug/ml Geneticin (Invitrogen) for selection.

Stimulation of $K^bPB1_{703}^+TCR\alpha\beta^+$ NJ76 cells (PB1-NJ76) by flu peptide PB1. NJ76 cell transfected with a murine $K^bPB1_{703}$-specific TCRαβ derived from influenza-infected mice and transfected cells were incubated with mouse splenocytes (cell number ratio of PB1-NJ76/splenocytes is 2:1), the influenza $PB1_{703-711}$ peptide (1 µM/ml), mouse splenocytes and peptide, and mouse α-CD3 (2C11; 10 µg/ml) and human α-CD28 (CD28.2; 10 µg/ml) in c-RPMI 1640 medium at 37° C. for 4 h. The GFP expression in the mouse TCRαβ⁺CD3⁺ cell population was quantified by flow cytometry.

Stimulation of TRGV9/TRDV2-NJ76 cells by Zoledronic acid. NJ76 cells transfected with a TRGV9/TRDV2 clone were incubated with 50 µg/ml zoledronic acid (Zometa, Novartis) in c-RPMI 1640 medium at 37° C. for 3 h, washed three times and incubated for 12 h. The GFP expression in the TCRγδ⁺CD3⁺ cell population was quantified by flow cytometry.

Example 2

Paired TCRγδ Analysis of Human PBMC Samples at the Single Cell Level

Figure 1B:
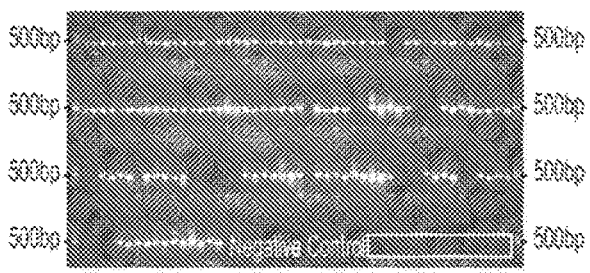
FIG. 1B shows an agarose gel electrophoresis image of TCR segments containing CDR3γ and CDR3δ is shown. Paired CDR3γ and CDR3δ products from the same cell were loaded in adjacent lanes. Negative control PCR reactions are shown in the boxed region and in the ladder lane, a 500 bp label is shown.
Figure 1C:
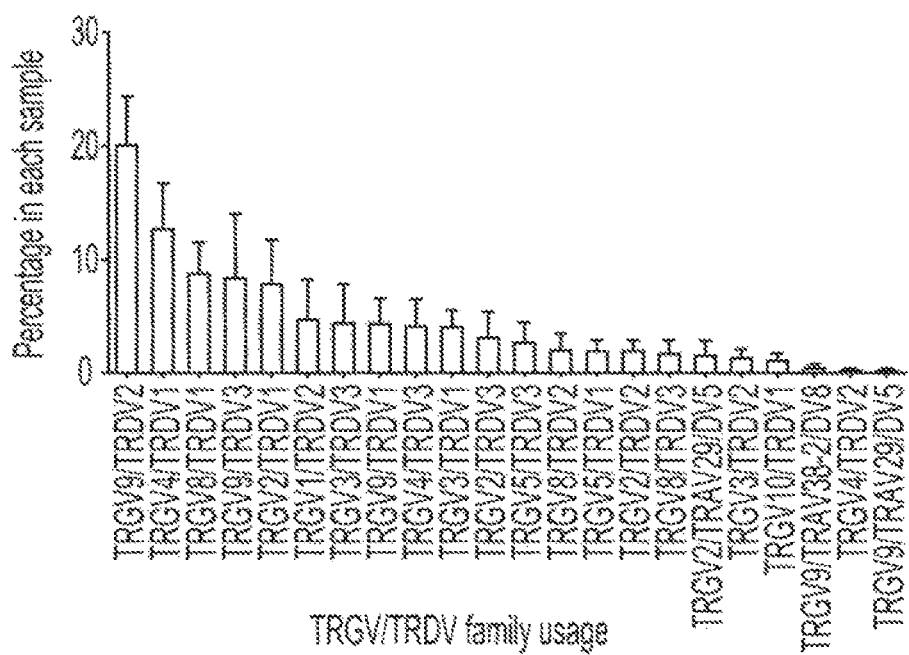
FIG. 1C shows the determination of paired TRGV/TRDV usage by multiplex PCR and sequencing (n=14 human apheresis rings), with the percentage of different TRGV/TRDV usage in each sample assessed (mean±SEM).

A strategy was developed to characterize the paired TCRγδ repertoire in humans. The primers were designed for all non-pseudogene TRGV and TRDV regions along with antisense primers for their respective constant regions. Two sets of primers (external and internal) were designed in order to perform a nested PCR (Table 1). The PCR products were examined by agarose gel electrophoresis before sequencing (FIG. 1B). The average success rate for obtaining paired CDR3γ and CDR3δ sequences at the single cell level from human PBMC samples by the present method is 71.25±18.75%. The TRGV/TRDV family usage was determined from the multiplex PCR products (FIG. 1C). On average, 20% of the sequences from the analysis of 14 human PBMCs were TRGV9/TRDV2. This technique along with the established mouse and human αβ single cell multiplex PCR offers a rapid method (turnaround time ~3 days per 160 cells) for characterizing paired TCRγδ chains at the single cell level. The data of paired TRGV/TRDV family usage percentage in each human sample are shown in Table 4.

TABLE 4

TRGV/TRDV repertoire among 14 human samples. The percentage of paired TRGV/TRDV usage was analyzed from the sequencing results of each 14 human PBMC samples. Average values, standard deviation and standard error were reported.

| — | Mean | Std. Deviation | Std. Error |
|---|---|---|---|
| TRGV9/TRDV2 | 20.06 | 16.11 | 4.306 |
| TRGV4/TRDV1 | 12.71 | 15 | 4.008 |
| TRGV8/TRDV1 | 8.714 | 10.63 | 2.842 |
| TRGV9/TRDV3 | 8.357 | 21.25 | 5.68 |
| TRGV2/TRDV1 | 7.836 | 14.61 | 3.906 |
| TRGV1/TRDV2 | 4.643 | 13.51 | 3.61 |
| TRGV3/TRDV3 | 4.35 | 13.09 | 3.498 |
| TRGV9/TRDV1 | 4.279 | 8.702 | 2.326 |
| TRGV4/TRDV3 | 4.071 | 9.059 | 2.421 |
| TRGV3/TRDV1 | 4.029 | 5.646 | 1.509 |
| TRGV2/TRDV3 | 3.071 | 8.801 | 2.352 |
| TRGV5/TRDV3 | 2.643 | 6.744 | 1.802 |
| TRGV8/TRDV2 | 1.971 | 5.388 | 1.44 |
| TRGV5/TRDV1 | 1.871 | 3.633 | 0.9711 |
| TRGV2/TRDV2 | 1.871 | 3.633 | 0.9711 |
| TRGV8/TRDV3 | 1.643 | 4.557 | 1.218 |
| TRGV2/TRAV29/DV5 | 1.492 | 4.706 | 1.305 |
| TRGV3/TRDV2 | 1.279 | 2.922 | 0.7808 |
| TRGV10/TRDV1 | 1.071 | 2.31 | 0.6175 |
| TRGV9/TRAV38-2/DV8 | 0.3571 | 1.336 | 0.3571 |
| TRGV4/TRDV2 | 0.1857 | 0.6949 | 0.1857 |
| TRGV9/TRAV29/DV5 | 0.1714 | 0.6414 | 0.1714 |

Example 3

Establishment of Human TCRαβ and TCRγδ Retroviral Expression Clone Library

Many of the downstream applications of paired TCRαβ or TCRγδ sequence analysis require cloning and expression of the antigen specific receptors for immunological studies such as structural and functional characterization, biochemical characterization, epitope identification, and gene therapy[18,29,30]. Thus, a rapid cloning method was developed to improve on conventional restriction enzyme-mediated ligation techniques, which can be cumbersome and time consuming. In addition, use of restriction enzymes for cloning becomes problematic because of the potential occurrences of restriction sites in some variable regions and the non-germline CDR3 sequences of the TCR chains. The vector used for TCR expression is pMICherry, which has been successfully used to construct TCR clones for the generation of retrogenic mice[31,32]. A schematic diagram of the cloned TCR chains in the pMICherry vector is shown in FIG. 2A.

To clone full length TCR chains, a TRGV9/TRDV2 clone was chosen to demonstrate the feasibility of the cloning system, since the TRGV9/TRDV2 clonotype is dominant in the TCRγδ repertoire analysis from human PBMCs (FIG. 1C). Similarly, a human TCRαβ pair was chosen derived from an influenza-specific CD8 T cell from an infected individual. Using the IMGT-reported human TRGV, TRDV, TRGC, and TRDC sequences for TCRγδ or human TRAV, TRBV, TRAC and TRBC sequences for TCRαβ and the single cell CDR3γ and δ or CDR3α and β sequence data full length TCRγ and δ chains and TCRα and β chains were constructed and joined by the 2A "self-cleaving" site in silico. 2A oligopeptides can interact with the ribosomal exit tunnel to terminate sequence translation at the final codon (Pro) of the 2A sequence, and reinitiate translation of the following sequence[33]. Multi-cistronic 2A based retroviral vectors have been used for TCR:CD3 structural and functional studies[32,34-38]. The entire sequence of TCRγ-2A-TCRδ along with an 25 bp overhang complementary to the ends of the linearized pMICherry vector were synthesized in two fragments of approximately 1 kb each as gBlock® DNA fragments (IDT) with an internal 25 bp overlap in the 2A segment. By using Gibson Assembly® Master Mix, the two gBlocks spanning the TCRγ-2A-TCRδ were ligated with the linearized vector in a three-way ligation. The process of cloning is shown in FIG. 2A. After this cloning procedure, an average of 70.9% of the colonies picked after transformation was entirely matched with target sequences. The others contained either point mutations resulting from the cloning process or no inserts. More than 30 different TCR constructs have been cloned by using this system, including, mouse and human TCR αβ and TCRγδ. The cloning system is highly reproducible.

To test the functionality of the TCR clones that were made following the method described in FIG. 2A, the human TRGV9/TRDV2 construct was transfected into the Jurkat 76 TCRα$^-$β$^-$ cell line and checked for the cell surface expression by anti-TCRγδ and anti-CD3 antibody staining and flow cytometry. Although Jurkat cells have endogenous CD3, the expression of TCRγδ was not robust. Since γδ T cells do not develop in CD3-deficient mice and patients[39] the human CD3 complex was cloned into an MSCV vector (pMIAmetrine) and co-transfected it with the human TCR constructs. mCherry and ametrine are the reporter genes in the pMICherry vector with human TCR genes and the pMIAmetrine vector with human CD3 genes, respectively. It is demonstrated that co-transfection of the human CD3 construct with the human TCRγδ and chains can improve the surface expression level of TCR in a Jurkat cell line (FIG. 6). 3.76% of cells were double positive for mCherry and ametrine, and 19.5% of double-positive cells were TCRγδ and CD3 positive, which proved the functionality of the cloning and expression platform of the invention (top panel, FIG. 2B). The expression of the influenza virus-specific TCRαβ was analyzed by staining the transfected cells with APC-conjugated influenza-M1 tetramer (HLA-A*0201, GILGFVFTL (SEQ ID NO: 146)) and CD3 antibody. The FACS plot shows 5.03% of transfected cells were double positive for mCherry and ametrine, 16.1% of which were positive for tetramer staining (bottom panel, FIG. 2B).

Example 4

Effective TCR Activation Reporting by Nur77-GFP Jurkat 76 TCRα$^-$β$^-$ Cells

An important application of TCR cloning and expression is to screen molecules that can activate or inhibit TCR signaling. Thus far, the common methods to detect TCR activation are using ELISA to detect cytokines (e.g. IFNγ) in the cell culture medium[21,22], intracellular staining to report cytokine production by flow cytometry, or qRT-PCR to quantify the mRNA expression of cytokines, which are time-consuming, labor-intensive, and expensive. In the present invention, a TCR activation reporter cell line, Nur77-GFP Jurkat 76 TCRα$^-$β$^-$ (NJ76 cells) was established by stably transducing Nur77-GFP BAC DNA into Jurkat 76 TCRα$^-$β$^-$ cells. The Nur77-GFP reporting system has been demonstrated to reflect specific TCR signal strength by GFP expression[40,41,42].

Figure 3A:
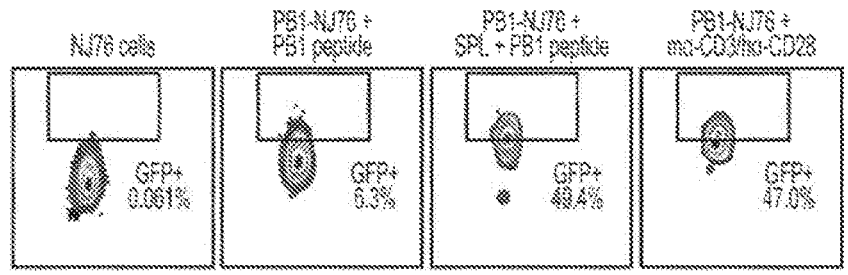
FIG. 3A illustrates how Nur77-GFP Jurkat 76 TCRα⁻β⁻ cells can report the TCR signaling activation. Following co-transfection of a murine $K^bPB1_{703}$-specific TCRαβ derived from influenza-infected mice and a mouse CD3 construct, the $K^bPB1_{703}^+$TCRαβ⁺ NJ76 cells (PB1-NJ76) were stimulated either with influenza $PB1_{703}$ peptide alone or $PB1_{703}$ peptide-pulsed splenotytes for 4 hrs. Anti-mouse CD3/α-human CD28 stimulation was also done as a positive control. The GFP expression was assessed by flow cytometry.
Figure 3B:
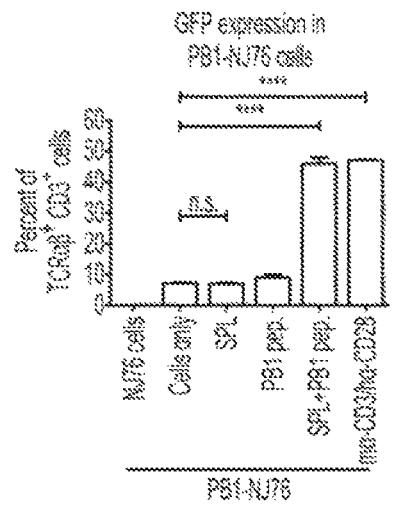
In FIG. 3B, the quantification of GFP expression in PB1-NJ76 cells is shown. Statistical differences were determined by One-way ANOVA.
Figure 7:
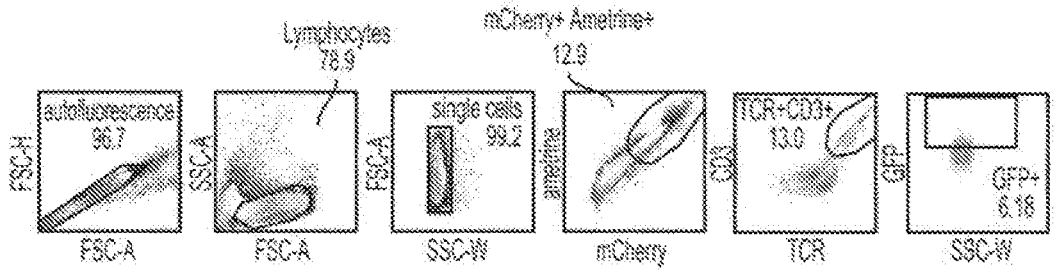
FIG. 7 shows a gating strategy of TCR-transfected-NJ76 cells in flow cytometry. The data of TCR-transfected-NJ76 cells after stimulation in FIGS. 3A-3C were analyzed by applying the gating strategy to all the samples. The gating is flowing "autofluorescence gate–lymphocytes gate–single cell gate–mCherry+Ametrine+ gate–TCR+CD3+ gate–GFP+ gate".

To test the functionality of NJ76 cells in reporting TCR activation, NJ76 cells were transfected with a murine K$^b$PB1$_{703}$-specific TCRαβ derived from influenza-infected mice along with a mouse CD3 construct. The K$^b$PB1$_{703}$$^+$ TCRαβ$^+$ NJ76 cells (PB1-NJ76) were incubated with mouse splenocytes, the influenza PB1$_{703}$ peptide, splenotytes and peptide, or mouse α-CD3/human α-CD28 as a positive control for 4 hours and GFP expression in transfected NJ76 cells was detected by flow cytometry (FIG. 3A). The quantification of GFP levels is shown in FIG. 3B. The results show that PB1-NJ76 cells can robustly express GFP after specific peptide stimulation (PB1) with antigen-presenting cells. The gating strategy for GFP detection is shown in FIG. 7.

Figure 3C:
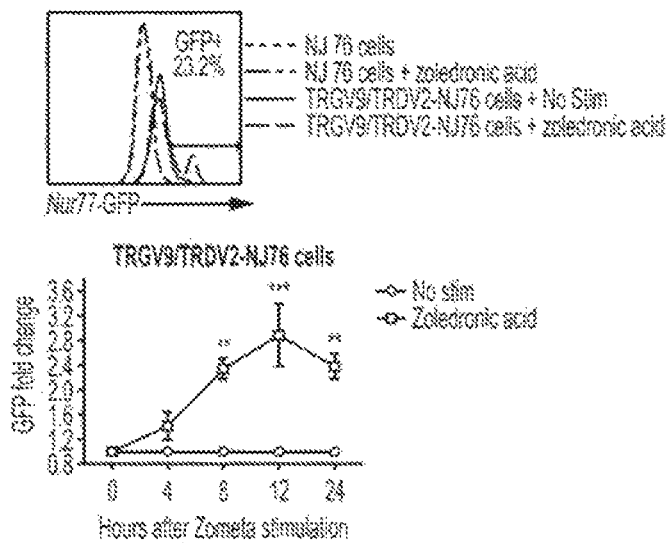
In FIG. 3C, the transfected human TRGV9/TRDV2-NJ76 cells were pulsed with zoledronic acid (50 ug/ml) for 3 h at 37° C., and washed and incubated at 37° C. for 12 h. The GFP expression of stimulated NJ76 cells, non-stimulated TRGV9/TRDV2-NJ76 and stimulated TRGV9/TRDV2-NJ76 cells with zoledronic acid is shown in the top panel. Fold change of GFP expression in stimulated TRGV9/TRDV2-NJ76 cells with zoledronic acid compared to non-stimulated TRGV9/TRDV2-NJ76 is shown as a time course in the bottom panel. Statistical differences were determined by Two-way ANOVA; $p<0.05$ was considered statistically significant. Data are mean±SEM of two independent experiments. $p<0.01$, *$p<0.001$, ****$p<0.0001$, n.s. non-significant.

This TCR-activation reporting system has also been tested for TCRγδ signaling. Zoledronic acid (Zometa, Novartis) is an aminobisphosphonate that has demonstrated antitumor effects via inhibition of tumor growth and angiogenesis and induction of malignant cell apoptosis in humans[43,44,45]. In addition, zoledronic acid can specifically stimulate and expand human TRGV9/TRDV2 cells[46,47,48,49]. Since it can result in the accumulation of upstream metabolites in the mevalonate pathway, e.g. IPP, which induce the expansion of γδ T cells in vitro and in vivo, zoledronic acid pre-treatment can increase the cytolysis of some cancer cell lines by γδ T cells[50]. After transfection of the human TRGV9/TRDV2 vector and human CD3 vector into NJ76 cells, the transfected TRGV9/TRDV2-NJ76 cells were pulsed with 50 μg/ml of zoledronic acid for 3 hours, and washed and incubated the cells at 37° C. for 12 h. The GFP expression level was quantified in transfected TRGV9/TRDV2-NJ76 cells and control cells by flow cytometry. The Nur77-GFP expression level is shown in FIG. 3C (top panel). The transfected TRGV9/TRDV2-NJ76 cells showed a significantly higher level of GFP expression, which demonstrates that zoledronic acid can trigger γδ TCR signaling for the stimulation and expansion of γδ T cells. The fold change of GFP expression over time in stimulated TRGV9/TRDV2-NJ76 cells with zoledronic acid and non-stimulated TRGV9/TRDV2-NJ76 is shown in FIG. 3C (bottom panel).

Example 5

Effective TCR Activation Reporting by Nur77-Luc Jurkat 76 TCRα$^-$β$^-$ Cells

Nur77-GFP BAC DNA was modified by using recombineering to substitute the GFP with firefly luciferase. In particular, recombineering was undertaken to insert a cassette with Luciferase-SV40pA-PGK-Neo-bGHpA into the Nur77 gene. A clone with such insertion (Nur77-Luc BAC DNA) was isolated and sequenced. TCRα$^-$β$^-$ Jurkat 76 cells were transfected with the Nur77-Luc BAC DNA under a selectively complete RPMI medium with 500 μg/ml of Genetcin, yielding Nur77-Luciferase TCRα$^-$β$^-$ Jurkat cells.

To determine optimum conditions for luciferase assays, tests of various numbers of Nur77-Luciferase TCRα$^-$β$^-$ Jurkat cells per well were undertaken. In the tests, the cells were subjected to four hours of PMA/Ionomycin stimulation followed by measurement in a luciferase reader. These values are shown in Table 5 under the column "Stimulated". As a control, the luciferase reader was used to measure cells that were not stimulated. See Table 5, "Unstimulated" column. By comparison, the medium itself gave values of only 0 to 80 in the luciferase reader.

TABLE 5

Luciferase assay of various amounts of Nur77-Luciferase TCRα$^-$β$^-$ Jurkat cells

| Cell number | Unstimulated | Stimulated |
| --- | --- | --- |
| 1 × 10$^4$ | 2640 | 9600 |
| 2.5 × 10$^4$ | 4400 | 19680 |

TABLE 5-continued

Luciferase assay of various amounts of Nur77-Luciferase TCRα⁻β⁻ Jurkat cells

| Cell number | Unstimulated | Stimulated |
|---|---|---|
| $5 \times 10^4$ | 8640 | 37360 |
| $1 \times 10^5$ | 16400 | 62400 |
| $2.5 \times 10^5$ | 34560 | 97840 |
| $5 \times 10^5$ | 41520 | 49520 |
| $1 \times 10^6$ | 39440 | 32880 |

When assaying luciferase, using a cell number of $1 \times 10^5$ provides a four-fold rise in luciferase activity as compared with the unstimulated cells.

Example 6

Rapid TCR Cloning by CDR3 Substitution Using Overlap Extension PCR and TCR Library For TCRs, the only hypervariable regions are the CDR3 regions. Thus, cloning full length TCRs de novo for each application may expend unnecessary resources. To improve on this, a library was generated containing potential TRGV and TRDV "backbone" combinations that only require the swapping of individual CDR3 regions directly from PCR products. For example, in TRGV9/TRDV2 cells from PBMCs of healthy donors, the CDR3s of both γ and δ chains were found to be highly diverse (Table 4). To rapidly generate an array of TRGV9/TRDV2 clones with diverse CDR3γ and δ, a DNA linker, whose ends overlap with the TRGC and TRDV2 of the single cell PCR products, was designed. Similarly for other combinations of the TRGV/TRDV family several DNA linkers were designed. These DNA linkers contain the TRGC region, 2A and one of the TRDV regions, as is shown in FIG. 4. By overlap PCR with the single cell PCR products, DNA linkers, TRGV sense primers, and TRDC antisense primers, any pair of TCRγδ can be connected together. Next, the first-step PCR products were used as a mega primer with the appropriate clone from the library (e.g., TRGV9/TRDV2 with an irrelevant CDR3) as a template for the second-step overlap extension PCR. By using this substitution method, different γδ TCRs with matched CDR3s from the human single cell PCR products were successfully cloned. The same approach could be used with αβ TCRs, although the clone library would be larger. This CDR3 substitution approach can shorten the cloning process to within 5 days (FIG. 4).

TABLE 6

CDR3 amino acid sequences of paired human TRGV9/TRDV2 cells isolated from PBMCs (n = 14)

| Paired amino acid sequence in TRGV9-CDR3 region | Paired amino acid sequence in TRDV2-CDR3 region | Frequency |
|---|---|---|
| ALFIQELGKKIKV (SEQ ID NO: 58) | ACDVLGDTEGRLI (SEQ ID NO: 59) | 2 |
| ALWDGPYYKKL (SEQ ID NO: 60) | ACDTVFTGGYSSWDTRQMF (SEQ ID NO: 61) | 2 |
| ALWDIPPGQELGKKIKV (SEQ ID NO: 62) | ACDTLGETSSWDTRQMF (SEQ ID NO: 63) | 2 |
| ALWEAQELGKKIKV (SEQ ID NO: 64) | ACDSGGYSSWDTRQMF (SEQ ID NO: 65) | 2 |
| ALWEARQELGKKIKV (SEQ ID NO: 66) | ACDTLFPGGSATDKLI (SEQ ID NO: 67) | 2 |
| ALWEGTRGQELGKKIKV (SEQ ID NO: 68) | ACDTVGAHTDKLI (SEQ ID NO: 69) | 2 |
| ALWEVGDQELGKKIKV (SEQ ID NO: 70) | ACDPLNTGGSFSLYTDKLI (SEQ ID NO: 71) | 2 |
| ALWEVHSELGKKIKV (SEQ ID NO: 72) | ACDTGGFRSSWDTRQMF (SEQ ID NO: 73) | 2 |
| ALWEVHSELGKKIKV (SEQ ID NO: 72) | ACDTGGFRSSWDTRQMF (SEQ ID NO: 73) | 2 |
| ALWEVLELGKKIKV (SEQ ID NO: 74) | ACDTVGMGIRLGDKLI (SEQ ID NO: 75) | 2 |
| ALWEVLVGELGKKIKV (SEQ ID NO: 76) | ACDILGINTDKLI (SEQ ID NO: 77) | 2 |
| ALWEVPELGKKIKV (SEQ ID NO: 78) | ACERLGDYVPDKLI (SEQ ID NO: 79) | 2 |
| ALWEVQELGKKIKV (SEQ ID NO: 80) | ACDRLLGDTDKLI (SEQ ID NO: 81) | 2 |
| ALWEVQELGKKIKV (SEQ ID NO: 80) | ACDTVAPRIGGLKYTDKLI (SEQ ID NO: 82) | 2 |
| ALWEVQELGKKIKV (SEQ ID NO: 80) | ACDTVGGPYTDKLI (SEQ ID NO: 83) | 2 |
| ALWEVQELGKKIKV (SEQ ID NO: 80) | ACDTVGGTAQ (SEQ ID NO: 84) | 2 |
| ALWEVQELGKKIKV (SEQ ID NO: 80) | ACDTVSGGSTPTWYTDKLI (SEQ ID NO: 85) | 2 |
| ALWEVQELGKKIKV (SEQ ID NO: 80) | ACDTVSIFTGDTTDKLI (SEQ ID NO: 86) | 2 |
| ALWEVRELGKKIKV (SEQ ID NO: 87) | ACDTILIFSPTGGDTDKLI (SEQ ID NO: 88) | 2 |
| ALWEVRELGKKIKV (SEQ ID NO: 87) | ACVPLGDWTDKLI (SEQ ID NO: 89) | 2 |
| ALWEVRKQELGKKIKV (SEQ ID NO: 90) | ACDTLGDDFDKLI (SEQ ID NO: 91) | 2 |
| ALWEVTHNRQELGKKIKV (SEQ ID NO: 92) | ACDTLLGTEAWDTRQMF (SEQ ID NO: 93) | 2 |

TABLE 6-continued

CDR3 amino acid sequences of paired human
TRGV9/TRDV2 cells isolated from PBMCs (n = 14)

| Paired amino acid sequence in TRGV9-CDR3 region | Paired amino acid sequence in TRDV2-CDR3 region | Frequency |
| --- | --- | --- |
| ALWGGAAGAYYKKL (SEQ ID NO: 94) | ACDGKTTDTDKLI (SEQ ID NO: 95) | 2 |
| ALWGGELGKKIKV (SEQ ID NO: 96) | ACDLLGDTRYTDKLI (SEQ ID NO: 97) | 2 |
| ALWVQELGKKIKV (SEQ ID NO: 98) | ACVGITGDTDKLI (SEQ ID NO: 99) | 2 |
| ALWEAHQELGKKIKV (SEQ ID NO: 100) | ACDSLGDSVDKLI (SEQ ID NO: 101) | 1 |
| ALWEANKKL (SEQ ID NO: 102) | ACDLLRGAGGQIDKLI (SEQ ID NO: 103) | 1 |
| ALWEAQELGKKIKV (SEQ ID NO: 104) | ACDTVGGAFDTDKLI (SEQ ID NO: 105) | 1 |
| ALWEATGLGKKIKV (SEQ ID NO: 106) | ACDMGDTRSWDTRQMF (SEQ ID NO: 107) | 1 |
| ALWEDLELGKKIKV (SEQ ID NO: 108) | ACDTVSWGKNTDKLI (SEQ ID NO: 109) | 1 |
| ALWEKEELGKKIKV (SEQ ID NO: 110) | ACDTGDWGSSWDTRQMF (SEQ ID NO: 111) | 1 |
| ALWEKELGKKIKV (SEQ ID NO: 112) | ACDILDSTGGTDLTAQLF (SEQ ID NO: 113) | 1 |
| ALWEMTQELGKKIKV (SEQ ID NO: 114) | ACDTVRNTGGYAFAGIDKLI (SEQ ID NO: 115) | 1 |
| ALWEPQELGKKIKV (SEQ ID NO: 116) | ACDKVLGDSSWDTRQMF (SEQ ID NO: 117) | 1 |
| ALWESKELGKKIKV (SEQ ID NO: 118) | ACEGLGATQSSWDTRQMF (SEQ ID NO: 119) | 1 |
| ALWEVGELGKKIKV (SEQ ID NO: 120) | ACDKLLGDNELI (SEQ ID NO: 121) | 1 |
| ALWEVHKLGKKIKV (SEQ ID NO: 122) | ACDSLLGKGTDKLI (SEQ ID NO: 123) | 1 |
| ALWEVKELGKKIKV (SEQ ID NO: 124) | ACDTLRGSADKLI (SEQ ID NO: 125) | 1 |
| ALWEVLQQELGKKIKV (SEQ ID NO: 126) | ACDTVPARHTDKLI (SEQ ID NO: 127) | 1 |
| ALWEVPVLGKKIKV (SEQ ID NO: 128) | ACDTADRSSYTDKLI (SEQ ID NO: 129) | 1 |
| ALWEVQELGKKIKV (SEQ ID NO: 80) | ACDTLLGDPSSSWDTRQMF (SEQ ID NO: 130) | 1 |
| ALWEVQELGKKIKV (SEQ ID NO: 80) | ACDTLSGGYARTDKLI (SEQ ID NO: 131) | 1 |
| ALWEVQELGKKIKV (SEQ ID NO: 80) | ACDTVGILGDTGLGLI (SEQ ID NO: 132) | 1 |
| ALWEVRELGKKIKV (SEQ ID NO: 87) | ACDTIVSGYDGYDKLI (SEQ ID NO: 133) | 1 |
| ALWEVRELGKKIKV (SEQ ID NO: 87) | ACSILGDKTSDKLI (SEQ ID NO: 134) | 1 |
| ALWEVRQELGKKIKV (SEQ ID NO: 135) | ACDTVSQRGGYSDKLI (SEQ ID NO: 136) | 1 |
| ALWEVRVQELGKKIKV (SEQ ID NO: 137) | ACDPLERVGGPANTDKLI (SEQ ID NO: 138) | 1 |
| ALWEVTELGKKIKV (SEQ ID NO: 139) | ACDVLGDTGDDKLI (SEQ ID NO: 140) | 1 |
| ALWGRELGKKIKV (SEQ ID NO: 141) | ACDTVGSNTDKLI (SEQ ID NO: 142) | 1 |
| ALWVQELGKKIKV (SEQ ID NO: 98) | ACDVLGDTEADKLI (SEQ ID NO: 143) | 1 |
| ALYGSPSGEELGKKNQG (SEQ ID NO: 144) | ACDPLEGAGGHNTDKLI (SEQ ID NO: 145) | 1 |

TABLE 7

Sequences of primers to mouse sequences used in nested RT-PCR.
(All primers are forward primers except two sequences indicated with "reverse" which represents reverse primers. External primers were used in the first round while internal ones were used in the second round of PCR.)

| Primer name | External | SEQ ID | Internal | SEQ ID |
|---|---|---|---|---|
| TRGV1-3 | GCAGCTGGAGCAAACTG | 147 | CTGAATTATCGGTCACCAG | 148 |
| TRGV4 | CAAATATCCTGTAAAGTTTTCATC | 149 | GTTTAGAGTTTCTATTATATGTCCTTGCAAC | 150 |
| TRGV5 | GATATCTCAGGATCAGCTCTCC | 151 | TACCCGAAGACCAAACAAGAC | 152 |
| TRGV6 | TCACCTCTGGGGTCATATG | 153 | AGAGGAAAGGAAATACGGC | 154 |
| TRGV7 | CAACTTGGAAGAAAGAATAATGTC | 155 | CACCAAGCTAGAGGGGTC | 156 |
| TRGC (reverse) | CTTTTCTTTCCAATACACCC | 157 | TCDGGAAAGAACTTTTCAAGG | 158 |
| TRDV1 | ACCCAAATGTTGCATCAG | 159 | GTCTCTGACAATCCAAGAAGG | 160 |
| TRDV2 | TCTGTGCAGGTGGCAG | 161 | CCCTGGACTGCACCTATG | 162 |
| TRDV4 | TGTATATTTGGAACCAGTTGC | 163 | GATCCTGCCTCCTTCTACTG | 164 |
| TRDV5 | CATCACGCTGACCCAG | 165 | GCTCCACTGACCAGACAG | 166 |
| TRDV6/ TRAV15 | CASCTTYTTAGTGGAGAGATGG | 167 | AYTCTGTAGTCTTCCAGAAATCAC | 168 |
| TRDV7/ TRAV13 | TCCTTGGTTCTGCAGG | 169 | TGCAGGAGGGGAGA | 170 |
| TRDV8/ TRAV14 | GCAGCAGGTGAGACAAAG | 171 | CTCTGACAGTCTGGGAAGG | 172 |
| TRDV9/ TRAV6-1/ 6-2 | CAGATGCAAGGTCAAGTGAC | 173 | GGAGAAGGTCCACAGCTC | 174 |
| TRDV9/ TRAV6-3/ 6-4 | AAGGTCCACAGCTCCTTC | 175 | CAACTGCCAACAACAAGG | 176 |
| TRDV9/ TRAV6-5/ 6-7 | GTTCTGGTATGTGCAGTATCC | 177 | TCCTTCCACTTGCAGAAAG | 178 |
| TRDV10/ TRAV4 | TCTGSTCTGAGATGCAATTTT | 179 | GGITIMAGGAACAAAGGAGAAT | 180 |
| TRDV11/ TRAV16 | GTACAAGCAAACAGCAAGTG | 181 | ATTATTCTCTGAACTTTCAGAAGC | 182 |
| TRDV12/ TRAV21 | GTGCACTTGCCTTGTAGC | 183 | AATAGTATGGCTTTCCTGGC | 184 |
| TRDC (reverse) | TGAAAGAATTTGCATATGGTTC | 185 | GAGATGACTATAGCAGGGTCG | 186 |

Tables 8-11: "Partial" V and C regions amplified depending on the target sequence. (Column "Region" discloses nucleotide sequence positions based on the IMGT reference database, see Lefranc, M. -P., The Immunologist, 7, 132-136 (1999) and www.imgt.org/IMGTScientificChart/Nomenclature/IMGT-FRCDRdefinition.html.)

TABLE 8

Human γδ primer list with positions.

| Primer name | SEQ ID NO: | Primer Sequence | Region |
|---|---|---|---|
| HuTRDV4/TRAV14Ext | 27 | CAAACCCAACCAGGAATG | 76 . . . 93 |
| HuTRDV6/TRAV2Ext | 31 | TTGATAGTCCAGAAAGGAGG | 115 . . . 134 |
| HuTRDV/TRAV29Ext | 29 | GCAAGTTAAGCAAAATTCACC | 84 . . . 104 |
| HuTRDV7/TRAVExt | 33 | GACAAGGTGGTACAAAGCC | 67 . . . 85 |
| HuTRDV8/TRAVExt | 35 | CAGTCACTCAGTCTCAACCAG | 68 . . . 88 |
| HuTRDV1Ext | 21 | GCCCAGAAGGTTACTCAAG | 61 . . . 79 |
| HuTRDV2Ext | 23 | ATTGAGTTGGTGCCTGAAC | 61 . . . 79 |
| HuTRDV3Ext | 25 | TGTGACAAAGTAACCCAGAGTTC | 52 . . . 74 |
| HuTRDCExt | 37 | CTTCATATTTACCAAGCTTGACAG | 196-173 |
| HuTRDV4/TRAV14Int | 28 | AGGAAAAGGAGGCTGTGAC | 101 . . . 119 |
| HuTRDV6/TRAV2Int | 32 | CGTTTGACTACTTTCCATGG | 170 . . . 189 |
| HuTRDV/TRAV29Int | 30 | CTGCTGAAGGTCCTACATTC | 197 . . . 216 |
| HuTRDV7/TRAVInt | 34 | ATCTCTGGTTGTCCACGAG | 90 . . . 108 |
| HuTRDV8/TRAVInt | 36 | TCTGGTACAAGCAGCCTC | 164 . . . 181 |
| HuTRDV1Int | 22 | AGCAAAGAGATGATTTTCCTTA | 184 . . . 205 |
| HuTRDV2Int | 24 | TATATCAACTGGTACAGGAAGACC | 157 . . . 180 |
| HuTRDV3Int | 26 | GGTACTGCTCTGCACTTACGAC | 108 . . . 129 |
| HuTRDCInt | 38 | GATGACAATAGCAGGATCAAAC | 150-129 |
| HuTRGV10Ext | 13 | TTATCAAAAGTGGAGCAGTTC | 52 . . . 72 |
| HuTRGV11Ext | 15 | GAACAACCTGAAATATCTATTTCC | 61 . . . 84 |
| HuTRGV3.5Ext | 1 | TCTTCCAACTTGGAAGGG | 55 . . . 72 |
| HuTRGV8Ext | 9 | CCAACTTGGAAGGGAGAAC | 59 . . . 77 |
| HuTRGV1.2.4.6Ext | 17 | GGGTCATCTGCTGAAATCAC | 100 . . . 119 |
| HuTRGV9Ext | 11 | cCAGGTCACCTAGAGCAAC | 61 . . . 79 |
| HuTRGVAExt | 5 | GGGTCATCCTGTTTCCAG | 26 . . . 43 |
| HuTRGVBExt | 7 | TGGCCTCCCAAAGTACTG | 18 . . . 35 |
| HuTRGCExt | 19 | GGTGTTCCCCTCCTGG | 186-171 |
| HuTRGV10Int | 14 | CAGCTATCCATTTCCACGG | 73 . . . 91 |
| HuTRGV11Int | 16 | CATATCTTGGAAGGCATCC | 108 . . . 126 |
| HuTRGV3.5Int | 2 | GGTCATCTGCTGAAATCAC | 101 . . . 119 |
| HuTRGV1.2.4.6Int | 18 | CCAGGAGGGGAAGGC | 168 . . . 182 |
| HuTRGV8Int | 10 | AAAATGCCGTCTACACCC | 83 . . . 100 |
| HuTRGV9Int | 12 | TGTCCATTTCATATGACGG | 209 . . . 227 |
| HuTRGCInt | 20 | CCCAGAATCGTGTTGCT | 167-151 |

TABLE 9

Mouse αβ primer list with positions (V region external and C region reverse primers and their positions).

| Primer name | SEQ ID NO: | Primer Sequence | Region |
|---|---|---|---|
| mTRBV1Ext | 187 | TACCACGTGGTCAAGCTG | 101 . . . 118 |
| mTRBV12Ext | 188 | GGGGTTGTCCAGTCTCC | 94 . . . 110 |
| mTRBV13Ext | 189 | GCTGCAGTCACCCAAAG | 55 . . . 71 |
| mTRBV16Ext | 190 | CCTAGgcACAAGGTGACAG | 73 . . . 91 |
| mTRBV14Ext | 191 | GCAGTCCTACAGGAAGGG | 88 . . . 105 |
| mTRBV15Ext | 192 | GAGTTACCCAGACACCCAG | 65 . . . 83 |
| mTRBV17Ext | 193 | GAAGCCAAACCAAGCAC | 168 . . . 184 |
| mTRBV19Ext | 194 | GATTGGTCAGGAAGGGC | 99 . . . 115 |

TABLE 9-continued

Mouse αβ primer list with positions
(V region external and C region reverse primers and their positions).

| Primer name | SEQ ID NO: | Primer Sequence | Region |
|---|---|---|---|
| mTRAV2Ext | 195 | cATcTACTGGTACCGACAGG | 159 ... 178 |
| mTRBV2Ext | 196 | CAGTATCTAGGCCACAATGC | 130 ... 149 |
| mTRBV20Ext | 197 | GGATGGAGTGTCAAGCTG | 101 ... 118 |
| mTRBV23Ext | 198 | CTGCAGTTACACAGAAGCC | 62 ... 80 |
| mTRBV24Ext | 199 | CAGACTCCACGATACCTGG | 73 ... 91 |
| mTRBV29Ext | 200 | GCTGGAATGTGGACAGG | 117 ... 133 |
| mTRBV3Ext | 201 | CCCAAAGTCTTACAGATCCC | 61 ... 80 |
| mTRBV31Ext | 202 | CTAACCTCTACTGGTACTGGCAG | 143 ... 165 |
| mTRBV4Ext | 203 | GACGGCTGTTTTCCAGAC | 60 ... 77 |
| mTRBV5Ext | 204 | GGTATAAACAGAGCGCTGAG | 155 ... 174 |
| Cba Rev Ext | 205 | CCAGAAGGTAGCAGAGACCC | 252-233 |
| mTRBV1Int | 206 | GTATCCCTGGATGAGCTG | 150 ... 167 |
| mTRBV12Int | 207 | CCAGCAGATTCTCAGTCC | 269 ... 286 |
| mTRBV13Int | 208 | GTACTGGTATCGGCAGGAC | 147 ... 165 |
| mTRBV14Int | 209 | GGTATCAGCAGCCCAGAG | 158 ... 175 |
| mTRBV15Int | 210 | GTGTGAGCCAGTTTCAGG | 123 ... 140 |
| mTRBV16Int | 211 | GAAGCAACTCTGTGGTGTG | 109 ... 127 |
| mTRBV17Int | 212 | GAACAGGGAAGCTGACAC | 219 ... 236 |
| mTRBV19Int | 213 | GGTACCGACAGGATTCAG | 167 ... 184 |
| mTRBV2Int | 214 | GGACAATCAGACTGCCTC | 222 ... 239 |
| mTRBV20Int | 215 | GCTTGGTATCGTCAATCG | 142 ... 159 |
| mTRBV23Int | 216 | GCCAGGAAGCAGAGATG | 104 ... 120 |
| mTRBV26Int | 217 | GAggTGTATCCCTGAAAAGG | 120 ... 139 |
| mTRBV24Int | 218 | GCACACTGCCTTTTACTGG | 141 ... 159 |
| mTRBV29Int | 219 | GTACTGGTATCGACAAGACCC | 153 ... 173 |
| mTRBV3Int | 220 | GATATGGGGCAGATGGTG | 97 ... 114 |
| mTRBV31Int | 221 | CTGTTGGCCAGGTAGAGTC | 206 ... 224 |
| mTRBV5Int | 222 | GCCAGAGCTCATGTTTCTC | 180 ... 198 |
| Cbb Rev Int | 223 | GGGTAGCCTTTTGTTTGTTTG | 88-68 |
| mTRAV10.10aInt | 224 | CTACACTGAGTGTTCGAGAGG | 89 ... 109 |
| mTRAV12Int | 225 | GGTTCCACGCCACTC | 242 ... 256 |
| mTRAV13Int | 170 | TGCAGGAGGGGGAGA | 98 ... 112 |
| mTRAV14Int | 172 | CTCTGACAGTCTGGGAAGG | 113 ... 131 |
| mTRAV15Int | 168 | AYTCTGTAGTCTTCCAGAAATCAC | 251 ... 274 |
| mTRAV16Int | 182 | ATTATTCTCTGAACTTTCAGAAGC | 248 ... 271 |
| mTRAV17Int | 226 | TATGAAGGAGCCTCCCTG | 97 ... 114 |
| mTRAV18Int | 227 | CAAGATTTCACCGCACG | 103 ... 119 |
| mTRAV19Int | 228 | GCTGACTGTTCAAGAGGGA | 108 ... 126 |
| mTRAV1Int | 229 | CTCCACATTCCTGAGCC | 237 ... 253 |
| mTRAV21Int | 184 | AATAGTATGGCTTTCCTGGC | 220 ... 239 |
| mTRAV2Int | 230 | ACTCTGAGCCTGCCCT | 265 ... 280 |
| mTRAV4Int | 180 | GGiTiMAGGAACAAAGGAGAAT | 210 ... 231 |

TABLE 9-continued

Mouse αβ primer list with positions
(V region external and C region reverse primers and their positions).

| Primer name | SEQ ID NO: | Primer Sequence | Region |
|---|---|---|---|
| mTRAV5-15-4Int | 315 | ATYCGTTCAAATATGGAAAGAAA | 211 . . . 233 |
| mTRAV6-16-2Int | 174 | GGAGAAGGTCCACAGCTC | 178 . . . 195 |
| mTRAV6-36-4Int | 176 | CAACtGCCAACAACAAGG | 209 . . . 226 |
| mTRAV6-36-4Int-1 | 176 | CAACtGCCAACAACAAGG | 209 . . . 226 |
| mTRAV6-56-7Int | 178 | TCCTTCCACTTGCAGAAAG | 271 . . . 289 |
| mTRAV6-6Int | 231 | ACGGCTGGCCAGAAG | 217 . . . 231 |
| mTRAV8Int | 232 | AGAGCCACCCTTGACAC | 244 . . . 260 |
| mTRAV9Int | 233 | GCTTYGAGGCTGAGTTCAG | 239 . . . 257 |
| mTRAC Rev Int | 234 | GCACATTGATTTGGGAGTC | 100-82 |
| mTRAV1010aExt | 235 | AGAGAAGGTCGAGCAACAC | 66 . . . 84 |
| mTRAV11Ext | 236 | AAGACCCAAGTGGAGCAG | 64 . . . 81 |
| mTRAV12Ext | 237 | TGACCCAGACAGAAGGC | 68 . . . 84 |
| mTRAV13Ext | 169 | TCCTTGGTTCTGCAGG | 88 . . . 103 |
| mTRAV14Ext | 171 | GCAGCAGGTGAGACAAAG | 87 . . . 104 |
| mTRAV19Ext | 238 | gcAAGttAaAcAAAGCTCTCC | 286 . . . 306 |
| mTRBV31Ext | 202 | ctaACcTCtacTGGTACTGGCAG | 176 . . . 198 |
| mTRAV15Ext | 167 | CASCTTYTTAGTGGAGAGATGG | 175 . . . 196 |
| mTRAV16Ext | 181 | GTACAAGCAAACAGCAAGTG | 168 . . . 187 |
| mTRAV17Ext | 239 | CAGTCCGTGGACCAGC | 61 . . . 76 |
| mTRAV6-56-7Ext | 177 | gTTCTGGTAtGTGCAGTATCC | 156 . . . 176 |
| mTRAV18Ext | 240 | AACGGCTGGAGCAGAG | 59 . . . 74 |

TABLE 9-continued

Mouse αβ primer list with positions
(V region external and C region reverse primers and their positions).

| Primer name | SEQ ID NO: | Primer Sequence | Region |
|---|---|---|---|
| mTRAV2Ext | 195 | caTcTACTGGTACCGACAGG | 147 . . . 166 |
| mTRAV21Ext | 183 | GTGCACTTGCCTTGTAGC | 103 . . . 120 |
| mTRAV3Ext | 241 | GGCGAGCAGGTGGAG | 64 . . . 78 |
| mTRAV5-15-4Ext | 242 | GgcTACTTCCcTtGGTATAAGCAAGA | 154 . . . 179 |
| mTRAV4Ext | 179 | TcTGSTCTGAGATGCAATTTT | 113 . . . 133 |
| mTRAV6-36-4Ext | 175 | AAGGTCCACAGCTCCTTC | 182 . . . 199 |
| mTRAV6-36-4Ext-1 | 175 | AAGGTCCACAGCTCCTTC | 182 . . . 199 |
| mTRAV6-6Ext | 243 | AGATTCCGTGACTCAAACAG | 60 . . . 79 |
| mTRAV7Ext | 244 | AGAAGGTRCAGCAGAGCCCAGAATC | 65 . . . 89 |
| mTRAV8Ext | 245 | GAGCRTCCASGAGGGTG | 93 . . . 109 |
| mTRAV9Ext | 246 | CCAGTGGTTCAAGGAGTG | 217 . . . 234 |
| mTRAC Rev Ext | 247 | GGCATCACAGGGAACG | 276-261 |

TABLE 10

Human αβ primer list with positions
(internal forward V region and reverse C region specific primers and their positions).

| Primer name | SEQ ID NO: | Primer Sequence | Region |
|---|---|---|---|
| huTRAV34int | 248 | aTcTCaccATAAACTGCACG | 101 . . . 120 |
| huTRAV1int | 249 | GCACCCACATTTCTKTCTTAC | 175 . . . 195 |
| huTRAV10int | 250 | GAAAGAACTGCACTCTTCAATG | 110 . . . 131 |
| huTRAV12-1 | 251 | AAGATGGAAGGTTTACAGCAC | 230 . . . 250 |
| huTRAV13-1int | 252 | TCAGACAGTGCCTCAAACTAC | 133 . . . 153 |
| huTRAV13-2int | 253 | CAGTGAAACATCTCTCTCTGC | 266 . . . 286 |
| huTRAV14int | 254 | AGGCTGTGACTCTGGACTG | 110 . . . 128 |
| huTRAV16int | 255 | GTCCAGTACTCCAGACAACG | 166 . . . 185 |
| huTRAV17int | 256 | CCACCATGAACTGCAGTTAC | 116 . . . 135 |
| huTRAV18int | 257 | TGACAGTTCCTTCCACCTG | 261 . . . 279 |

TABLE 10-continued

Human αβ primer list with positions
(internal forward V region and reverse C region specific primers and their positions).

| Primer name | SEQ ID NO: | Primer Sequence | Region |
|---|---|---|---|
| huTRAV19int | 258 | TGTGACCTTGGACTGTGTG | 114 . . . 132 |
| huTRAV2int | 259 | CACTCTGTGTCCAATGCTTAC | 145 . . . 165 |
| huTRAV20int | 260 | TCTGGTATAGGCAAGATCCTG | 164 . . . 184 |
| huTRAV21int | 261 | AACTTGGTTCTCAACTGCAG | 109 . . . 128 |
| huTRAV22int | 262 | CTGACTCTGTGAACAATTTGC | 137 . . . 157 |
| huTRBV3int | 263 | aATctTcaCAtCAATTCCCTG | 185 . . . 205 |
| huTRAV23int | 264 | TGCATTATTGATAGCCATACG | 216 . . . 236 |
| huTRAV24int | 265 | TGCCTTACACTGGTACAGATG | 159 . . . 179 |
| huTRAV25int | 266 | TATAAGCAAAGGCCTGGTG | 157 . . . 175 |
| huTRAV26-1int | 267 | CGACAGATTCACTCCCAG | 160 . . . 177 |
| huTRAV26-2int | 268 | TTCACTTGCCTTGTAACCAC | 104 . . . 123 |
| huTRAV27int | 269 | CTCACTGTGTACTGCAACTCC | 109 . . . 129 |
| huTRAV29int | 30 | CTGCTGAAGGTCCTACATTC | 197 . . . 216 |
| huTRAV3int | 270 | ATGCACCTATTCAGTCTCTGG | 123 . . . 143 |
| huTRAV8-24int | 271 | AGAGtgAAACCTCCTTCCAC | 263 . . . 282 |
| huTRAV30int | 272 | AGAAGCATGGTGAAGCAC | 170 . . . 187 |
| huTRAV35int | 273 | ACCTGGCTATGGTACAAGC | 145 . . . 163 |
| huTRAV36int | 34 | ATCTCTGGTTGTCCACGAG | 90 . . . 108 |
| huTRAV38int | 274 | CAGCAGGCAGATGATTCTC | 183 . . . 201 |
| huTRAV39int | 275 | TCAACCACTTCAGACAGACTG | 130 . . . 150 |
| huTRAV4int | 276 | ATTATATCACGTGGTACCAACAG | 143 . . . 165 |
| huTRAV40int | 277 | GGAGGCGGAAATATTAAAGAC | 226 . . . 246 |
| huTRAV41int | 278 | TTGTTTATGCTGAGCTCAGG | 202 . . . 221 |
| huTRAV5int | 279 | TACACAGACAGCTCCTCCAC | 133 . . . 152 |
| huTRAV6int | 280 | TGGTACCGACAAGATCCAG | 163 . . . 181 |
| huTRAV7int | 281 | TATGAGAAGCAGAAAGGAAGAC | 226 . . . 247 |
| huTRAV8-1int | 282 | GTCAACACCTTCAGCTTCTC | 179 . . . 198 |
| huTRAV8-7int | 283 | ATCAgaGGtTTTGAGGCTG | 235 . . . 253 |
| huTRAV8-6int | 284 | AACcAAGGACTCCAGCTTC | 178 . . . 196 |
| huTRAV8-3int | 285 | TTTGAGGCTGAATTTAAGAGG | 244 . . . 264 |
| huTRAV9-1 | 286 | GAAACCACTTCTTTCCACTTG | 262 . . . 282 |
| huTRAC Rev INT | 287 | TGTTGCTCTTGAAGTCCATAG | 181-160 |
| huTRBV10-1int | 288 | TGGTATCGACAAGACCTGG | 157 . . . 175 |
| huTRBV10-2int | 288 | TGGTATCGACAAGACCTGG | 157 . . . 175 |
| huTRBV10-3int | 289 | GGAACACCAGTGACTCTGAG | 103 . . . 122 |

TABLE 10-continued

Human αβ primer list with positions
(internal forward V region and reverse C region specific primers and their positions).

| Primer name | SEQ ID NO: | Primer Sequence | Region |
|---|---|---|---|
| huTRBV11int | 290 | GACTCCACTCTCAAGATCCA | 277 . . . 296 |
| huTRBV12int | 291 | CYACTCTgARGATCCAGCC | 281 . . . 299 |
| huTRBV13int | 292 | CATTCTGAACTGAACATGAGC | 304 . . . 324 |
| huTRBV5-1 | 293 | CTTGGAGCTGGRSGACTC | 327 . . . 344 |
| huTRBV14int | 294 | ATTCTACTCTGAAGGTGCAGC | 278 . . . 298 |
| huTRBV15int | 295 | ATAACTTCCAATCCAGGAGG | 242 . . . 261 |
| huTRAV4int | 276 | aTTATaTcacgTGGTACCAACAG | 146 . . . 168 |
| huTRBV16int1 | 296 | CTGTAGCCTTGAGATCCAGG | 279 . . . 298 |
| huTRBV17int | 297 | TGTTCACTGGTACCGACAG | 150 . . . 168 |
| huTRBV18int | 298 | CGATTTTCTGCTGAATTTCC | 247 . . . 266 |
| huTRBV19int | 299 | TTCCTCTCACTGTGACATCG | 278 . . . 297 |
| huTRBV2int | 300 | TTCACTCTGAAGATCCGGTC | 280 . . . 299 |
| huTRBV20int | 301 | ACTCTGACAGTGACCAGTGC | 307 . . . 326 |
| huTRBV23int | 302 | GCAATCCTGTCCTCAGAAC | 289 . . . 307 |
| huTRBV24int | 303 | GATGGATACAGTGTCTCTCGA | 241 . . . 261 |
| huTRAV6int | 280 | TGGTAcCgACAAGATCCAG | 157 . . . 175 |
| huTRBV25int | 304 | CAGAGAAGGGAGATCTTTCC | 221 . . . 240 |
| huTRBV2728int | 305 | TTCYCCCTGATYCTGGAGTC | 277 . . . 296 |
| huTRBV29int | 306 | TCTGACTGTGAGCAACATGAG | 276 . . . 296 |
| huTRBV3int | 263 | AATCTTCACATCAATTCCCTG | 280 . . . 300 |
| huTRBV30int | 307 | AGAATCTCTCAGCCTCCAGAC | 236 . . . 256 |
| huTRBV4int | 308 | CCTGCAGCCAGAAGACTC | 297 . . . 314 |
| huTRBV5-5 | 309 | TCTGAGCTGAATGTGAACG | 277 . . . 295 |
| huTRBV6-1 | 310 | GTGTRCCCAGGATATGAACC | 123 . . . 142 |
| huTRBV6-4int | 311 | TGGTTATAGTGTCTCCAGAGC | 243 . . . 263 |
| huTRBV7-1 | 312 | TCYACTCTGAMGWTCCAGCG | 280 . . . 299 |
| huTRBV9int | 313 | GTACCAACAGAGCCTGGAC | 159 . . . 177 |
| huTRBC Rev Int | 314 | TTCTGATGGCTCAAACACAG | 54-35 |

TABLE 11

Mouse γδ primer list with positions.

| Primer name | SEQ ID NO: External | SEQ ID NO: Internal | Region |
|---|---|---|---|
| TRGV1-3 | 147 GCAGCTGGAGCAAACTG | 148 CTGAATTATCGGTCACCAG | 68-86 |
| TRGV4 | 149 CAAATATCCTGTAAGTTTTCATC | 150 GTTTAGAGTTTCTATTATATGTCCTTGCAAC | 251-281 |

TABLE 11-continued

Mouse γδ primer list with positions.

| Primer name | SEQ ID NO: | External | SEQ ID NO: | Internal | Region |
|---|---|---|---|---|---|
| TRGV5 | 151 | GATATCTCAGGAT CAGCTCTCC | 152 | TACCCGAAGACCA AACAAGAC | 81-101 |
| TRGV6 | 153 | TCACCTCTGGGGT CATATG | 154 | AGAGGAAAGGAAA TACGGC | 137-155 |
| TRGV7 | 155 | CAACTTGGAAGAA AGAATAATGTC | 156 | CACCAAGCTAGAG GGGTC | 87-104 |
| TRGC (reverse) | 157 | CTTTTCTTTCCAA TACACCC | 158 | TCDGGAAAGAACT TTTCAAGG | 118-98 |
| TRDV1 | 159 | ACCCAAATGTTGC ATCAG | 160 | GTCTCTGACAATC CAAGAAGG | 87-107 |
| TRDV2 | 161 | TCTGTGCAGGTGG CAG | 162 | CCCTGGACTGCAC CTATG | 119-136 |
| TRDV4 | 163 | TGTATATTTGGAA CCAGTTGC | 164 | GATCCTGCCTCCT TCTACTG | 106-125 |
| TRDV5 | 165 | CATCACGCTGACC CAG | 166 | GCTCCACTGACCA GACAG | 71-88 |
| TRDV6/ TRAV15 | 167 | CASCTTYTTAGTG GAGAGATGG | 168 | AYTCTGTAGTCTT CCAGAAATCAC | 251-274 |
| TRDV7/ TRAV13 | 169 | TCCTTGGTTCTGC AGG | 170 | TGCAGGAGGGGA GA | 98-112 |
| TRDV8/ TRAV14 | 171 | GCAGCAGGTGAGA CAAAG | 172 | CTCTGACAGTCTG GGAAGG | 113-131 |
| TRDV9/ TRAV6-1/ 6-2 | 173 | CAGATGCAAGGTC AAGTGAC | 174 | GGAGAAGGTCCAC AGCTC | 178-195 |
| TRDV9/ TRAV6-3/ 6-4 | 175 | AAGGTCCACAGCT CCTTC | 176 | CAACTGCCAACAA CAAGG | 209-226 |
| TRDV9/ TRAV6-5/ 6-7 | 177 | GTTCTGGTATGTG CAGTATCC | 178 | TCCTTCCACTTGC AGAAAG | 271-289 |
| TRDV10/ TRAV4 | 179 | TCTGSTCTGAGAT GCAATTTT | 180 | GGITIMAGGAACA AAGGAGAAT | 210-231 |
| TRDV11/ TRAV16 | 181 | GTACAAGCAAACA GCAAGTG | 182 | ATTATTCTCTGAA CTTTCAGAAGC | 248-271 |
| TRDV12/ TRAV21 | 183 | GTGCACTTGCCTT GTAGC | 184 | AATAGTATGGCTT TCCTGGC | 220-239 |
| TRDC (reverse) | 185 | TGAAAGAATTTTG CATATGGTTC | 186 | GAGATGACTATAG CAGGGTCG | 151-131 |

REFERENCES

1. Restifo, N P, Dudley, M E and Rosenberg, S A (2012). Adoptive immunotherapy for cancer: harnessing the T cell response. *Nat. Rev. Immunol.* 12: 269-281.
2. Rosenberg, S A and Restifo, N P (2015). Adoptive cell transfer as personalized immunotherapy for human cancer. *Science* 348: 62-68.
3. Wherry, E J, Ha, S-J, Kaech, S M, Haining, W N, Sarkar, S, Kalia, V, et al. (2007). Molecular Signature of CD8+ T Cell Exhaustion during Chronic Viral Infection. *Immunity* 27: 670-684.
4. Baitsch, L, Baumgaertner, P, Devêvre, E, Raghav, S K, Legat, A, Barba, L, et al. (2011). Exhaustion of tumor-specific CD8+ T cells in metastases from melanoma patients. *J. Clin. Invest.* 121: 2350-2360.
5. Wherry, E J and Kurachi, M (2015). Molecular and cellular insights into T cell exhaustion. *Nat. Rev. Immunol.* 15: 486-499.
6. Besser, M J, Shapira-Frommer, R, Itzhaki, O, Treves, A J, Zippel, D B, Levy, D, et al. (2013). Adoptive Transfer of Tumor-Infiltrating Lymphocytes in Patients with Metastatic Melanoma: Intent-to-Treat Analysis and Efficacy after Failure to Prior Immunotherapies. *Clin. Cancer Res.* 19: 4792-4800.
7. Klaver, Y, Kunert, A, Sleijfer, S, Debets, R and Lamers, C H (2015). Adoptive T-cell therapy: a need for standard immune monitoring. *Immunotherapy* 7: 513-533.
8. Lamers, C H J, Willemsen, R, van Elzakker, P, van Steenbergen-Langeveld, S, Broertjes, M, Oosterwijk-Wakka, J, et al. (2011). Immune responses to transgene and retroviral vector in patients treated with ex vivo-engineered T cells. *Blood* 117: 72-82.
9. Chapuis, A G, Thompson, J A, Margolin, K A, Rodmyre, R, Lai, I P, Dowdy, K, et al. (2012). Transferred melanoma-specific CD8+ T cells persist, mediate tumor regression, and acquire central memory phenotype. *Proc. Natl. Acad. Sci. U.S.A.* 109: 4592-4597.
10. Han, E Q, Li, X, Wang, C, Li, T and Han, S (2013). Chimeric antigen receptor-engineered T cells for cancer immunotherapy: progress and challenges. *J Hematol. Oncol. J Hematol Oncol* 6: 47.
11. Hinrichs, C S, Borman, Z A, Cassard, L, Gattinoni, L, Spolski, R, Yu, Z, et al. (2009). Adoptively transferred effector cells derived from naïve rather than central memory CD8+ T cells mediate superior antitumor immunity. *Proc. Natl. Acad. Sci. U.S.A.* 106: 17469-17474.
12. Kershaw, M H, Westwood, J A, Parker, L L, Wang, G, Eshhar, Z, Mavroukakis, S A, et al. (2006). A Phase I Study on Adoptive Immunotherapy Using Gene-Modified T Cells for Ovarian Cancer. *Clin. Cancer Res.* 12: 6106-6115.
13. Ramos, C A and Dotti, G (2011). Chimeric antigen receptor (CAR)-engineered lymphocytes for cancer therapy. *Expert Opin. Biol. Ther.* 11: 855-873.
14. Varela-Rohena, A, Carpenito, C, Perez, E E, Richardson, M, Parry, R V, Milone, M, et al. (2008). Genetic engineering of T cells for adoptive immunotherapy. *Immunol. Res.* 42: 166-181.
15. Schmitt, T M, Ragnarsson, G B and Greenberg, P D (2009). T Cell Receptor Gene Therapy for Cancer. *Hum. Gene Ther.* 20: 1240-1248.
16. Stauss, H J, Morris, E C and Abken, H (2015). Cancer gene therapy with T cell receptors and chimeric antigen receptors. *Curr. Opin. Pharmacol.* 24: 113-118.
17. Schmitt, T M, Stromnes, I M, Chapuis, A G and Greenberg, P D (2015). New Strategies in Engineering T-cell Receptor Gene-Modified T Cells to More Effectively Target Malignancies. *Clin. Cancer Res.* : clincanres.0860.2015doi:10.1158/1078-0432. CCR-15-0860.
18. Vavassori, S, Kumar, A, Wan, G S, Ramanjaneyulu, G S, Cavallari, M, Daker, S El, et al. (2013). Butyrophilin 3A1 binds phosphorylated antigens and stimulates human γδ T cells. *Nat. Immunol.* 14: 908-916.
19. Birnbaum, M E, Mendoza, J L, Sethi, D K, Dong, S, Glanville, J, Dobbins, J, et al. (2014). Deconstructing the peptide-MHC specificity of T cell recognition. *Cell* 157: 1073-1087.

20. Luoma, A M, Castro, C D, Mayassi, T, Bembinster, L A, Bai, L, Picard, D, et al. (2013). Crystal structure of Vδ1 T cell receptor in complex with CD1d-sulfatide shows MHC-like recognition of a self-lipid by human γδ T cells. *Immunity* 39: 1032-1042.
21. Linnemann, C, Heemskerk, B, Kvistborg, P, Kluin, R J C, Bolotin, D A, Chen, X, et al. (2013). High-throughput identification of antigen-specific TCRs by TCR gene capture. *Nat. Med.* 19: 1534-1541.
22. Kobayashi, E, Mizukoshi, E, Kishi, H, Ozawa, T, Hamana, H, Nagai, T, et al. (2013). A new cloning and expression system yields and validates TCRs from blood lymphocytes of patients with cancer within 10 days. *Nat. Med.* 19: 1542-1546.
23. Howie, B, Sherwood, A M, Berkebile, A D, Berka, J, Emerson, R O, Williamson, D W, et al. (2015). High-throughput pairing of T cell receptor α and β sequences. *Sci. Transl. Med.* 7: 301ra131.
24. Perko, R, Kang, G, Sunkara, A, Leung, W, Thomas, P G and Dallas, M R (2015). Gamma Delta T Cell Reconstitution Is Associated with Fewer Infections and Improved Event-Free Survival after Hematopoietic Stem Cell Transplantation for Pediatric Leukemia. *Biol. Blood Marrow Transplant.* 21: 130-136.
25. Silva-Santos, B, Serre, K and Norell, H (2015). γδ T cells in cancer. *Nat. Rev. Immunol. advance online publication*.
26. Dash, P, McClaren, J L, Oguin, T H, Rothwell, W, Todd, B, Morris, M Y, et al. (2011). Paired analysis of TCRα and TCRβ chains at the single-cell level in mice. *J. Clin. Invest.* 121: 288-295.
27. Wang, G C, Dash, P, McCullers, J A, Doherty, P C and Thomas, P G (2012). T cell receptor αβ diversity inversely correlates with pathogen-specific antibody levels in human cytomegalovirus infection. *Sci. Transl. Med.* 4: 128ra42.
28. Bryksin, A V and Matsumura, I (2010). Overlap extension PCR cloning: a simple and reliable way to create recombinant plasmids. *BioTechniques* 48: 463-465.
29. Uldrich, A P, Le Nours, J, Pellicci, D G, Gherardin, N A, McPherson, K G, Lim, R T, et al. (2013). CD1d-lipid antigen recognition by the γδ TCR. *Nat. Immunol.* 14: 1137-1145.
30. Yoshio Ogawa, M N (2013). Gamma-delta T Cells may Function as Carrier Vehicles in Adenovirus Vector-based Gene Therapy. *J. Cancer Sci. Ther.* 05.
31. (2006). Generation of T-cell receptor retrogenic mice: Article: Nature Protocols. *Nat Protoc.* 1: 406-417.
32. Bettini, M L, Bettini, M, Nakayama, M, Guy, C S and Vignali, D A A (2013). Generation of T cell receptor-retrogenic mice: improved retroviral-mediated stem cell gene transfer. *Nat. Protoc.* 8: 1837-1840.
33. Sharma, P, Yan, F, Doronina, V A, Escuin-Ordinas, H, Ryan, M D and Brown, J D (2012). 2A peptides provide distinct solutions to driving stop-carry on translational recoding. *Nucleic Acids Res.* 40: 3143-3151.
34. Holst, J, Szymczak-Workman, A L, Vignali, K M, Burton, A R, Workman, C J and Vignali, D A A (2006). Generation of T-cell receptor retrogenic mice. *Nat. Protoc.* 1: 406-417.
35. Szymczak, A L, Workman, C J, Wang, Y, Vignali, K M, Dilioglou, S, Vanin, E F, et al. (2004). Correction of multi-gene deficiency in vivo using a single 'self-cleaving' 2A peptide-based retroviral vector. *Nat. Biotechnol.* 22: 589-594.
36. Bettini, M L, Bettini, M and Vignali, D A A (2012). T-cell receptor retrogenic mice: a rapid, flexible alternative to T-cell receptor transgenic mice. *Immunology* 136: 265-272.
37. Day, E B, Guillonneau, C, Gras, S, La Gruta, N L, Vignali, D A A, Doherty, P C, et al. (2011). Structural basis for enabling T-cell receptor diversity within biased virus-specific CD8+ T-cell responses. *Proc. Natl. Acad. Sci. U.S.A.* 108: 9536-9541.
38. Bartok, I, Holland, S J, Kessels, H W, Silk, J D, Alkhinji, M and Dyson, J (2010). T cell receptor CDR3 loops influence alphabeta pairing. *Mol. Immunol.* 47: 1613-1618.
39. Siegers, G M, Swamy, M, Fernandez-Malavé, E, Minguet, S, Rathmann, S, Guardo, A C, et al. (2007). Different composition of the human and the mouse γδ T cell receptor explains different phenotypes of CD3γ and CD3δ immunodeficiencies. *J. Exp. Med.* 204: 2537-2544.
40. Moran, A E, Holzapfel, K L, Xing, Y, Cunningham, N R, Maltzman, J S, Punt, J, et al. (2011). T cell receptor signal strength in Treg and iNKT cell development demonstrated by a novel fluorescent reporter mouse. *J. Exp. Med.* 208: 1279-1289.
41. Gao, P, Han, X, Zhang, Q, Yang, Z, Fuss, I J, Myers, T G, et al. (2014). Dynamic changes in E-protein activity regulate T reg cell development. *J. Exp. Med.* 211: 2651-2668.
42. Au-Yeung, B B, Zikherman, J, Mueller, J L, Ashouri, J F, Matloubian, M, Cheng, D A, et al. (2014). A sharp T-cell antigen receptor signaling threshold for T-cell proliferation. *Proc. Natl. Acad. Sci.* 111: E3679-E3688.
43. Peng, H, Sohara, Y, Moats, R A, Nelson, M D, Groshen, S G, Ye, W, et al. (2007). The Activity of Zoledronic Acid on Neuroblastoma Bone Metastasis Involves Inhibition of Osteoclasts and Tumor Cell Survival and Proliferation. *Cancer Res.* 67: 9346-9355.
44. Backman, U, Svensson, Å, Christofferson, R H and Azarbayjani, F (2008). The Bisphosphonate, Zoledronic Acid Reduces Experimental Neuroblastoma Growth by Interfering with Tumor Angiogenesis. *Anticancer Res.* 28: 1551-1557.
45. Gnant, M and Clézardin, P (2012). Direct and indirect anticancer activity of bisphosphonates: A brief review of published literature. *Cancer Treat. Rev.* 38: 407-415.
46. Di Carlo, E, Bocca, P, Emionite, L, Cilli, M, Cipollone, G, Morandi, F, et al. (2013). Mechanisms of the Antitumor Activity of Human Vγ9Vδ2 T Cells in Combination With Zoledronic Acid in a Preclinical Model of Neuroblastoma. *Mol. Ther.* 21: 1034-1043.
47. Goto, H, Matsuda, K, Srikoon, P, Kariya, R, Hattori, S, Taura, M, et al. (2013). Potent antitumor activity of zoledronic acid-induced Vγ9Vδ2 T cells against primary effusion lymphoma. *Cancer Lett.* 331: 174-182.
48. Sprini, D, Di Stefano, L, Rini, G B, Cianferotti, L and Napoli, N (2014). Vγ9Vδ2 T lymphocytes activation in osteoporotic patients treated with bisphosphonates. *Clin. Cases Miner. Bone Metab.* 11: 126-128.
49. Wada, I, Matsushita, H, Noji, S, Mori, K, Yamashita, H, Nomura, S, et al. (2014). Intraperitoneal injection of in vitro expanded Vγ9Vδ2 T cells together with zoledronate for the treatment of malignant ascites due to gastric cancer. *Cancer Med.* 3: 362-375.
50. Suzuki, T, Terao, S, Acharya, B, Naoe, M, Yamamoto, S, Okamura, H, et al. (2010). The Antitumour Effect of γδ T-Cells is Enhanced by Valproic Acid-induced Up-regulation of NKG2D Ligands. *Anticancer Res.* 30: 4509-4513.

51. Pardoll, D M (2012). The blockade of immune checkpoints in cancer immunotherapy. *Nat. Rev. Cancer* 12: 252-264.
52. Dudley, M E, Wunderlich, J R, Shelton, T E, Even, J and Rosenberg, S A (2003). Generation of Tumor-Infiltrating Lymphocyte Cultures for Use in Adoptive Transfer Therapy for Melanoma Patients. *J. Immunother. Hagerstown Md* 1997 26: 332-342.
53. Chien, Y, Meyer, C and Bonneville, M (2014). γδ T Cells: First Line of Defense and Beyond. *Annu. Rev. Immunol.* 32: 121-155.
54. Gros, A, Robbins, P F, Yao, X, Li, Y F, Turcotte, S, Tran, E, et al. (2014). PD-1 identifies the patient-specific CD8+ tumor-reactive repertoire infiltrating human tumors. *J. Clin. Invest.* 124: 2246-2259.
55. Downing, J R, Wilson, R K, Zhang, J, Mardis, E R, Pui, C-H, Ding, L, et al. (2012). The Pediatric Cancer Genome Project. *Nat. Genet.* 44: 619-622.
56. Robinson, G, Parker, M, Kranenburg, T A, Lu, C, Chen, X, Ding, L, et al. (2012). Novel mutations target distinct subgroups of medulloblastoma. *Nature* 488: 43-48.
57. Zhang, J, Benavente, C A, McEvoy, J, Flores-Otero, J, Ding, L, Chen, X, et al. (2012). A novel retinoblastoma therapy from genomic and epigenetic analyses. *Nature* 481: 329-334.
58. Zhang, J, Ding, L, Holmfeldt, L, Wu, G, Heatley, S L, Payne-Turner, D, et al. (2012). The genetic basis of early T-cell precursor acute lymphoblastic leukaemia. *Nature* 481: 157-163.
59. Barrett, A J and Bollard, C M (2015). The coming of age of adoptive T-cell therapy for viral infection after stem cell transplantation. *Ann. Transl. Med.* 3.
60. Saglio, F, Hanley, P J and Bollard, C M (2014). The time is now: moving toward virus-specific T cells after allogeneic hematopoietic stem cell transplantation as the standard of care. *Cytotherapy* 16: 149-159.
61. Vantourout, P and Hayday, A (2013). Six-of-the-best: unique contributions of γδ cells to immunology. *Nat. Rev. Immunol.* 13: 88-100.
62. Lefranc, M-P, Giudicelli, V, Ginestoux, C, Jabado-Michaloud, J, Folch, G, Bellahcene, F, et al. (2009). IMGT, the international ImMunoGeneTics information system. *Nucleic Acids Res.* 37: D1006-1012.
63. Bell, J (2008). A simple way to treat PCR products prior to sequencing using ExoSAP-IT. *BioTechniques* 44: 834.
64. Workman, C J, Dugger, K J and Vignali, D A A (2002). Cutting Edge: Molecular Analysis of the Negative Regulatory Function of Lymphocyte Activation Gene-3. *J. Immunol.* 169: 5392-5395.
65. Persons, D A, Allay, J A, Allay, E R, Smeyne, R J, Ashmun, R A, Sorrentino, B P, et al. (1997). Retroviral-Mediated Transfer of the Green Fluorescent Protein Gene Into Murine Hematopoietic Cells Facilitates Scoring and Selection of Transduced Progenitors In Vitro and Identification of Genetically Modified Cells In Vivo. *Blood* 90: 1777-1786.
66. Heemskerk, M H M, Hoogeboom, M, Paus, R A de, Kester, M G D, van der Hoorn, M A W G, Goulmy, E, et al. (2003). Redirection of antileukemic reactivity of peripheral T lymphocytes using gene transfer of minor histocompatibility antigen HA-2-specific T-cell receptor complexes expressing a conserved alpha joining region. *Blood* 102: 3530-3540.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

LIST OF SEQUENCES

HuTRGV3.5
External Primer:
(SEQ ID NO: 1)
5'TCTTCCAACTTGGAAGGG3'

Internal Primer:
(SEQ ID NO: 2)
5'GGTCATCTGCTGAAATCAC3'

HuTRGV7
External Primer:
(SEQ ID NO: 3)
5'TCTTCCAACTTGCAAGGG3'

Internal Primer:
(SEQ ID NO: 4)
5'GGTCATCTGCTGTAATCACTTG3'

HuTRGVA
External Primer:
(SEQ ID NO: 5)
5'GGGTCATCCTGTTTCCAG3'

Internal Primer:
(SEQ ID NO: 6)
5'TACCTAAGGACCTGTGTAGAGG3'

HuTRGVB
External Primer:
(SEQ ID NO: 7)
5'TGGCCTCCCAAAGTACTG3'

Internal Primer:
(SEQ ID NO: 8)
5'TCCTCTTTCTATGTCCCAGG3'

HuTRGV8
External Primer:
(SEQ ID NO: 9)
5'CCAACTTGGAAGGGAGAAC3'

Internal Primer:
(SEQ ID NO: 10)
5'AAAATGCCGTCTACACCC3'

HuTRGV9
External Primer:
(SEQ ID NO: 11)
5'CCAGGTCACCTAGAGCAAC3'

Internal Primer:
(SEQ ID NO: 12)
5'TGTCCATTTCATATGACGG3'

HuTRGV10
External Primer:
(SEQ ID NO: 13)
5'TTATCAAAAGTGGAGCAGTTC3'

Internal Primer:
(SEQ ID NO: 14)
5'CAGCTATCCATTTCCACGG3'

HuTRGV11
External Primer:
(SEQ ID NO: 15)
5'GAACAACCTGAAATATCTATTTCC3'

LIST OF SEQUENCES

Internal Primer:
(SEQ ID NO: 16)
5'CATATCTTGGAAGGCATCC3'

HuTRGV1.2.4.6
External Primer:
(SEQ ID NO: 17)
5'GGGTCATCTGCTGAAATCAC3'

Internal Primer:
(SEQ ID NO: 18)
5'CCAGGAGGGGAAGGC3'

HuTRGC
External Primer:
(SEQ ID NO: 19)
5'GGTGTTCCCCTCCTGG3'

Internal Primer:
(SEQ ID NO: 20)
5'CCCAGAATCGTGTTGCT3'

HuTRDV1
External Primer:
(SEQ ID NO: 21)
5'GCCCAGAAGGTTACTCAAG3'

Internal Primer:
(SEQ ID NO: 22)
5'AGCAAAGAGATGATTTTCCTTA3'

HuTRDV2
External Primer:
(SEQ ID NO: 23)
5'ATTGAGTTGGTGCCTGAAC3'

Internal Primer:
(SEQ ID NO: 24)
5'TATATCAACTGGTACAGGAAGACC3'

HuTRDV3
External Primer:
(SEQ ID NO: 25)
5'TGTGACAAAGTAACCCAGAGTTC3'

Internal Primer:
(SEQ ID NO: 26)
5'GGTACTGCTCTGCACTTACGAC3'

HuTRDV4/TRAV14
External Primer:
(SEQ ID NO: 27)
5'CAAACCCAACCAGGAATG3'

Internal Primer:
(SEQ ID NO: 28)
5'AGGAAAAGGAGGCTGTGAC3'

HuTRDV5/TRAV29
External Primer:
(SEQ ID NO: 29)
5'GCAAGTTAAGCAAAATTCACC3'

Internal Primer:
(SEQ ID NO: 30)
5'CTGCTGAAGGTCCTACATTC3'

HuTRDV6/TRAV23
External Primer:
(SEQ ID NO: 31)
5'TTGATAGTCCAGAAAGGAGG3'

Internal Primer:
(SEQ ID NO: 32)
5'CGTTTGACTACTTTCCATGG3'

HuTRDV7/TRAV36
External Primer:
(SEQ ID NO: 33)
5'GACAAGGTGGTACAAAGCC3'

Internal Primer:
(SEQ ID NO: 34)
5'ATCTCTGGTTGTCCACGAG3'

HuTRDV8/TRAV38-2
External Primer:
(SEQ ID NO: 35)
5'CAGTCACTCAGTCTCAACCAG3'

Internal Primer:
(SEQ ID NO: 36)
5'TCTGGTACAAGCAGCCTC3'

HuTRDC
External Primer:
(SEQ ID NO: 37)
5'CTTCATATTTACCAAGCTTGACAG3'

Internal Primer:
(SEQ ID NO: 38)
5'GATGACAATAGCAGGATCAAAC3'

CD3δ sense
(SEQ ID NO: 39)
5'CCCTCACTCCTTCTCTAGGCGCCGGAATTCGCCAGGATGGAACATAGCACG3'

CD3δ antisense
(SEQ ID NO: 40)
5'CCACGTCTCCCGCCAACTTGAGAAGGTCAAAATTCAAAGTCTGTTTCACCGGTCCCTTGTTCCGAGCC3'

CD3γ sense
(SEQ ID NO: 41)
5'GAATTTTGACCTTCTCAAGTTGGCGGGAGACGTGGAGTCCAACCCAGGGCCCATGGAACAGGGGAAG3'

CD3γ antisense
(SEQ ID NO: 42)
5'CCTCGACGTCACCGCATGTTAGCAGACTTCCTCTGCCCTCAGATCTTCTATTCCTCCTCAAC3'

CD3ε sense
(SEQ ID NO: 43)
5'CAGAGGAAGTCTGCTAACATGCGGTGACGTCGAGGAGAATCCTGGCCCAATGCAGTCGGGCACTC3'

CD3ε antisense
(SEQ ID NO: 44)
5'GTTTTCTTCCACGTCTCCTGCTTGCTTTAACAGAGAGAAGTTCGTGGCGGATCCTCCGATGCGTCTCTG3'

CD3ζ sense
(SEQ ID NO: 45)
5'CTCTCTGTTAAAGCAAGCAGGAGACGTGGAAGAAAACCCCGGTCCCATGAAGTGGAAAGTG3'

CD3ζ antisense
(SEQ ID NO: 46)
5'GAGGGAGAGGGGCGGAATTGATCCTCGAGCAATTGTTAGCGAGGGGCCAG3'

2A amino acid sequence F2A (foot-and-mouth disease virus)
(SEQ ID NO: 47)
VKQTLNFDLLKLAGDVESNPGP 2A amino acid sequence T2A (Thosea asigna virus)
(SEQ ID NO: 48)
EGRGSLLTCGDVEENPGP

LIST OF SEQUENCES 2A amino acid sequence P2A (porcine teschovirus-1)
(SEQ ID NO: 49)
ATNFSLLKQAGDVEENPGP HuLinkerDV1
(SEQ ID NO: 50)
5'catacattgtatcttgagaaattttcccagatattattaagatacat
tggcaagaaaagaagagcaacacgattctgggatcccaggaggggaacac
catgaagactaacgacacatacatgaaatttagctggttaacggtgccag
aagagtcactggacaaagaacacagatgtatcgtcagacatgagaataat
aaaaacggaattgatcaagaaattatctttcctccaataaagacagatgt
catcacaatggatcccaaagacaattggtcaaaagatgcaaatgatacac
tactgctgcagctcacaaacacctctgcatattacatgtacctcctcctg
ctcctcaagagtgtggtctattttgccatcatcacctgctgtctgatgga
agaacggattctgctgcaatggagagaaatcaGCCACGAACTTCTCTCTG
TTAAAGCAAGCAGGAGACGTGGAAGAAAACCCCGGTCCCATGCTGTTCTC
CAGCCTGCTGTGTGTATTTGTGGCCTTCAGCTACTCTGGATCAAGTGTGG
CCCAGAAGGTTACTCAAGCCCAGTCATCAGTATCCATGCCAGTGAGGAAA
GCAGTCACCCTGAACTGCCTGTATGAAACAAGTTGGTGGTCATATTATAT
TTTTTGGTACAAGCAACTTCCCAGCAAAGAGATGATTTTCCTTATTCGC
C3'

HuLinkerDV2
(SEQ ID NO: 51)
5'catacattgtatcttgagaaattttcccagatattattaagatacat
tggcaagaaaagaagagcaacacgattctgggatcccaggaggggaacac
catgaagactaacgacacatacatgaaatttagctggttaacggtgccag
aagagtcactggacaaagaacacagatgtatcgtcagacatgagaataat
aaaaacggaattgatcaagaaattatctttcctccaataaagacagatgt
catcacaatggatcccaaagacaattggtcaaaagatgcaaatgatacac
tactgctgcagctcacaaacacctctgcatattacatgtacctcctcctg
ctcctcaagagtgtggtctattttgccatcatcacctgctgtctgatgga
agaacggattctgctgcaatggagagaaatcaGCCACGAACTTCTCTCTG
TTAAAGCAAGCAGGAGACGTGGAAGAAAACCCCGGTCCCATGCAGAGGAT
CTCCTCCCTCATCCATCTCTCTCTTCTGGGCAGGAGTCATGTCAGCCA
TTGAGTTGGTGCCTGAACACCAAACAGTGCCTGTGTCAATAGGGGTCCCT
GCCACCCTCAGGTGCTCCATGAAAGGAGAAGCGATCGGTAACTACTATAT
CAACTGGTACAGGAAGACCCAAGG3'

HuLinkerDV3
(SEQ ID NO: 52)
5'catacattgtatcttgagaaattttcccagatattattaagatacat
tggcaagaaaagaagagcaacacgattctgggatcccaggaggggaacac
catgaagactaacgacacatacatgaaatttagctggttaacggtgccag
aagagtcactggacaaagaacacagatgtatcgtcagacatgagaataat
aaaaacggaattgatcaagaaattatctttcctccaataaagacagatgt
catcacaatggatcccaaagacaattggtcaaaagatgcaaatgatacac
tactgctgcagctcacaaacacctctgcatattacatgtacctcctcctg
ctcctcaagagtgtggtctattttgccatcatcacctgctgtctgatgga
agaacggattctgctgcaatggagagaaatcaGCCACGAACTTCTCTCTG
TTAAAGCAAGCAGGAGACGTGGAAGAAAACCCCGGTCCCatgattcttac
tgtgggctttagcttttttgttttctacaggggcacgctgtgtgacaaag
taacccagagttccccggaccagacggtggcgagtggcagtgaggtggta
ctgctctgcacttacgacactg3'

HuLinkerDV4
(SEQ ID NO: 53)
5'catacattgtatcttgagaaattttcccagatattattaagatacat
tggcaagaaaagaagagcaacacgattctgggatcccaggaggggaacac
catgaagactaacgacacatacatgaaatttagctggttaacggtgccag
aagagtcactggacaaagaacacagatgtatcgtcagacatgagaataat
aaaaacggaattgatcaagaaattatctttcctccaataaagacagatgt
catcacaatggatcccaaagacaattggtcaaaagatgcaaatgatacac
tactgctgcagctcacaaacacctctgcatattacatgtacctcctcctg
ctcctcaagagtgtggtctattttgccatcatcacctgctgtctgatgga
agaacggattctgctgcaatggagagaaatcaGCCACGAACTTCTCTCTG
TTAAAGCAAGCAGGAGACGTGGAAGAAAACCCCGGTCCCATGTCACTTTC
TAGCCTGCTGAAGGTGGTCACAGCTTCACTGTGGCTAGGACCTGGCATTG
CCCAGAAGATAACTCAAACCCAACCAGGAATGTTCGTGCAGGAAAAGGAG
GCTGTGACTCTGG3'

HuLinkerDV5
(SEQ ID NO: 54)
5'catacattgtatcttgagaaattttcccagatattattaagatacat
tggcaagaaaagaagagcaacacgattctgggatcccaggaggggaacac
catgaagactaacgacacatacatgaaatttagctggttaacggtgccag
aagagtcactggacaaagaacacagatgtatcgtcagacatgagaataat
aaaaacggaattgatcaagaaattatctttcctccaataaagacagatgt
catcacaatggatcccaaagacaattggtcaaaagatgcaaatgatacac
tactgctgcagctcacaaacacctctgcatattacatgtacctcctcctg
ctcctcaagagtgtggtctattttgccatcatcacctgctgtctgatgga
agaacggattctgctgcaatggagagaaatcaGCCACGAACTTCTCTCTG
TTAAAGCAAGCAGGAGACGTGGAAGAAAACCCCGGTCCCATGGCCATGCT
CCTGGGGGCATCAGTGCTGATTCTGTGGCTTCAGCCAGACTGGGTAAACA
GTCAACAGAAGAATGATGACCAGCAAGTTAAGCAAAATTCACCATCCCTG
AGCGTCCAGGAAGGAAGAATTTCTATTCTGAACTGTGACTATACTAACAG
CATGTTTGATTATTTCCTATGGTACAAAAAATACCCTGCTGAAGGTCCTA
CATTCCTGATATC3'

LIST OF SEQUENCES

HuLinkerDV6
(SEQ ID NO: 55)
5'catacattgtatcttgagaaattttcccagatattattaagatacat
tggcaagaaaagaagagcaacacgattctgggatcccaggaggggaacac
catgaagactaacgacacatacatgaaatttagctggttaacggtgccag
aagagtcactggacaaagaacacagatgtatcgtcagacatgagaataat
aaaaacggaattgatcaagaaattatctttcctccaataaagacagatgt
catcacaatggatcccaaagacaattggtcaaaagatgcaaatgatacac
tactgctgcagctcacaaacacctctgcatattacatgtacctcctcctg
ctcctcaagagtgtggtctattttgccatcatcacctgctgtctgatgga
agaacggattctgctgcaatggagagaaatcaGCCACGAACTTCTCTCTG
TTAAAGCAAGCAGGAGACGTGGAAGAAAACCCCGGTCCCATGGACAAGAT
CTTAGGAGCATCATTTTTAGTTCTGTGGCTTCAACTATGCTGGGTGAGTG
GCCAACAGAAGGAGAAAGTGACCAGCAGCAGGTGAAACAAAGTCCTCAA
TCTTTGATAGTCCAGAAAGGAGGGATTTCAATTATAAACTGTGCTTATGA
GAACACTGCGTTTGACTACTTTCCATGGTACC3'

HuLinkerDV7
(SEQ ID NO: 56)
5'catacattgtatcttgagaaattttcccagatattattaagatacat
tggcaagaaaagaagagcaacacgattctgggatcccaggaggggaacac
catgaagactaacgacacatacatgaaatttagctggttaacggtgccag
aagagtcactggacaaagaacacagatgtatcgtcagacatgagaataat
aaaaacggaattgatcaagaaattatctttcctccaataaagacagatgt
catcacaatggatcccaaagacaattggtcaaaagatgcaaatgatacac
tactgctgcagctcacaaacacctctgcatattacatgtacctcctcctg
ctcctcaagagtgtggtctattttgccatcatcacctgctgtctgatgga
agaacggattctgctgcaatggagagaaatcaGCCACGAACTTCTCTCTG
TTAAAGCAAGCAGGAGACGTGGAAGAAAACCCCGGTCCCATGATGAAGTG
TCCACAGGCTTTACTAGCTATCTTTTGGCTTCTACTGAGCTGGGTGAGCA
GTGAAGACAAGGTGGTACAAAGCCCTCTATCTCTGGTTGTCCACGAGGGA
G3'

HuLinkerDV8
(SEQ ID NO: 57)
5'catacattgtatcttgagaaattttcccagatattattaagatacat
tggcaagaaaagaagagcaacacgattctgggatcccaggaggggaacac
catgaagactaacgacacatacatgaaatttagctggttaacggtgccag
aagagtcactggacaaagaacacagatgtatcgtcagacatgagaataat
aaaaacggaattgatcaagaaattatctttcctccaataaagacagatgt
catcacaatggatcccaaagacaattggtcaaaagatgcaaatgatacac
tactgctgcagctcacaaacacctctgcatattacatgtacctcctcctg
ctcctcaagagtgtggtctattttgccatcatcacctgctgtctgatgga
agaacggattctgctgcaatggagagaaatcaGCCACGAACTTCTCTCTG
TTAAAGCAAGCAGGAGACGTGGAAGAAAACCCCGGTCCCATGGCATGCCC
TGGCTTCCTGTGGGCACTTGTGATCTCCACCTGTCTTGAATTTAGCATGG
CTCAGACAGTCACTCAGTCTCAACCAGAGATGTCTGTGCAGGAGGCAGAG
ACCGTGACCCTGAGCTGCACATATGACACCAGTGAGAGTGATTATTATTT
ATTCTGGTACAAGCAGCCTCCCAG3'

Paired amino acid sequence in TRGV9-CDR3 region
(SEQ ID NO: 58)
ALFIQELGKKIKV (SEQ ID NO: 60)
ALWDGPYYKKL (SEQ ID NO: 62)
ALWDIPPGQELGKKIKV (SEQ ID NO: 64)
ALWEAQELGKKIKV (SEQ ID NO: 66)
ALWEARQELGKKIKV (SEQ ID NO: 68)
ALWEGTRGQELGKKIKV (SEQ ID NO: 70)
ALWEVGDQELGKKIKV (SEQ ID NO: 72)
ALWEVHSELGKKIKV (SEQ ID NO: 72)
ALWEVHSELGKKIKV (SEQ ID NO: 74)
ALWEVLELGKKIKV (SEQ ID NO: 76)
ALWEVLVGELGKKIKV (SEQ ID NO: 78)
ALWEVPELGKKIKV (SEQ ID NO: 80)
ALWEVQELGKKIKV (SEQ ID NO: 80)
ALWEVQELGKKIKV (SEQ ID NO: 80)
ALWEVQELGKKIKV (SEQ ID NO: 80)
ALWEVQELGKKIKV (SEQ ID NO: 80)
ALWEVQELGKKIKV (SEQ ID NO: 80)
ALWEVQELGKKIKV (SEQ ID NO: 87)
ALWEVRELGKKIKV (SEQ ID NO: 87)
ALWEVRELGKKIKV (SEQ ID NO: 90)
ALWEVRKQELGKKIKV

LIST OF SEQUENCES

ALWEVTHNRQELGKKIKV (SEQ ID NO: 92)

ALWGGAAGAYYKKL (SEQ ID NO: 94)

ALWGGELGKKIKV (SEQ ID NO: 96)

ALWVQELGKKIKV (SEQ ID NO: 98)

ALWEAHQELGKKIKV (SEQ ID NO: 100)

ALWEANKKL (SEQ ID NO: 102)

ALWEAQELGKKIKV (SEQ ID NO: 104)

ALWEATGLGKKIKV (SEQ ID NO: 106)

ALWEDLELGKKIKV (SEQ ID NO: 108)

ALWEKEELGKKIKV (SEQ ID NO: 110)

ALWEKELGKKIKV (SEQ ID NO: 112)

ALWEMTQELGKKIKV (SEQ ID NO: 114)

ALWEPQELGKKIKV (SEQ ID NO: 116)

ALWESKELGKKIKV (SEQ ID NO: 118)

ALWEVGELGKKIKV (SEQ ID NO: 120)

ALWEVHKLGKKIKV (SEQ ID NO: 122)

ALWEVKELGKKIKV (SEQ ID NO: 124)

ALWEVLQQELGKKIKV (SEQ ID NO: 126)

ALWEVPVLGKKIKV (SEQ ID NO: 128)

ALWEVQELGKKIKV (SEQ ID NO: 80)

ALWEVQELGKKIKV (SEQ ID NO: 80)

ALWEVQELGKKIKV (SEQ ID NO: 80)

ALWEVRELGKKIKV (SEQ ID NO: 87)

ALWEVRELGKKIKV (SEQ ID NO: 87)

ALWEVRQELGKKIKV (SEQ ID NO: 135)

ALWEVRQELGKKIKV (SEQ ID NO: 137)

ALWEVTELGKKIKV (SEQ ID NO: 139)

ALWGRELGKKIKV (SEQ ID NO: 141)

Paired amino acid sequence in TRDV2-CDR3 region

ACDVLGDTEGRLI (SEQ ID NO: 59)

ACDTVFTGGYSSWDTRQMF (SEQ ID NO: 61)

ACDTLGETSSWDTRQMF (SEQ ID NO: 63)

ACDSGGYSSWDTRQMF (SEQ ID NO: 65)

ACDTLFPGGSATDKLI (SEQ ID NO: 67)

ACDTVGAHTDKLI (SEQ ID NO: 69)

ACDPLNTGGSFSLYTDKLI (SEQ ID NO: 71)

ACDTGGFRSSWDTRQMF (SEQ ID NO: 73)

ACDTGGFRSSWDTRQMF (SEQ ID NO: 73)

ACDTVGMGIRLGDKLI (SEQ ID NO: 75)

ACDILGINTDKLI (SEQ ID NO: 77)

ACERLGDYVPDKLI (SEQ ID NO: 79)

ACDRLLGDTDKLI (SEQ ID NO: 81)

ACDTVAPRIGGLKYTDKLI (SEQ ID NO: 82)

ACDTVGGPYTDKLI (SEQ ID NO: 83)

ACDTVGGTAQ (SEQ ID NO: 84)

ACDTVSGGSTPTWYTDKLI (SEQ ID NO: 85)

ACDTVSIFTGDTTDKLI (SEQ ID NO: 86)

ACDTILIFSPTGGDTDKLI (SEQ ID NO: 88)

ACVPLGDWTDKLI (SEQ ID NO: 89)

ACDTLGDDFDKLI (SEQ ID NO: 91)

ACDTLLGTEAWDTRQMF (SEQ ID NO: 93)

LIST OF SEQUENCES

ACDGKTTDTDKLI (SEQ ID NO: 95)

ACDLLGDTRYTDKLI (SEQ ID NO: 97)

ACVGITGDTDKLI (SEQ ID NO: 91)

ACDSLGDSVDKLI (SEQ ID NO: 101)

ACDLLRGAGGQIDKLI (SEQ ID NO: 103)

ACDTVGGAFDTDKLI (SEQ ID NO: 105)

ACDMGDTRSWDTRQMF (SEQ ID NO: 107)

ACDTVSWGKNTDKLI (SEQ ID NO: 109)

ACDTGDWGSSWDTRQMF (SEQ ID NO: 111)

ACDILDSTGGTDLTAQLF (SEQ ID NO: 113)

ACDTVRNTGGYAFAGIDKLI (SEQ ID NO: 115)

ACDKVLGDSSWDTRQMF (SEQ ID NO: 117)

ACEGLGATQSSWDTRQMF (SEQ ID NO: 119)

ACDKLLGDNELI (SEQ ID NO: 121)

ACDSLLGKGTDKLI (SEQ ID NO: 123)

ACDTLRGSADKLI (SEQ ID NO: 125)

ACDTVPARHTDKLI (SEQ ID NO: 127)

ACDTADRSSYTDKLI (SEQ ID NO: 129)

ACDTLLGDPSSWDTRQMF (SEQ ID NO: 130)

ACDTLSGGYARTDKLI (SEQ ID NO: 131)

ACDTVGILGDTGLGLI (SEQ ID NO: 132)

ACDTIVSGYDGYDKLI (SEQ ID NO: 133)

ACSILGDKTSDKLI (SEQ ID NO: 134)

ACDTVSQRGGYSDKLI (SEQ ID NO: 136)

ACDPLERVGGPANTDKLI (SEQ ID NO: 138)

ACDVLGDTGDDKLI (SEQ ID NO: 140)

ACDTVGSNTDKLI (SEQ ID NO: 142)

ACDVLGDTEADKLI (SEQ ID NO: 143)

ACDPLEGAGGHNTDKLI (SEQ ID NO: 145)

GILGFVFTL (SEQ ID NO: 146)

TRGV1-3
External Primer:
GCAGCTGGAGCAAACTG (SEQ ID NO: 147)

Internal Primer:
CTGAATTATCGGTCACCAG (SEQ ID NO: 148)

TRGV4
External Primer:
CAAATATCCTGTAAAGTTTTCATC (SEQ ID NO: 149)

Internal Primer:
GTTTAGAGTTTCTATTATATGTCCTTGCAAC (SEQ ID NO: 150)

TRGV5
External Primer:
GATATCTCAGGATCAGCTCTCC (SEQ ID NO: 151)

Internal Primer:
TACCCGAAGACCAAACAAGAC (SEQ ID NO: 152)

TRGV6
External Primer:
TCACCTCTGGGGTCATATG (SEQ ID NO: 153)

Internal Primer:
AGAGGAAAGGAAATACGGC (SEQ ID NO: 154)

TRGV7
External Primer:
CAACTTGGAAGAAAGAATAATGTC (SEQ ID NO: 155)

Internal Primer:
CACCAAGCTAGAGGGGTC (SEQ ID NO: 156)

TRGC (reverse)
External Primer:
CTTTTCTTTCCAATACACCC (SEQ ID NO: 157)

Internal Primer:
TCDGGAAAGAACTTTTCAAGG (SEQ ID NO: 158)

TRDV1
External Primer:
ACCCAAATGTTGCATCAG (SEQ ID NO: 159)

Internal Primer:
GTCTCTGACAATCCAAGAAGG (SEQ ID NO: 160)

TRDV2

LIST OF SEQUENCES

```
External Primer:
                                        (SEQ ID NO: 161)
TCTGTGCAGGTGGCAG Internal Primer:
                                        (SEQ ID NO: 162)
CCCTGGACTGCACCTATG TRDV4
External Primer:
                                        (SEQ ID NO: 163)
TGTATATTTGGAACCAGTTGC Internal Primer:
                                        (SEQ ID NO: 164)
GATCCTGCCTCCTTCTACTG TRDV5
External Primer:
                                        (SEQ ID NO: 165)
CATCACGCTGACCCAG Internal Primer:
                                        (SEQ ID NO: 166)
GCTCCACTGACCAGACAG TRDV6/TRAV15
External Primer:
                                        (SEQ ID NO: 167)
CASCTTYTTAGTGGAGAGATGG Internal Primer:
                                        (SEQ ID NO: 168)
AYTCTGTAGTCTTCCAGAAATCAC TRDV7/TRAV13
External Primer:
                                        (SEQ ID NO: 169)
TCCTTGGTTCTGCAGG Internal Primer:
                                        (SEQ ID NO: 170)
TGCAGGAGGGGGAGA TRDV8/TRAV14
External Primer:
                                        (SEQ ID NO: 171)
GCAGCAGGTGAGACAAAG Internal Primer:
                                        (SEQ ID NO: 172)
CTCTGACAGTCTGGGAAGG TRDV9/TRAV6-1/6-2
External Primer:
                                        (SEQ ID NO: 173)
CAGATGCAAGGTCAAGTGAC
```

```
Internal Primer:
                                        (SEQ ID NO: 174)
GGAGAAGGTCCACAGCTC TRDV9/TRAV6-3/6-4
External Primer:
                                        (SEQ ID NO: 175)
AAGGTCCACAGCTCCTTC Internal Primer:
                                        (SEQ ID NO: 176)
CAACTGCCAACAACAAGG TRDV9/TRAV6-5/6-7
External Primer:
                                        (SEQ ID NO: 177)
GTTCTGGTATGTGCAGTATCC Internal Primer:
                                        (SEQ ID NO: 178)
TCCTTCCACTTGCAGAAAG TRDV10/TRAV4
External Primer:
                                        (SEQ ID NO: 179)
TCTGSTCTGAGATGCAATTTT Internal Primer:
                                        (SEQ ID NO: 180)
GGITIMAGGAACAAAGGAGAAT TRDV11/TRAV16
External Primer:
                                        (SEQ ID NO: 181)
GTACAAGCAAACAGCAAGTG Internal Primer:
                                        (SEQ ID NO: 182)
ATTATTCTCTGAACTTTCAGAAGC TRDV12/TRAV21
External Primer:
                                        (SEQ ID NO: 183)
GTGCACTTGCCTTGTAGC Internal Primer:
                                        (SEQ ID NO: 184)
AATAGTATGGCTTTCCTGGC TRDC (reverse)
External Primer:
                                        (SEQ ID NO: 185)
TGAAAGAATTTTGCATATGGTTC Internal Primer:
                                        (SEQ ID NO: 186)
GAGATGACTATAGCAGGGTCG
```

---

What is claimed is:

1. A method for cloning a T cell receptor (TCR) from a single T cell, wherein said method comprises:
   (a) performing RT-PCR with a primer mixture on a single T cell to simultaneously obtain both α-chain and β-chain TCR DNA sequences or both γ-chain and δ-chain TCR DNA sequences, wherein said TCR DNA sequences comprise a partial variable (V) region, CDR3 region, and a partial constant (C) region, wherein the primer mixture comprises:
      (i) sense primers comprising T-cell receptor alpha variable (TRAV) sequences and/or T cell receptor beta variable (TRBV) sequences and antisense primers comprising T-cell receptor alpha constant (TRAC) sequences and/or T-cell receptor beta constant (TRBC) sequences, wherein the TRAV and/or TRBV sense primers and the TRAC and/or TRBC antisense primers are selected from the primers comprising SEQ ID NO: 27-36, 167-184, and 187-315, or
      (ii) sense primers comprising T-cell receptor gamma variable (TRGV) sequences and/or T cell receptor delta variable (TRDV) sequences and antisense primers comprising T-cell receptor gamma constant (TRGC) sequences and/or T-cell receptor delta constant (TRDC) sequences, wherein the TRGV and/or TRDV sense primers and the TRGC and/or TRDC antisense primers are selected from the primers having SEQ ID NO: 1-38 and 147-186,
   (b) optionally sequencing the RT-PCR product obtained in step (a), and
   (c) cloning the paired αβ or γδ full length TCR CDR3 DNA sequences obtained in step (a) into a corresponding TCRαβ or TCRγδ library.

2. The method of claim 1, wherein said T cell is a human or a mouse αβ or γδ T cell.

3. The method of claim 1, comprising sorting of single T cells prior to step (a).

4. The method of claim 3, wherein T cells are not stimulated prior to sorting.

5. The method of claim 1, wherein the TRGV and/or TRDV sense primers and the TRGC and/or TRDC antisense primers are selected from the primers having SEQ ID NO: 1-38.

6. The method of claim 1, wherein the single cell RT-PCR of γδ or αβ TCR and sequencing are performed within not more than 2 days.

7. The method of claim 1, wherein the TRGV and/or TRDV sense primers and the TRGC and/or TRDC antisense primers are selected from the primers having SEQ ID NO: 147-186.

8. The method of claim 1, wherein the TRAV and/or TRBV sense primers and the TRAC and/or TRBC antisense primers are selected from the primers having SEQ ID NO: 167-184, 187-247 and 315.

9. The method of claim 1, wherein the TRAV and/or TRBV sense primers and the TRAC and/or TRBC antisense primers are selected from the primers having SEQ ID NO: 248-314 and 27-36.

10. The method of claim 1, wherein the primer mixture comprises primers having SEQ ID NOS: 1-38.

11. The method of claim 1, wherein the primer mixture comprises primers having SEQ ID NOS: 248-314 and 27-36.

* * * * *

UNITED STATES PATENT AND TRADEMARK OFFICE
CERTIFICATE OF CORRECTION

PATENT NO. : 12,297,427 B2
APPLICATION NO. : 15/780938
DATED : May 13, 2025
INVENTOR(S) : Paul Thomas, Xizhi Guo and Pradyot Dash It is certified that error appears in the above-identified patent and that said Letters Patent is hereby corrected as shown below:

In the Claims

Column 161, Line 58 - In Claim 1, part (c), delete "full length".

Signed and Sealed this
Twenty-fourth Day of June, 2025

Coke Morgan Stewart
*Acting Director of the United States Patent and Trademark Office*